(12) United States Patent
Wernke et al.

(10) Patent No.: US 11,213,409 B2
(45) Date of Patent: Jan. 4, 2022

(54) CONDUCTIVE HUMAN INTERFACES

(71) Applicant: WillowWood Global LLC, Mt. Sterling, OH (US)

(72) Inventors: Matthew Wernke, Columbus, OH (US); Michael L. Haynes, Columbus, OH (US); Christopher T. Kelley, Grandview Heights, OH (US); Anne Marie Tollett, Grove City, OH (US); Joseph M. Bryant, Lancaster, OH (US)

(73) Assignee: WILLOWWOOD GLOBAL LLC, Mt. Sterling, OH (US)

( * ) Notice: Subject to any disclaimer, the term of this patent is extended or adjusted under 35 U.S.C. 154(b) by 0 days.

(21) Appl. No.: 16/402,555

(22) Filed: May 3, 2019

(65) Prior Publication Data

US 2019/0254845 A1 Aug. 22, 2019

Related U.S. Application Data

(63) Continuation-in-part of application No. 15/675,088, filed on Aug. 11, 2017.
(Continued)

(51) Int. Cl.
*A61B 5/04* (2006.01)
*A61F 2/68* (2006.01)
(Continued)

(52) U.S. Cl.
CPC .............. *A61F 2/72* (2013.01); *A61B 5/296* (2021.01); *A61F 2/7812* (2013.01); *A61B 2562/0215* (2017.08)

(58) Field of Classification Search
CPC ........ A61F 2/72; A61F 2/68; A61F 2002/704; A61F 2/583; A61F 2/54;
(Continued)

(56) References Cited

U.S. PATENT DOCUMENTS

| 4,522,211 A | 6/1985 | Bare et al. |
| 4,898,783 A | 2/1990 | McCullough, Jr. et al. |

(Continued)

FOREIGN PATENT DOCUMENTS

| DE | 102014106070 A1 | 11/2015 |
| WO | 00/71024 A1 | 11/2000 |

(Continued)

OTHER PUBLICATIONS

Thomas. "From Snap Fits to Adhesives: A Comprehensive Guide to Mechanical Fastener Options". May 2016. (Year: 2016).*
(Continued)

*Primary Examiner* — Joseph A Stoklosa
*Assistant Examiner* — Brian M Antiskay
(74) *Attorney, Agent, or Firm* — Thompson Hine LLP

(57) ABSTRACT

An electrode is supported on a prosthetic liner to communicate electrically with a residual limb. A housing is fixed to the liner, and is receivable in a socket in an installed position. A processor is installed in the housing in communication with the electrode. Electrical signal contacts are exposed at a distal end of the housing for contacting electrical signal contacts in the socket. The housing defines a ground current path that communicates with a ground contact in the socket.

13 Claims, 38 Drawing Sheets

Related U.S. Application Data

(60) Provisional application No. 62/669,433, filed on May 10, 2018, provisional application No. 62/373,670, filed on Aug. 11, 2016.

(51) Int. Cl.
*A61F 2/72* (2006.01)
*A61F 2/78* (2006.01)
*A61B 5/296* (2021.01)

(58) Field of Classification Search
CPC .. A61F 2002/7615; A61F 2/60; A61F 2/7812; A61F 2/70; A61F 2/76; A61B 5/04001; A61B 5/0478; A61B 5/0484; A61B 5/0488; A61B 5/7264; A61B 5/04012; A61B 5/0482; A61B 5/04888; A61B 5/4851; A61B 5/04805
USPC ............... 600/372, 382, 386, 388–390, 393, 600/544–545; 607/115; 623/24–25, 33, 623/36–37, 58–65
See application file for complete search history.

(56) References Cited

U.S. PATENT DOCUMENTS

| | | | |
|---|---|---|---|
| 5,443,525 | A | 8/1995 | Laghi |
| 5,606,149 | A | 2/1997 | Yaworski et al. |
| 6,803,332 | B2 | 10/2004 | Andrews |
| 8,123,568 | B2 | 2/2012 | Meyer et al. |
| 8,320,988 | B2 | 11/2012 | Axelgaard |
| 8,591,599 | B1* | 11/2013 | Kaliki ................ A61B 5/6828 600/372 |
| 8,948,839 | B1 | 2/2015 | Longinotti-Buitoni et al. |
| 8,979,944 | B2 | 3/2015 | Laghi et al. |
| 9,155,634 | B2 | 10/2015 | Lipschutz et al. |
| 2003/0175513 | A1 | 9/2003 | Tokarsky et al. |
| 2004/0015222 | A1 | 1/2004 | Nielsen |
| 2005/0049481 | A1 | 3/2005 | Gray et al. |
| 2005/0184619 | A1 | 8/2005 | Chen |
| 2005/0283061 | A1* | 12/2005 | Ryu .................... A61B 5/30 600/372 |
| 2005/0288775 | A1 | 12/2005 | Dong |
| 2007/0021841 | A1 | 1/2007 | Al-Temen et al. |
| 2007/0078324 | A1 | 4/2007 | Wijisiriwardana |
| 2009/0076363 | A1* | 3/2009 | Bly .................... A61B 5/30 600/372 |
| 2009/0216339 | A1 | 8/2009 | Hanson |
| 2010/0114238 | A1 | 5/2010 | Muccio |
| 2011/0077497 | A1* | 3/2011 | Oster .................. A61B 5/274 600/372 |
| 2011/0092790 | A1* | 4/2011 | Wilder-Smith ...... A61B 5/6843 600/388 |
| 2011/0230747 | A1 | 9/2011 | Rogers et al. |
| 2011/0251469 | A1 | 10/2011 | Varadan |
| 2012/0126199 | A1 | 5/2012 | O'Brien et al. |
| 2012/0296445 | A1 | 11/2012 | Leiniger |
| 2013/0041235 | A1 | 2/2013 | Rogers et al. |
| 2013/0046394 | A1* | 2/2013 | Lipschutz ............ A61F 2/7812 623/25 |
| 2013/0093287 | A1 | 4/2013 | Biso et al. |
| 2013/0248163 | A1 | 9/2013 | Bhagwagar et al. |
| 2014/0005763 | A1 | 1/2014 | Cederna et al. |
| 2014/0025183 | A1 | 1/2014 | Kelley |
| 2014/0148916 | A1 | 5/2014 | Laghi et al. |
| 2014/0296651 | A1* | 10/2014 | Stone ................. A61B 5/1135 600/301 |
| 2014/0371568 | A1* | 12/2014 | Selby .................. H01R 13/17 600/388 |
| 2015/0087951 | A1* | 3/2015 | Felix .................. A61B 5/25 600/382 |
| 2015/0335288 | A1 | 11/2015 | Toth et al. |
| 2016/0038314 | A1* | 2/2016 | Kuiken ................ A61F 2/76 623/36 |
| 2016/0158034 | A1 | 6/2016 | Laghi et al. |
| 2016/0194792 | A1 | 7/2016 | Satharasinghe et al. |
| 2018/0296822 | A1 | 10/2018 | Schroeder |

FOREIGN PATENT DOCUMENTS

| | | |
|---|---|---|
| WO | 2014/197822 A2 | 12/2014 |
| WO | 2016007090 A1 | 1/2016 |
| WO | 2016/019250 A1 | 2/2016 |
| WO | 2019032118 A1 | 2/2019 |

OTHER PUBLICATIONS

Pomona Electronics Catalog, vol. 54. Printed Jul. 2015. (Year: 2015).*
Partial European Search Report in European Patent Application No. 20172782.3, dated Sep. 30, 2020 (10 pages).
(EP) European Patent Office, Extended Search Report, European Patent Application No. 20172782.3, 9 pages, dated May 6, 2021.
(U.S.) U.S. Patent and Trademark Office, Non-Final Office Action, U.S. Appl. No. 15/675,088, 22 pages, dated Jul. 23, 2021.
European Patent Office, European Search Report and Search Opinion, European Patent Application No. 17920618.0, 7 pages (dated Apr. 23, 2020).
European Patent Office, Communication Pursuant to Article 94(3) EPC (Examination Report), European Patent Application No. 17920618.0, 6 pages (dated Nov. 27, 2020).
European Patent Office, Communication Pursuant to Article 94(3) EPC (Examination Report), European Patent Application No. 17920618.0, 6 pages (dated Apr. 12, 2021).
U.S. Patent and Trademark Office (ISA/US), International Search Report, International Application No. PCT/US2017/046513, 4 pages (dated Dec. 14, 2017).
U.S. Patent and Trademark Office (ISA/US), Written Opinion of the International Searching Authority, International Application No. PCT/US2017/046513, 10 pages (dated Dec. 14, 2017).
International Bureau of WIPO, International Preliminary Report on Patentability, International Application No. PCT/2017/046513, 11 pages (dated Feb. 11, 2020).
(EP) European Patent Office, Search Report and Search Opinion, European Patent Application No. 17859260.6, 9 pages, dated Apr. 23, 2020.
(PCT) U.S. Patent and Trademark Office (ISA/US), International Search Report, International Application No. PCT/US2017/055538, 2 pages, dated Dec. 28, 2017.
(PCT) U.S. Patent and Trademark Office (ISA/US), Written Opinion of the International Searching Authority, International Application No. PCT/US2017/055538, 6 pages, dated Dec. 28, 2017.
(U.S.) U.S. Patent and Trademark Office, Non-Final Office Action, U.S. Appl. No. 15/726,624, 8 pages, dated Mar. 17, 2021.
U.S. Patent and Trademark Office, Final Office Action, U.S. Appl. No. 15/726,624, 10 pages, dated Sep. 30, 2021.

* cited by examiner

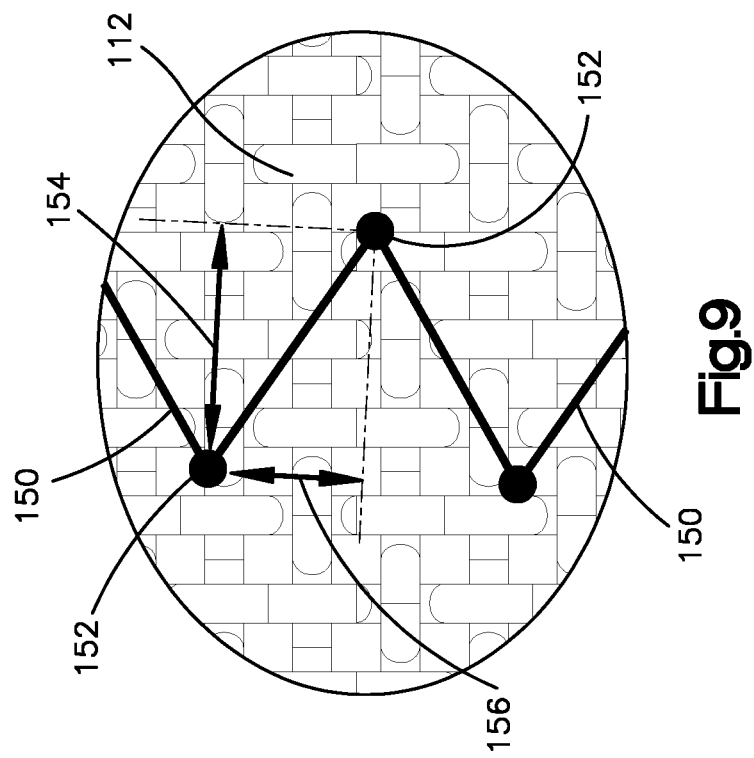
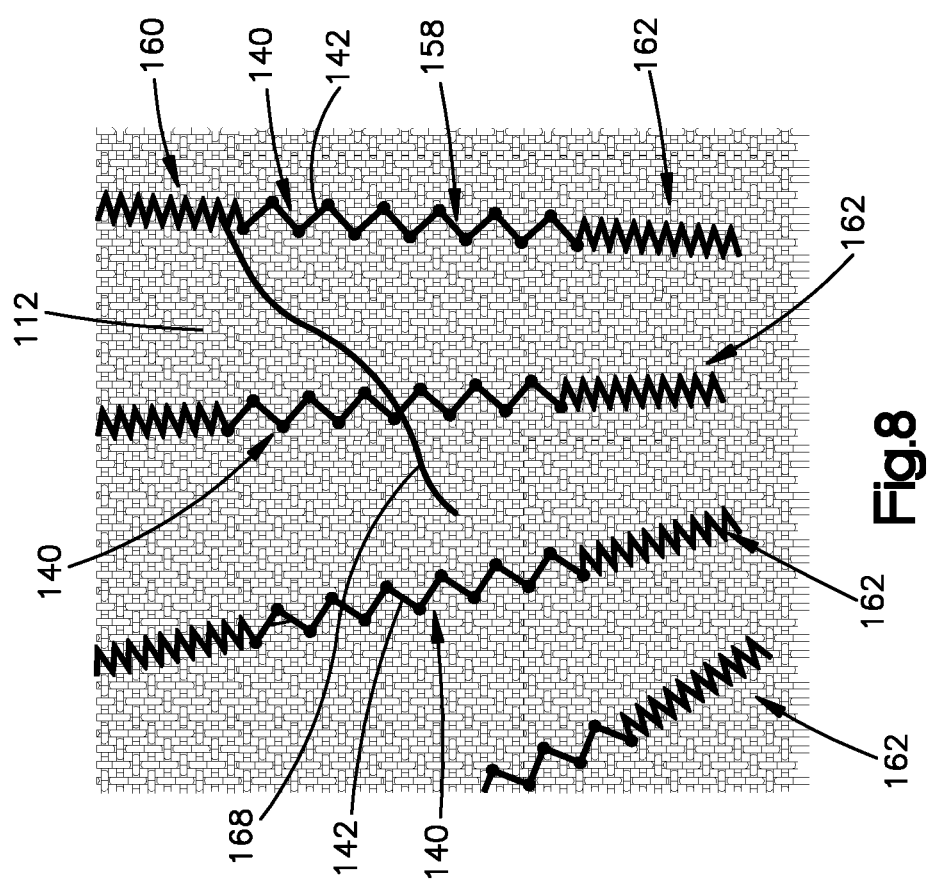

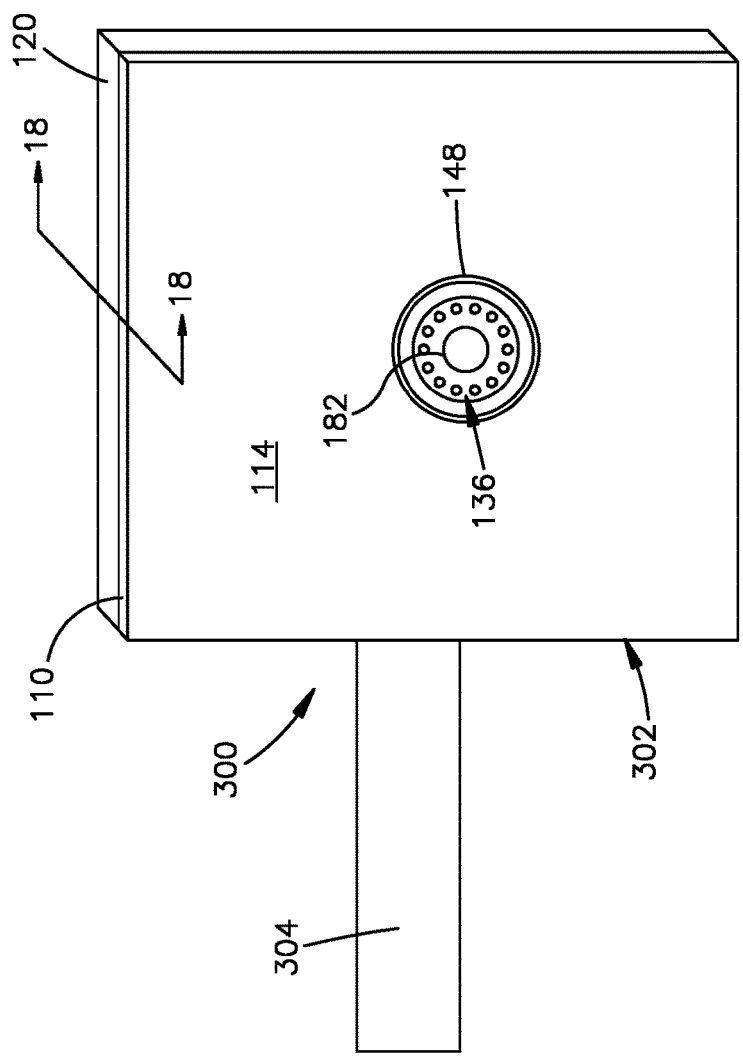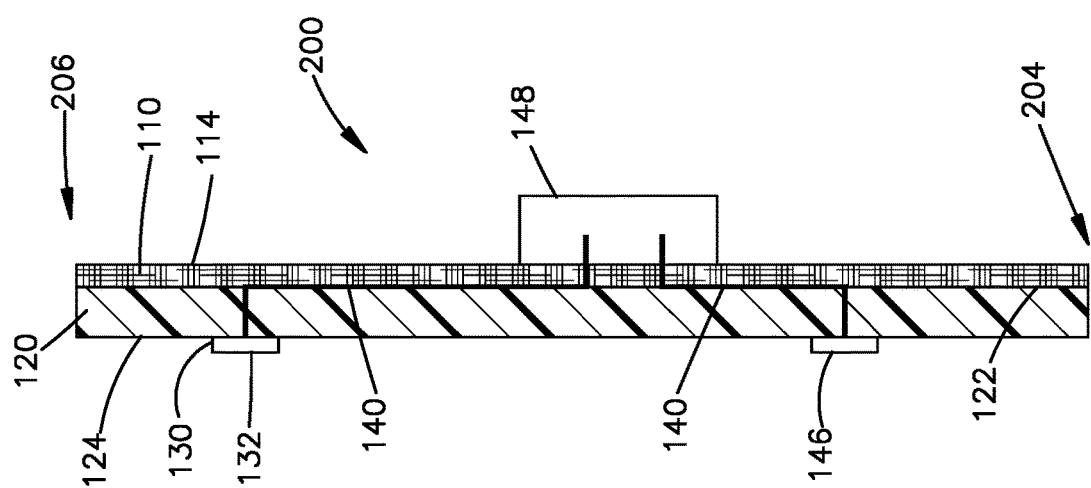

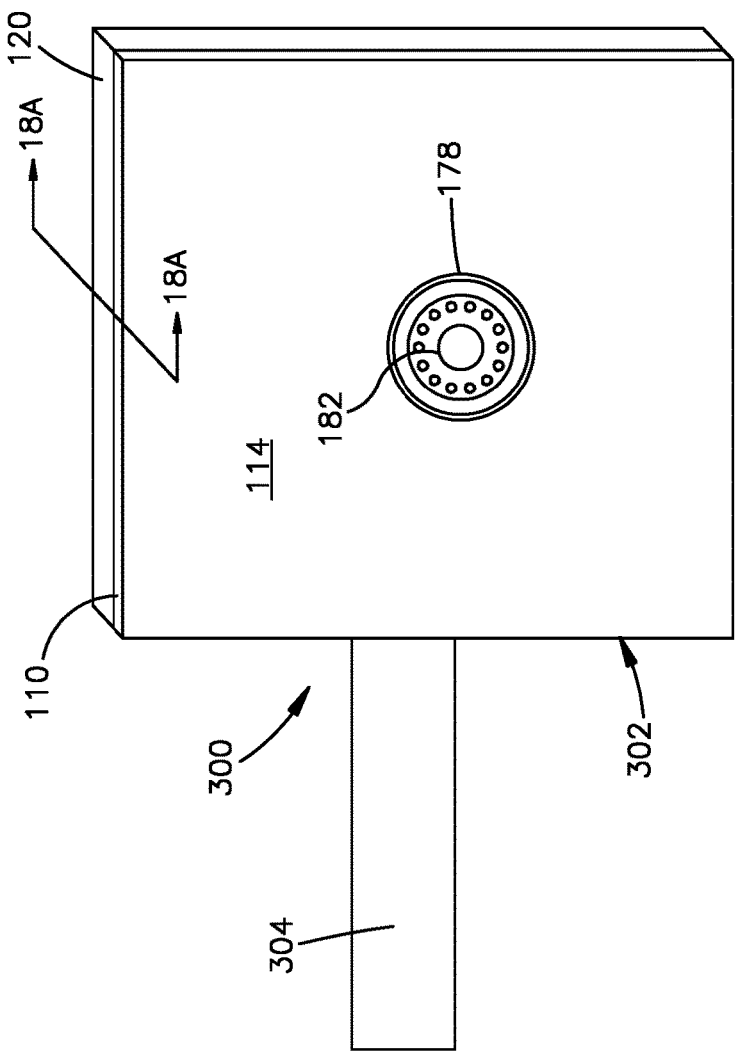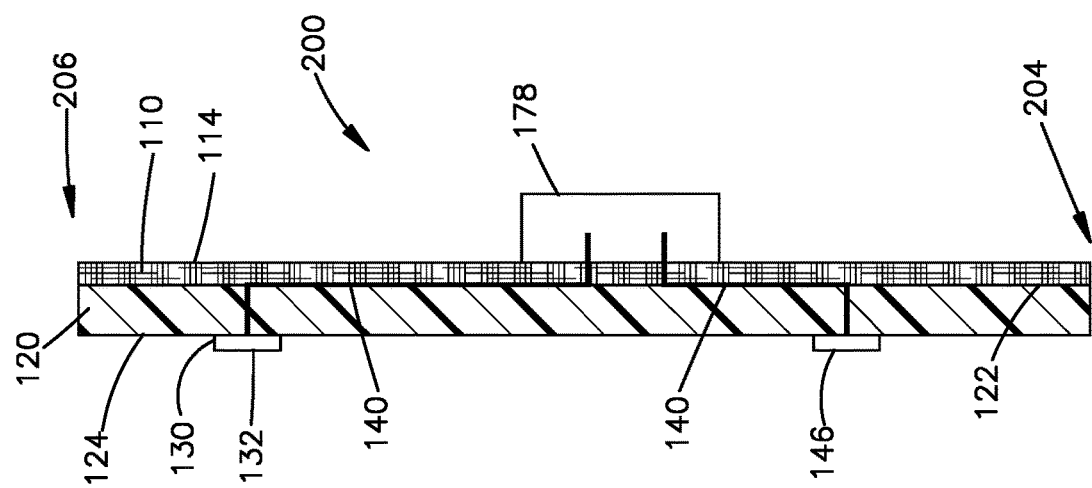

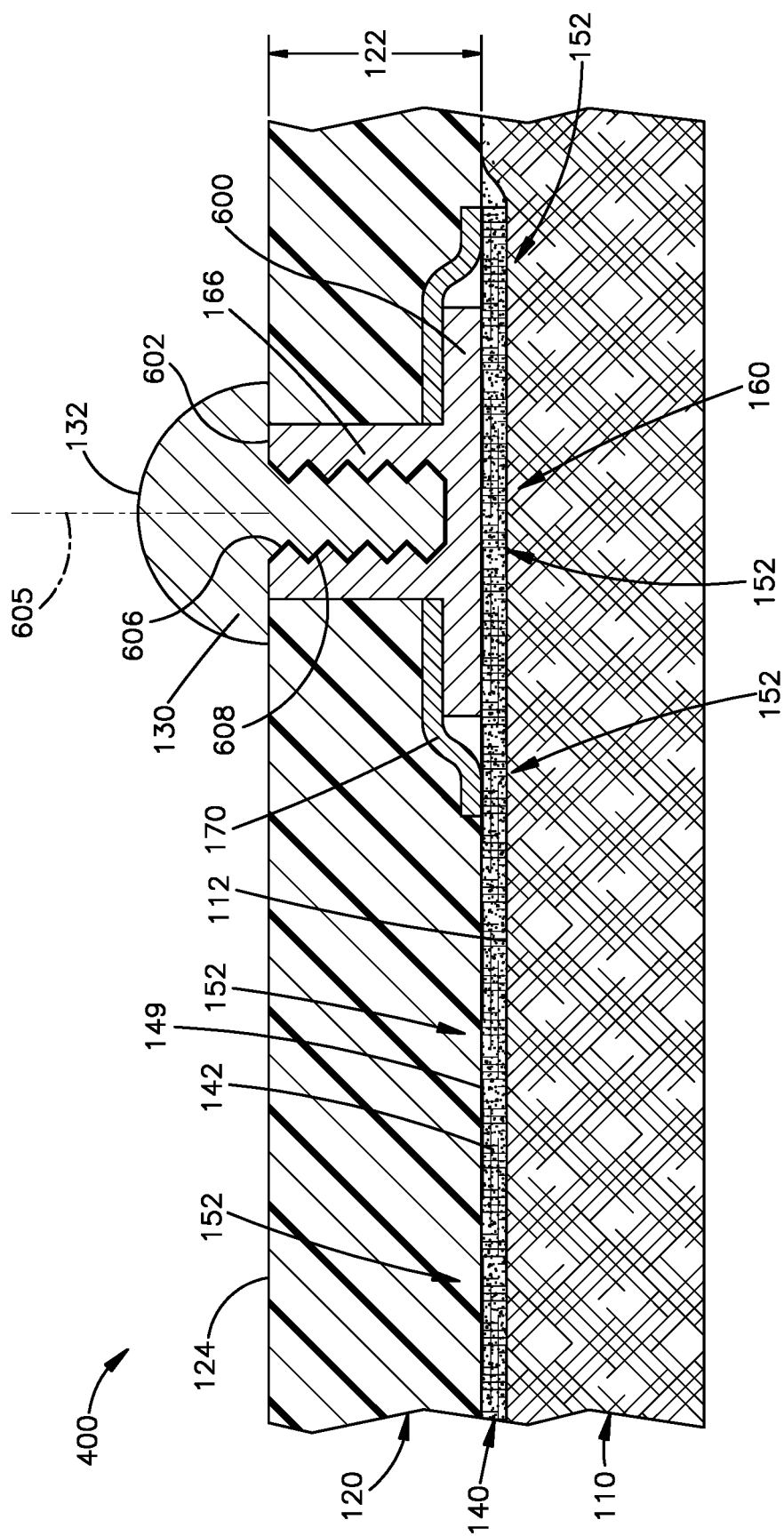

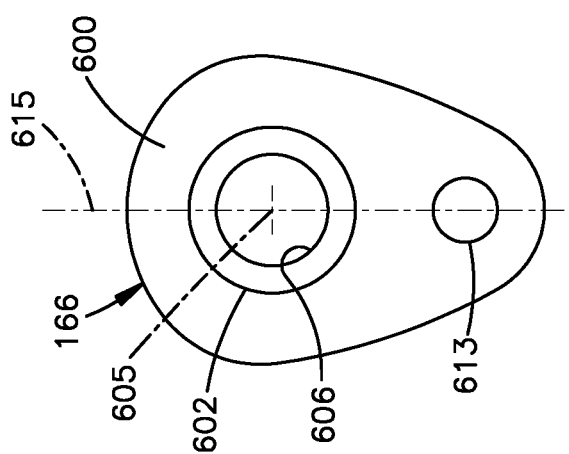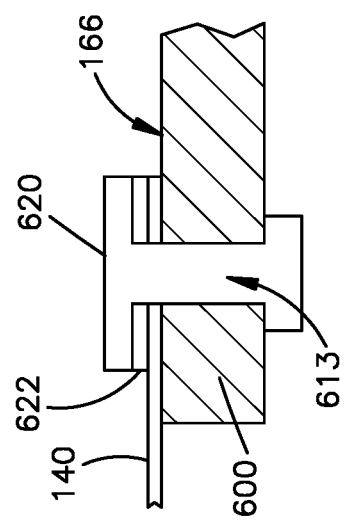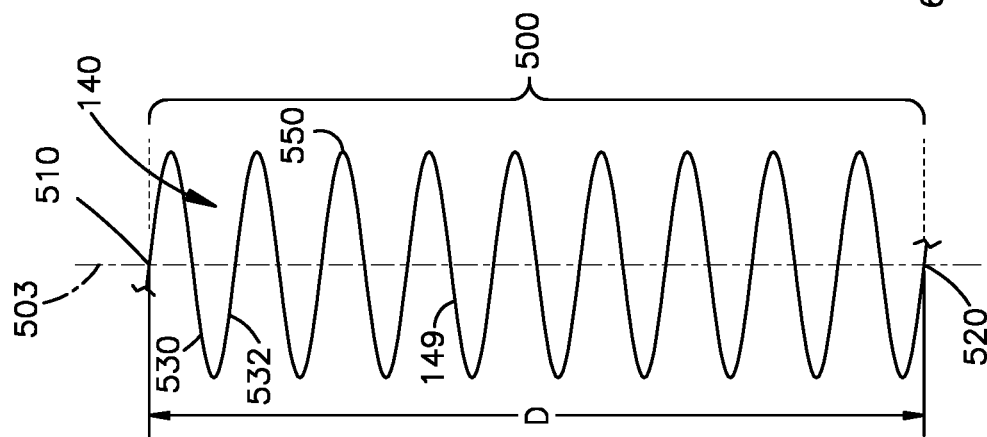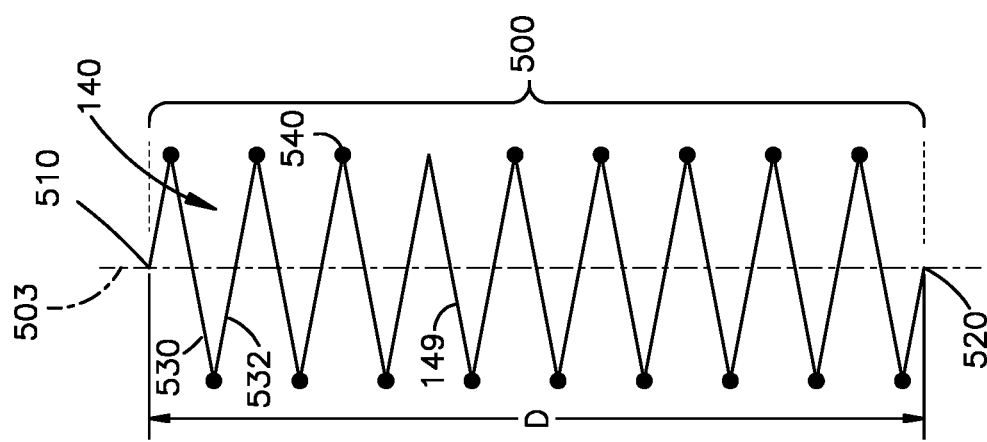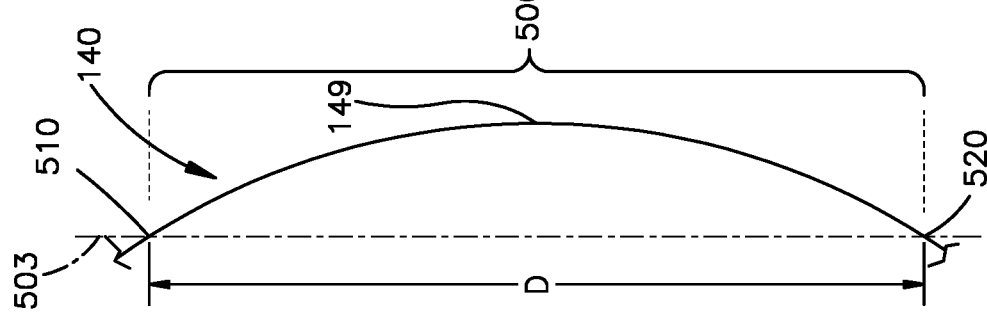

CONDUCTIVE HUMAN INTERFACES

RELATED APPLICATIONS

This application claims the benefit of provisional U.S. patent application 62/669,433, filed May 10, 2018, and is a continuation-in-part of U.S. patent application Ser. No. 15/675,088, filed Aug. 11, 2017, which claims the benefit of provisional U.S. patent application 62/373,670, filed Aug. 11, 2016. Each of these prior applications is incorporated by reference into this application.

TECHNICAL FIELD

This technology includes a conductive human interface for transmitting signals between a device and a user of the device, such as electromyographic signals that are transmitted from a user, and transcutaneous electrical nerve stimulation signals that are transmitted to a user.

BACKGROUND

Electromyographic (EMG) signals are relatively low voltage electrical signals, in the range of about 10 μV to about 1 mV, that are generated in muscle tissue during contraction. Control of assistive devices using EMG signals can increase the functionality and the ease of use for a number of devices. For example, instead of requiring hand or body control of an assistive device such as a prosthetic, the EMG signals can be detected and used as input for the control of the device.

The low voltage of EMG signals can be detected by interfaces that place electrodes upon the skin of the user. Generally, additional electrical components are needed to process or amplify the EMG signals in order to generate signals suitable for control input. Thus, the EMG signals must be communicated from the detection site to the electrical components.

SUMMARY

In a given embodiment, an apparatus includes a fabric layer, a cord of conductive thread overlying the fabric layer, and an electrode. A connector electrically interconnects the cord of conductive thread with the electrode. The connector has a passage in which the cord of conductive thread reaches through the connector. Additionally or alternatively, a non-conductive cap is received over the connector and retains the cord of conductive thread in contact with a surface of the connector.

In another embodiment, an apparatus is provided for use with an assistive device. The apparatus includes a fabric layer, an electrode supported on the fabric layer, and a housing having an open distal end. A body of molded material attaches the housing to the fabric layer. A conductive path reaches from the electrode into the housing. A processor is configured to process signals between the electrode and an assistive device when received in the housing in an installed position communicating with the conductive path. The processor is configured for insertion and removal through the open distal end of the housing.

In the illustrated examples, an apparatus is provided for use with a prosthetic socket and an assistive prosthetic device. The socket contains electrical contacts including a ground contact and signal contacts. The assistive prosthetic device communicates with the contacts in the socket.

The apparatus includes a prosthetic liner having an open proximal end for insertion of a residual limb. An electrode is supported on the liner to communicate electrically with the residual limb. A housing is fixed to the liner, and is receivable in the socket in an installed position. A processor is installed in the housing in communication with the electrode. Electrical signal contacts are exposed at a distal end of the housing for contacting the electrical signal contacts in the socket when the housing is in the installed position. Additionally, the housing defines a ground current path that communicates with the ground contact in the socket when the housing is in the installed position.

The housing may be fixed to the liner by a body of molded plastic material, and may be open at the distal end. The processor may be configured for insertion and removal through the open distal end of the housing. This enables the processor to be removed and retained for reuse when the liner needs to be replaced.

The electrical contacts in the housing may include ring-shaped contacts centered on an axis at the distal end of the housing. The corresponding contacts in the socket have radially spaced positions for contact with the ring-shaped contacts in any relative rotational orientation of the liner and the socket.

BRIEF DESCRIPTION OF THE DRAWINGS

FIGS. 8 and 9 depict conductive paths.

FIG. 16 is a sectional view taken on line 16-16 of FIG. 15.

FIG. 16A is a view similar to FIG. 16, showing an alternative configuration of the apparatus.

FIG. 17 depicts another alternative embodiment of a conductive human interface.

FIG. 17A is a view similar to FIG. 17, showing an alternative configuration of the apparatus.

FIG. 22 depicts the structure of FIG. 21 in different condition.

FIGS. 23-25 depict alternative embodiments of a conductor.

FIG. 26 depicts an alternative embodiment of an electrode connector.

FIG. 27 depicts the connector of FIG. 26 in connection with other parts.

DETAILED DESCRIPTION

Figure 1:
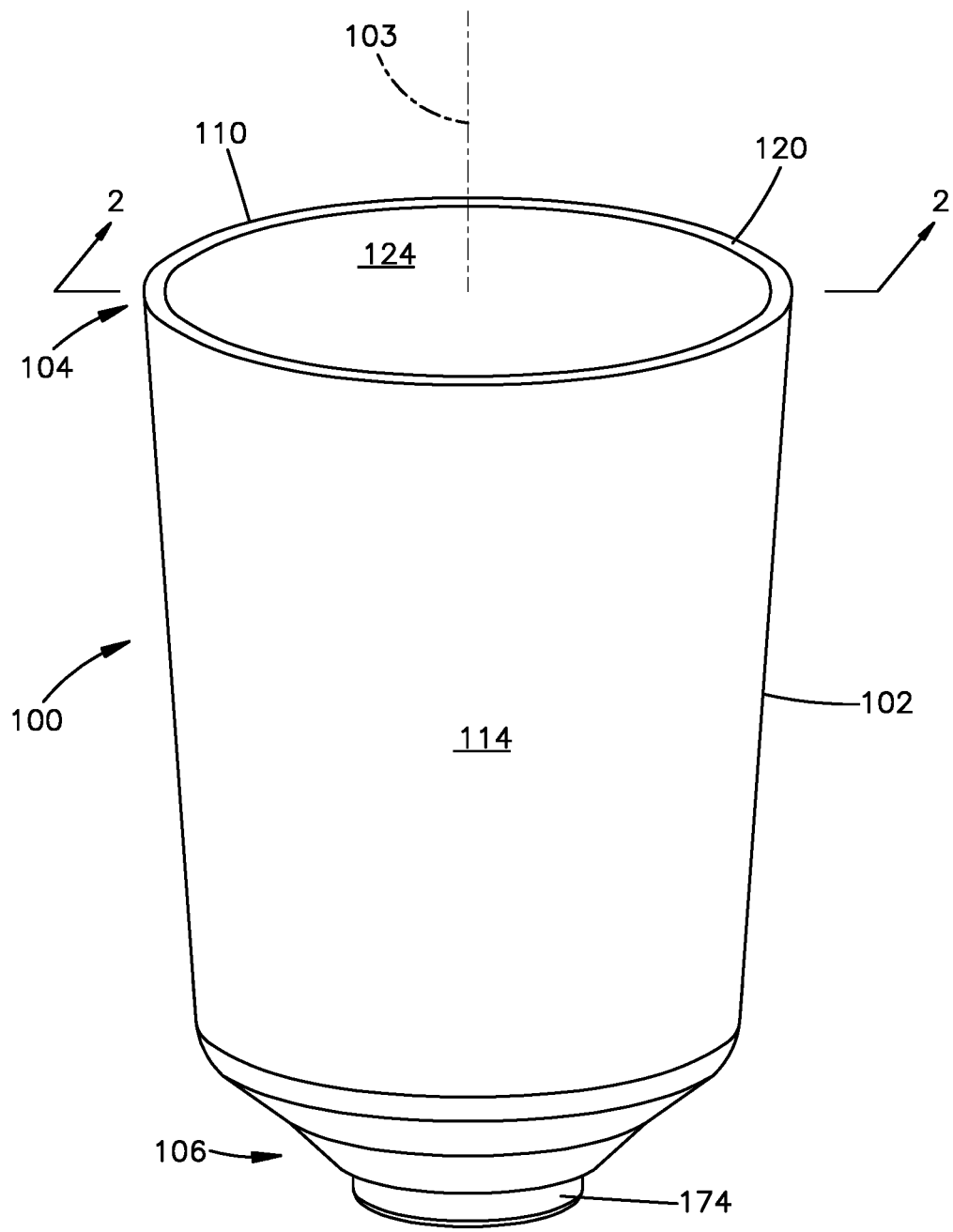
FIG. 1 depicts a conductive human interface.

The structures illustrated in the drawings include examples of the elements recited in the claims. The illustrated structures thus include examples of how a person of ordinary skill in the art can make and use the claimed invention. These examples are described to meet the enablement and best mode requirements of the patent statute without imposing limitations that are not recited in the claims. One or more elements of an embodiment may be used in combination with, or as a substitute for, one or more elements of another embodiment as needed for any particular implementation of the invention.

Figure 2:
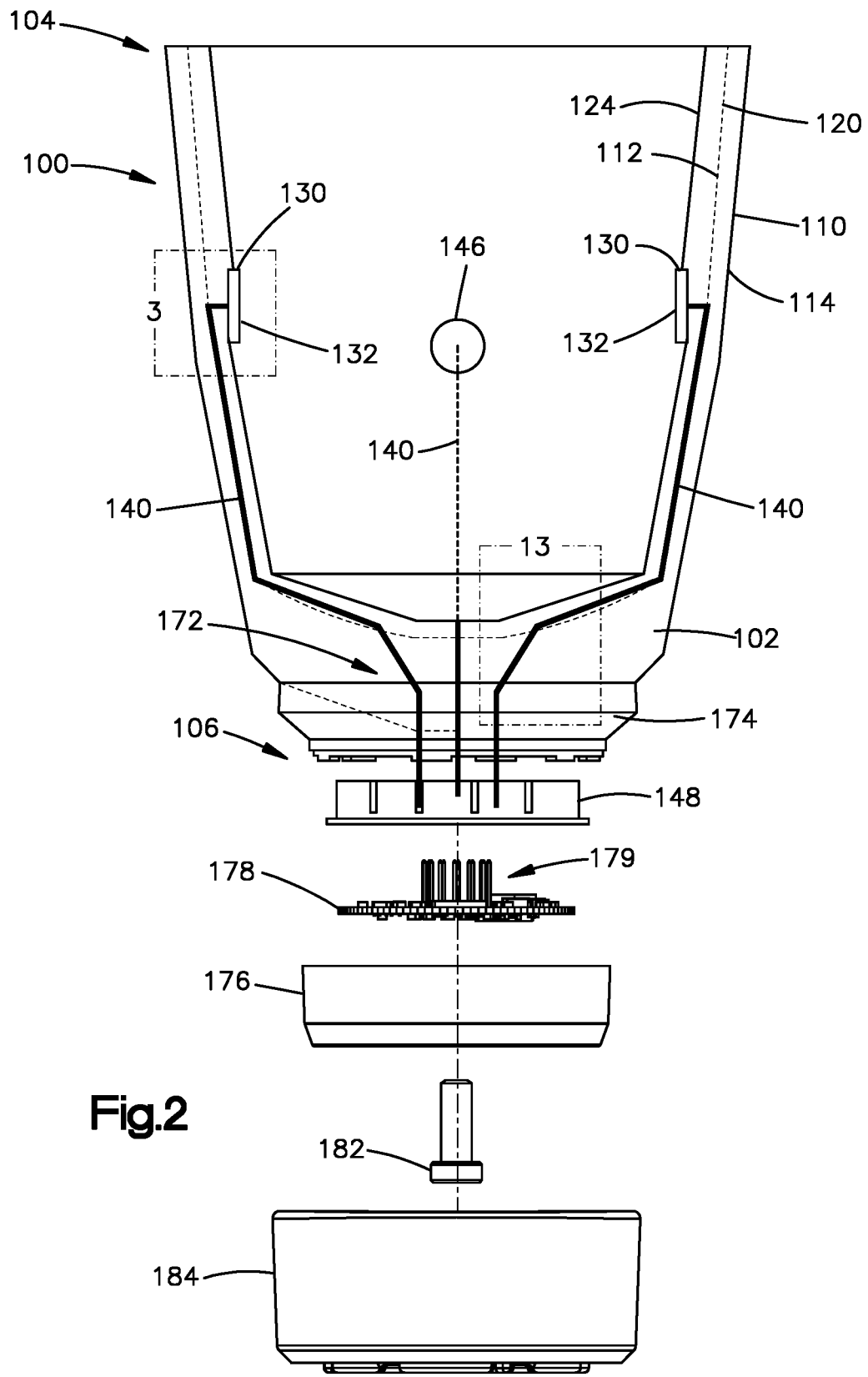
FIG. 2 depicts an exploded view of an interface system including a partial cross-sectional view of the conductive human interface of FIG. 1 along line 2-2.

Referring now to FIGS. 1 and 2, an embodiment of a conductive human interface 100 is schematically depicted. This example of a conductive human interface 100 is configured to capture electrical signals from the skin of a user and act as a physical interface with the user. In some embodiments, the conductive human interface 100 can also be configured to interface with an assistive device. The assistive device can be any device supplemental to the body of a user that cooperates with the neuromuscular and skeletal system of the user such as, for example, a prosthetic device (e.g., a prosthetic socket), an orthotic device, an exoskeletal device, a powered wheelchair, or the like. Accordingly, while certain embodiments of the present disclosure relate to a prosthetic liner 102 as shown in FIG. 1, the conductive human interface 100 can include the prosthetic liner 102, a sleeve, a band, a pad, or the like.

The conductive human interface 100 in the illustrated example includes a fabric layer 110 configured to form a flexible substrate. The fabric layer 110 can include one or more fabric materials such as, for example, stretch controlling fabrics, stretchable non-woven materials, fiber-on-end fabrics, or the like. Stretch-controlling fabric can be more stretchable in one direction than another direction. For example, a stretch-controlling fabric can have a limited stretch direction that is substantially orthogonal to a non-limited stretch direction. Accordingly, when the conductive human interface 100 includes a prosthetic liner 102, the stretch-controlling fabric can be oriented to permit greater stretch in a circumferential direction than in a longitudinal direction (i.e., along the length of the prosthetic liner 102 in the direction of the longitudinal axis 103).

Figure 3:
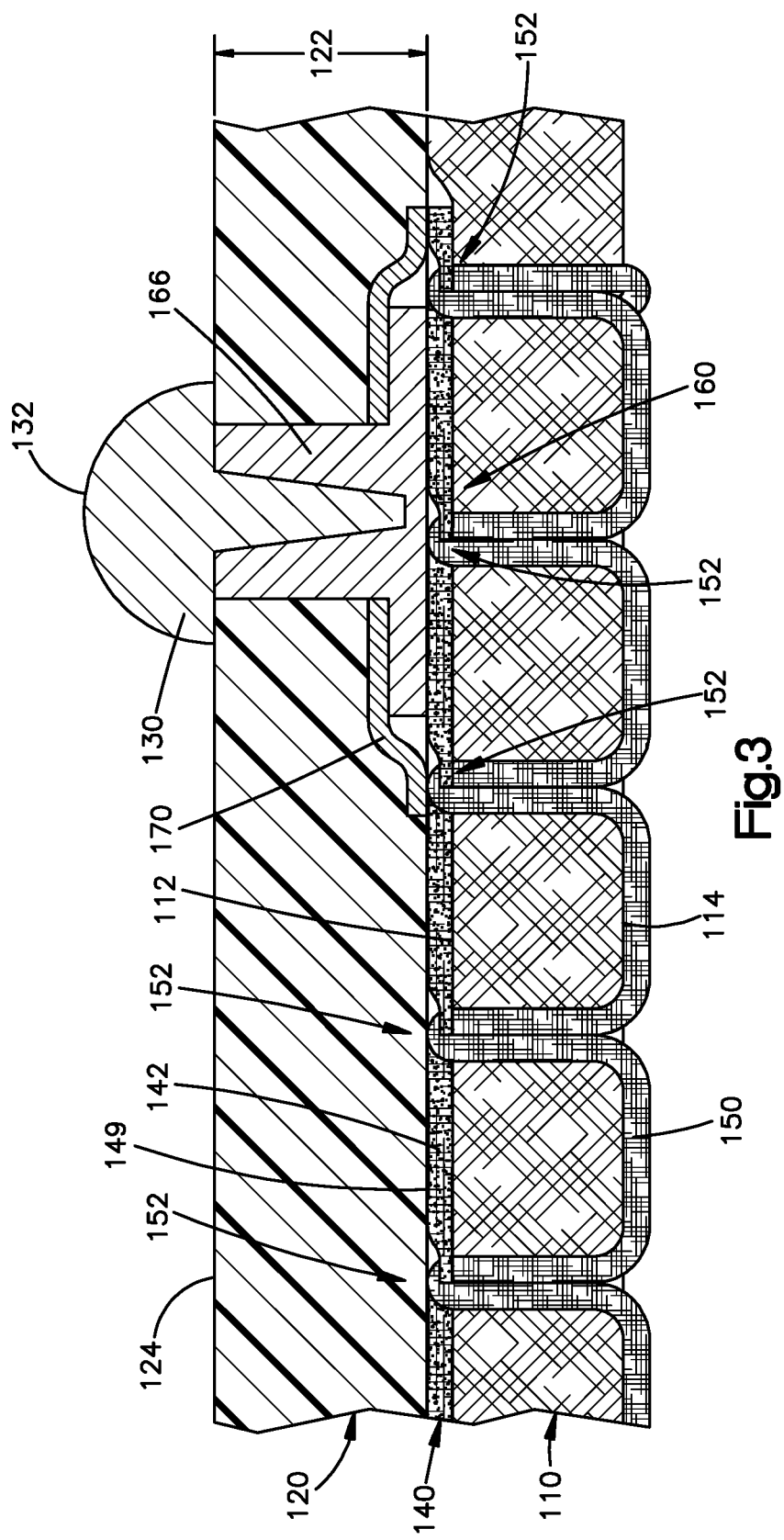
FIG. 3 is an enlarged partial view 3 of structure shown in FIG. 2.

Referring now to FIG. 3, the fabric layer 110 can include an interior surface 112 and an exterior surface 114. The interior surface 112 can form a boundary with a soft coating 120 configured for comfortable long term wear. The soft coating 120 can be formed from materials having a hardness on the Shore 00 scale such as, for example, a hardness of less than about 75 on the Shore 00 scale in one embodiment, or a hardness of between about 15-35 on the Shore 00 scale in another embodiment. Accordingly, the soft coating 120 can be formed from a soft polymer such as, for example, thermoplastic elastomers (TPE), silicones, block copolymers, urethanes, or the like. The thickness 122 of the soft coating 120, as measured from the interior surface 112 of the fabric layer 110 to the contact surface 124 of the soft coating 120, can be less than about 1 inch such as, for example, less than about 0.75 inches in one embodiment, or between about 0.150 and about 0.50 inches.

Referring to FIGS. 2 and 3, the conductive human interface 100 includes one or more electrodes 130 configured to make contact with the skin of the user and to receive EMG signals produced by muscles of the user. Generally, the electrodes 130 can be formed from conductive material such as, for example, metal or a polymeric material impregnated with conductive particles such as, for example, silicone impregnated with carbon particles. The electrodes 130 can be substantially even with the contact surface 124 of the soft coating 120 or protrude beyond the contact surface 124 of the soft coating 120. Each electrode 130 includes a detection surface 132 shaped to promote electrical contact with the skin of the user. For example, the detection surface 132 can be domed shaped, as shown for example in FIG. 3, or substantially flat, corrugated or any other shape or surface treatment that promotes electrical conductivity with the skin.

Referring to FIGS. 2-5, the conductive human interface 100 further includes a conductive path 140 for electrically connecting each electrode 130 to another component. As used herein, the phrase "electrically connect" means to provide a medium for the transmission of electrical signals from one object to another object. The conductive path 140 generally includes a flexible conductor such as, for example, conductive thread 142 (FIG. 3), conductive fabric 144 (FIG. 4), a conductive ink 145 (FIG. 5), or combinations thereof.

A section 149 of each conductor 142, 144, or 145 overlies the interior surface 112 of the fabric layer.

The conductive thread 142 (FIG. 3) is configured as a cord with either a monofilament structure or a multi-filament structure. A conductive filament can be formed of a conductive material, such as stainless steel, and alternatively could be formed of a non-conductive substrate material that is coated or embedded with electrically conductive elements such as, for example, silver, carbon, nickel, copper, gold, titanium, or the like. Substrates can include cotton, polyester, nylon, aramids, or the like. A multi-filament structure can be formed from a plurality of conductive filaments that are bundled, spun or twisted together into a substantially cord-like shape, and may include non-conductive filaments. In some embodiments, the conductive thread 142 can be formed from multiple plys of thread that are spun or twisted together into a substantially cord-like shape such as, for example, 2 plys in one embodiment, or 4 plys in another embodiment. The conductive thread 142 can be characterized by linear resistance. In some embodiments, the conductive thread 142 can have a linear resistance of less than about 10 $\Omega$/in such as, for example, less than about 6 $\Omega$/in in one embodiment, between about 0.5 $\Omega$/in to about 3.5 $\Omega$/in in another embodiment. The conductive thread 142 can also be characterized by linear density. In some embodiments, the conductive thread 142 can have a linear density of at least about 2,000 yd/lb such as, for example, between about 3,000 yd/lb and about 9,500 yd/lb in one embodiment, between about 3,500 yd/lb and about 4,000 yd/lb in another embodiment, or between about 8,500 yd/lb and about 9,000 yd/lb in another embodiment.

In distinction from the cord of the conductive thread 142, the conductive fabric 144 (FIG. 4) can be a substantially sheet like material formed from a plurality of conductive filaments or conductive threads 142 that are woven, knitted, or bonded together via chemical, mechanical, heat or solvent treatments. The conductive ink 145 (FIG. 5) can be a conductive body formed from a conductive liquid that has been dried, cured, cooled or a combination thereof. The conductive ink 145 can include electrically conductive elements, as described above, suspended within a substrate (e.g., polymer film).

Referring again to FIG. 2, the conductive human interface 100 can include one or more sensors 146 configured to detect physical characteristics of the conductive human interface 100, the skin of the user, or both. The one or more sensors 146 can be electrically connected to the conductive path 140 in a manner similar to the electrical connection of the electrodes 130, as described in greater detail below. It is noted that the term "sensor," as used herein, can mean a device that measures a physical quantity and converts it into an electrical signal, which is correlated to the measured value of the physical quantity. A sensor 146 can thus comprise a temperature sensor, a moisture sensor, a gyroscope, shear sensor, pressure sensor, force sensor (e.g., normal force, sliding force), distance sensor, or combinations thereof. At least a portion of the one or more sensors can be embedded within the soft coating 120. Alternatively or additionally, the sensor 146 can include a power source, processor, or both located external to the conductive human interface 100. For example, the components of the sensor 146 can be electrically connected via the conductive path 140.

Figure 7:
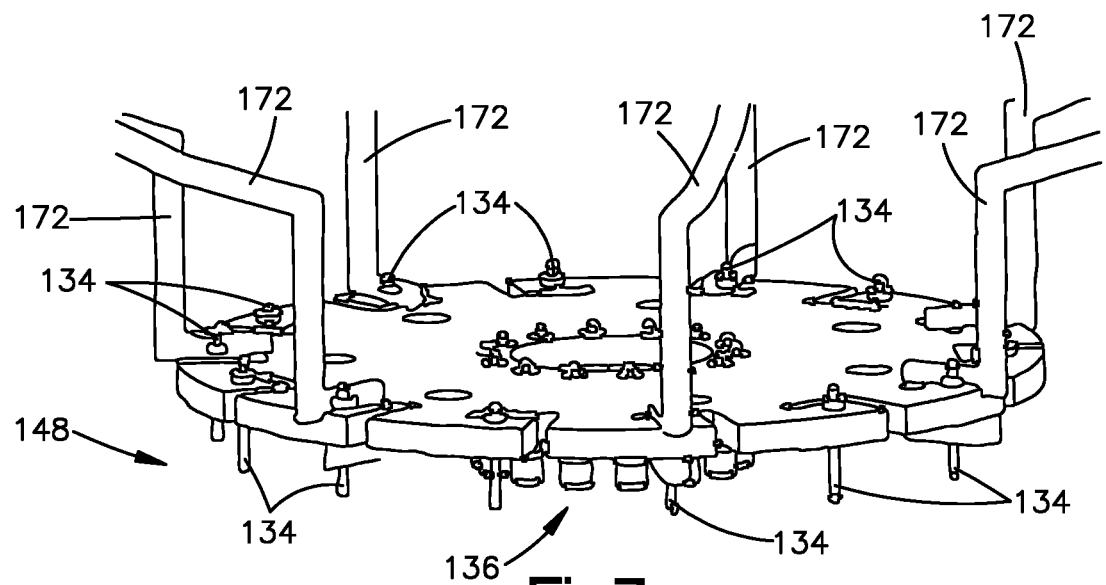
FIG. 7 is a perspective view an electrical connector.

Referring to FIGS. 2 and 7, the conductive human interface 100 can include an electrical connector 148 configured to electrically connect each conductive path 140 with another component. The electrical connector 148 can include conductive members 134 (FIG. 7), each of which is configured to be electrically connected to one of the conductive paths 140. Specifically, a conductive member 134 can include features configured to provide a mechanical connection with fabric or thread. For example, the conductive member 134 can include a feature that promotes a knotted connection such as, but not limited to, a slot (e.g., "L" shaped slot), a boat cleat shaped member, a knob, a hook, orifices, or the like. Accordingly, an electrical connection can be formed by wrapping a portion (e.g., a connector lead 172) of the conductive path 140 around the conductive member 134, tying the portion of the conductive path 140 to the conductive member 134 or combinations thereof. In some embodiments, the electrical connector 134 can be configured to transition from relatively flexible conductors to more rigid conductors. For example, the electrical connector 148 can include a separable electrical connector 136 (e.g., pins, sockets, etc.) electrically connected to the conductive members 134.

Referring to FIGS. 2 and 3, a method for forming the conductive human interface 100 can include providing the fabric layer 110 in the desired shape such as, for example, as a panel, a tube, or a sock. In embodiments where the fabric layer 110 is shaped into a sock (FIG. 2), the conductive human interface 100 can be provided as a prosthetic liner 102 configured to serve as an interface between a residual limb and a prosthetic socket. Accordingly, the prosthetic liner 102 can extend between an open end 104 and a closed end 106.

The conductive path 140 can be attached to the fabric layer 110. In embodiments where the conductive path 140 includes conductive thread 142, the conductive thread 142 can be stitched to the fabric layer 110 using a support thread 150 (FIG. 3), which can be non-conductive. For example, one of the conductive thread 142 and the support thread 150 can be provided in the thread feed of a sewing machine, and the other can be provided in the bobbin. Accordingly, a majority of the conductive thread 142 can be located on the interior surface 112 of the fabric layer 110. Additionally, a majority of the support thread 150 can be located on the exterior surface 114 of the fabric layer 110.

The tension applied at each of the needle punctures 152 through the fabric layer 110 can be controlled to improve the flexibility of the conductive path 140. For example, flexibility of the conductive path 140 can be improved by having the support thread 150 loop around the conductive thread 142 inwards above the interior surface 112 of the fabric layer 110 as shown, for example, in FIG. 3. That is, the support thread 150 can be pushed completely through the fabric layer 110 and separated from the interior surface 112 of the fabric layer 110 by the conductive thread 142 at the needle puncture 152. Accordingly, the conductive thread 142 can be held to the interior surface 112 of the fabric layer 110 by the support thread 150, which can be provided both on the interior surface 112 and the exterior surface 114 of the fabric.

Referring to FIGS. 8 and 9, in embodiments where the conductive path 140 includes conductive thread 142, the durability of the conductive path 140 can be improved by controlling the aspect ratio along the conductive path 140. The aspect ratio can be determined by dividing a width 154 between adjacent needle punctures 152 by a length 156 between the adjacent needle punctures 152. Preferably, the aspect ratio can be greater than about 1 such as, for example, greater than about 1.1 in one embodiment, greater than about 1.25 in another embodiment, or about 1.5 in a further embodiment. Generally, the length 156 refers to a direction substantially parallel to the overall direction in which the conductive path 140 is elongated between its opposite ends, and the width 154 refers to a direction substantially orthogonal to the length. Further improvements can be provided by aligning the length 156 between punctures 152 along the length of the prosthetic liner 102. In embodiments where the conductive thread 142 is stitched with a machine, the direction the fabric layer 110 is fed through the machine can define the direction of the conductive path 140.

The conductive thread 142 can include a span 158 (FIG. 8) formed between an electrode patch 160 and a connector patch 162. The electrode patch 160 and the connector patch 162 can be configured to anchor the conductive path 140. In some embodiments, the aspect ratio of the conductive thread 142 at the electrode patch 160 and the connector patch 162 can be greater than the aspect ratio of the conductive thread 142 of the span 158. For example, the aspect ratio of the conductive thread 142 at the electrode patch 160 and the connector patch 162 can be at least twice as large as the aspect ratio of the conductive thread 142 of the span 158 such as, for example, at least about four times as large.

Additionally, manufacturability of the conductive human interface 100 can be improved by overlapping multiple layers of the conductive thread 142 at the electrode patch 160, the connector patch 162, or both. For example, the layers can be overlapped to form a patch 160 or 162 by taking multiple passes over the same location. In embodiments where the conductive thread 142 is stitched with a machine, the feed direction can be reversed back and forth over the location of the electrode patch 160, the connector patch 162, or both to provide the number of layers desired to form the patch 160 or 162 at that location. Additionally, changing the feed direction can cause the conductive thread 142 to self-knot or self-entangle, which can improve the overall durability of the conductive path 140 and reduce manufacturing time. Accordingly, the electrode patch 160, the connector patch 162, or both can include more layers than the span 158. In some embodiments, the electrode patch 160 can include a greater number of layers of the conductive thread 142 than the connector patch 162.

Figure 4:
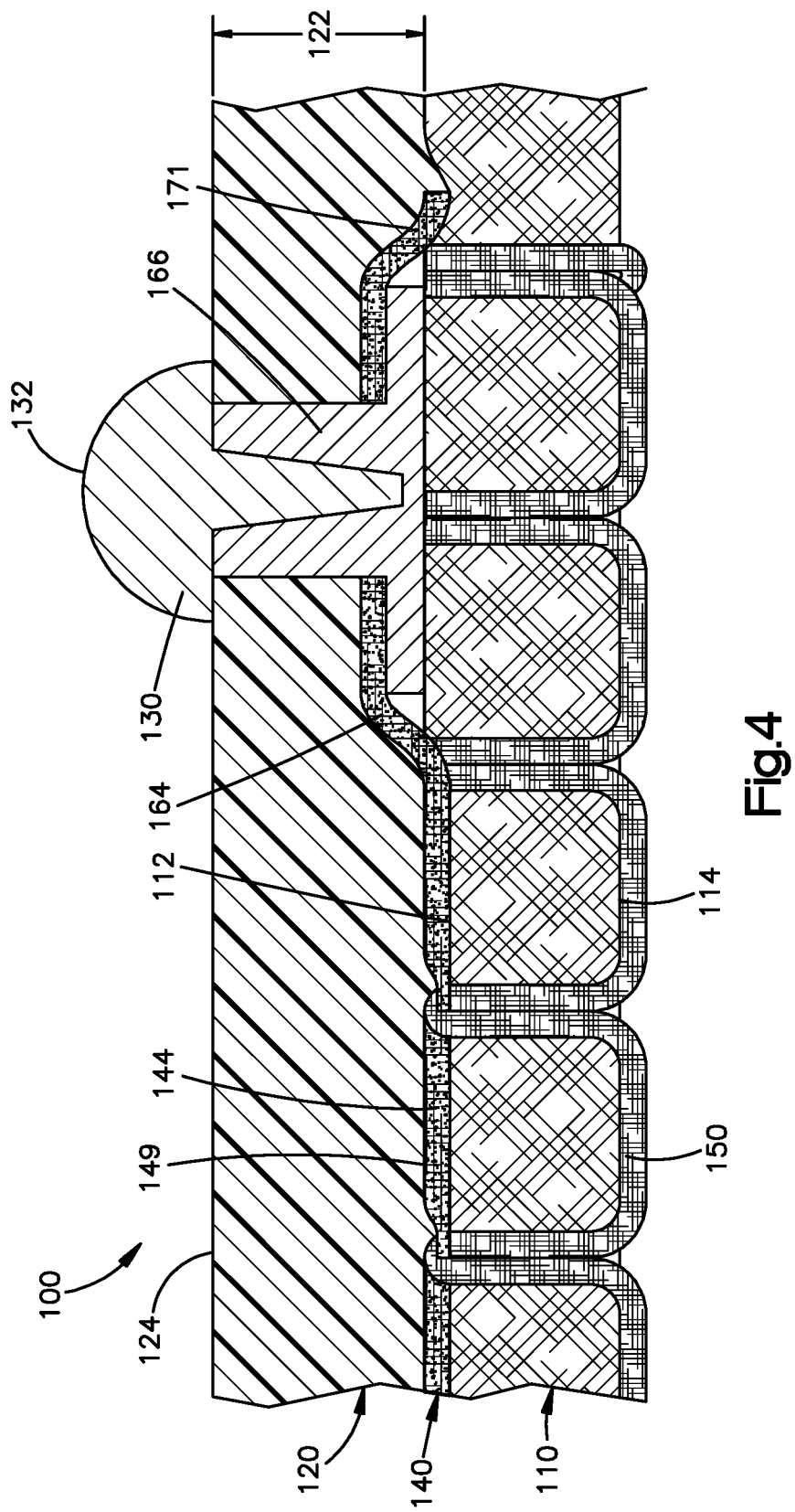
FIGS. 4 and 5 depict alternative embodiments of the structure shown in FIG. 3.
Figure 6:
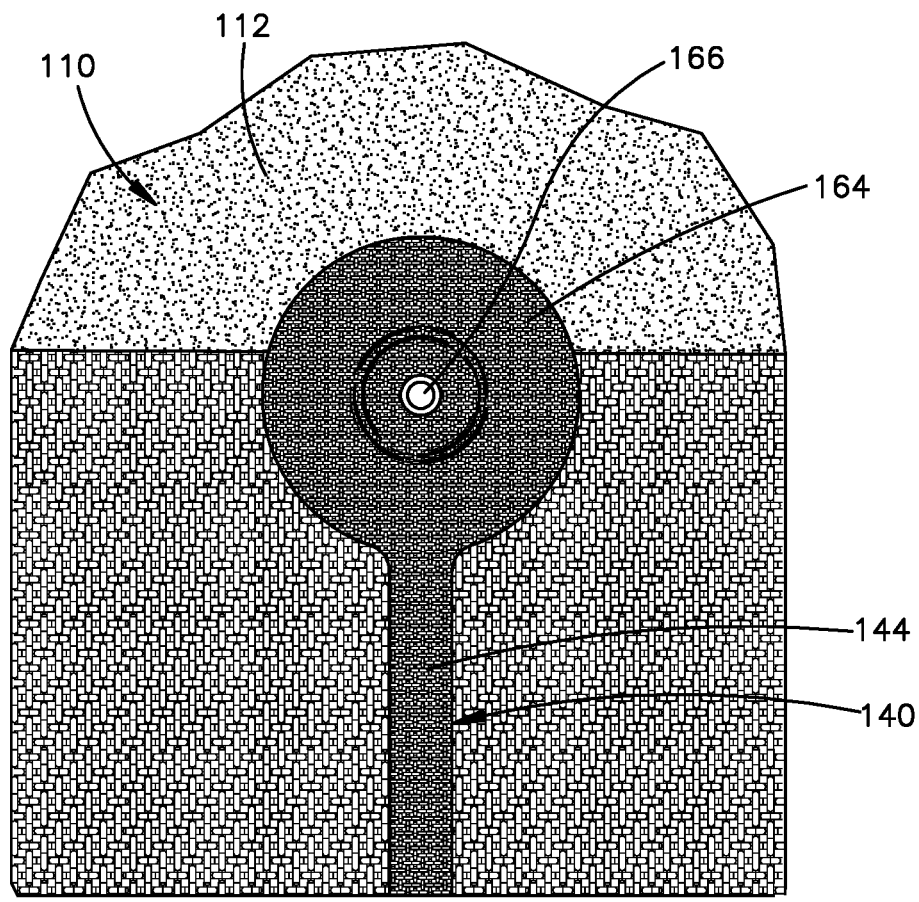
FIG. 6 is an enlarged partial view of the conductive human interface of FIG. 2.

Referring to FIGS. 4 and 6, in embodiments where the conductive path 140 includes conductive fabric 144, the conductive fabric 144 can be attached to the interior surface 112 of the fabric layer 110 such as, for example, with adhesive, stitching, or the like. In some embodiments, the conductive fabric 144 can be cut to a shape that is configured to extend between an electrode 130 and the electrical connector 148. Alternatively, the conductive fabric can be cut to a shape that is configured to extend between an electrode 130 and the processing board 178. The shape of the conductive fabric 144 can include an electrode portion 164 configured to be attached to the electrode 130. Accordingly, the electrode portion 164 can be correspondingly shaped to the electrode 130. In embodiments where the conductive path 140 includes conductive ink 145, the conductive ink 145 can be applied directly to the interior surface 112 of the fabric layer 110.

Referring to FIGS. 3-6 and 9-10, a method for forming the conductive human interface 100 can include electrically connecting an electrode connector 166 to the conductive path 140. The electrode connector 166 can be formed from conductive materials such as, for example, a metal (e.g., copper, aluminum, gold, silver, etc.), a graphite material, or a conductive polymer. In embodiments where the conductive path 140 includes conductive thread 142, the electrode patch 160 can be configured to electrically connect with the electrode connector 166. For example, the conductive thread 142 of the electrode patch 160 can define a conductive region at the interior surface 112 of the fabric layer 110 for promoting electrical contact with the electrode connector 166.

Additionally, the electrode connector 166 can be configured to mechanically connect to the conductive path 140 and the electrode 130. The electrode connector 166 can include one or more features that promote a knotted connection, as described above, with an electrode lead 168 (FIGS. 8 and 9) extending from the electrode patch 160. Accordingly, the electrode lead 168 can be wrapped or tied to the features of the electrode connector 166, which can improve the contact between the electrode connector 166 and the electrode patch 160.

Figure 10:
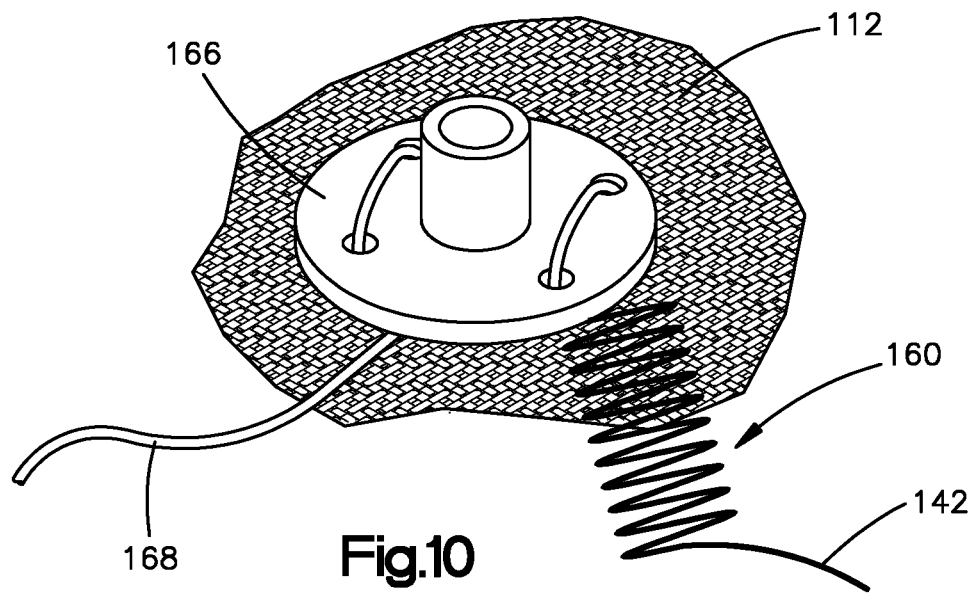
FIGS. 10-11 depict an electrode connector and a conductive path.

Alternatively or additionally, a fabric patch 170 can be used to provide a mechanical connection between the electrode connector 166 and the electrode patch 160, as best shown in FIG. 10. In some embodiments, the fabric patch 170 can cover the electrode connector 166 and can be adhered to the interior surface 112 of the fabric layer 110. Accordingly, the electrode connector 166 can be positioned between the fabric patch 170 and the interior surface 112 of the fabric layer 110 as shown in FIG. 3. Moreover, the fabric patch 170 can be configured to isolate the electrical connection between the electrode patch 160 and the electrode connector 166 from the soft coating 120. For example, when the fabric patch 170 is applied before the soft coating 120, undesired intrusion of the soft coating 120 between the electrode connector 166 and the electrode patch 160 can be mitigated. Accordingly, the mechanical and electrical connection can be improved.

Referring to FIGS. 4 and 6, in embodiments where the conductive path 140 includes conductive fabric 144, the electrode connector 166 can be electrically and mechanically connected with the electrode portion 164 of the conductive fabric 144. For example, the electrode portion 164 can partially cover the electrode connector 166 and extend beyond the electrode connector 166. The overhanging portion 171 of the electrode portion 164 can be adhered to the interior surface 112 of the fabric layer 110. Thus, the electrode connector 166 can be positioned between the electrode portion 164 of the conductive fabric 144 and the interior surface 112 of the fabric layer 110.

Figure 5:
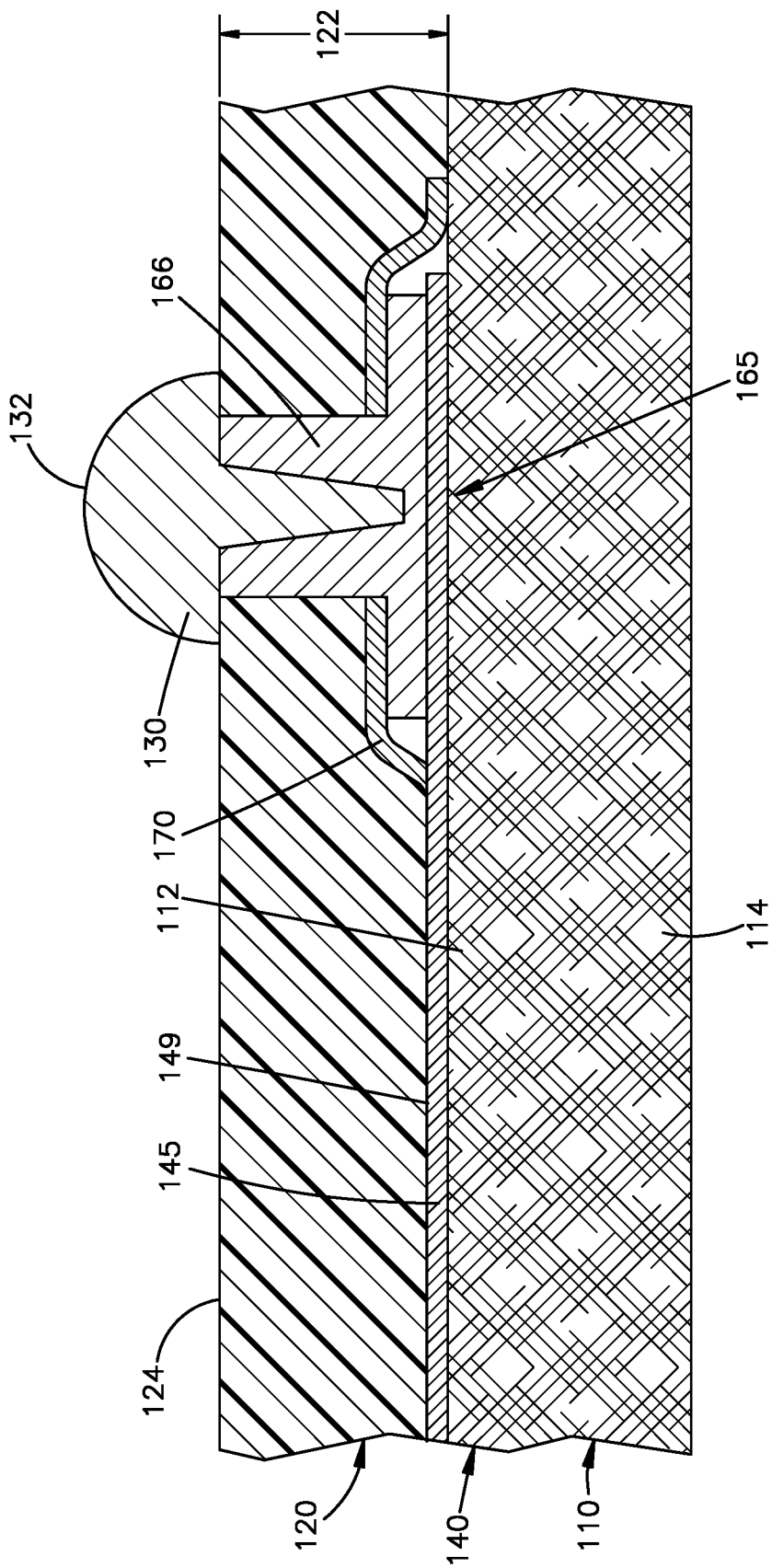

Referring to FIGS. 2 and 5, in embodiments where the conductive path 140 includes conductive ink 145, the electrode connector 166 can be electrically and mechanically connected with the electrode portion 165 of the conductive ink 145. For example, the electrode portion 165 can be applied directly to the interior surface 112 of the fabric layer 110 such that the electrode portion 165 is at least as large as the electrode connector 166. The conductive ink 145 can be cured prior to connecting with the electrode connector 166. Alternatively, the electrode connector 166 can be connected to the electrode portion 165, while the conductive ink 145 is in an uncured state. Accordingly, the curing process can contribute to the quality of the connection therebetween. Alternatively or additionally, the fabric patch 170 can be used to isolate and improve the mechanical connection and the electrical connection between the electrode connector 166 and the electrode portion 165, as noted above. Specifically, the electrode connector 166 can be positioned between the fabric patch 170 and the electrode portion 165 of the conductive ink 145. Additionally, the fabric patch 170 can substantially cover the electrode portion 165, such that the fabric patch 170 is adhered to the interior surface 112 of the fabric layer 110 around the electrode portion 165.

Figure 11:
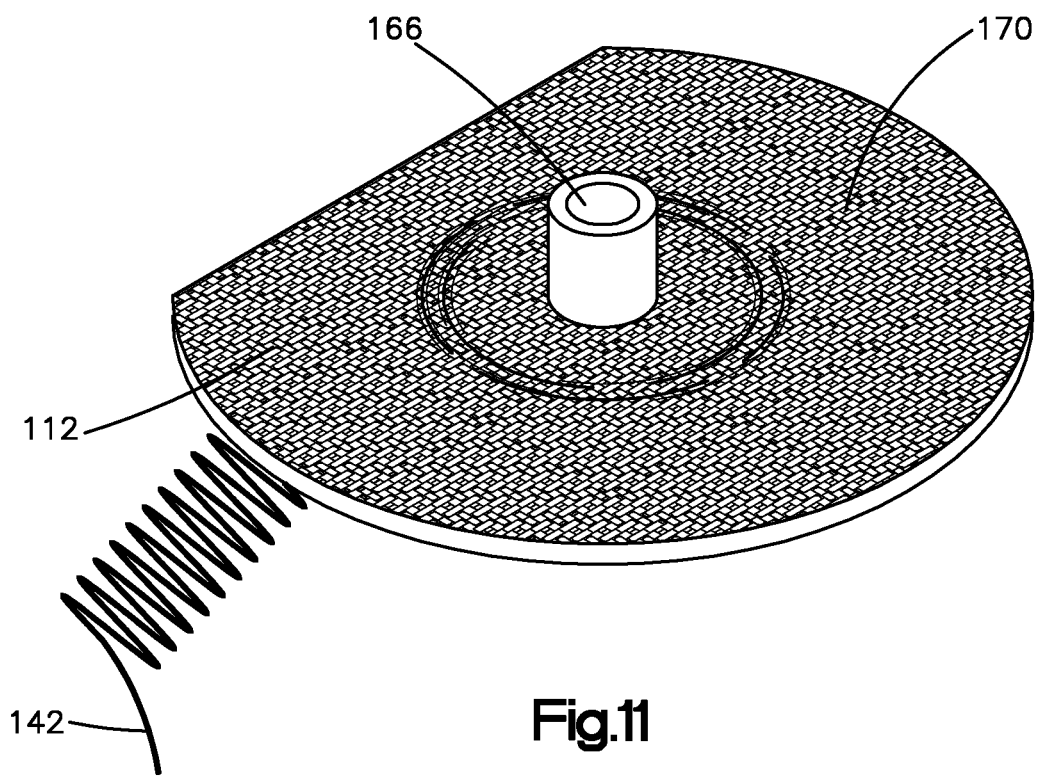
Figure 12:
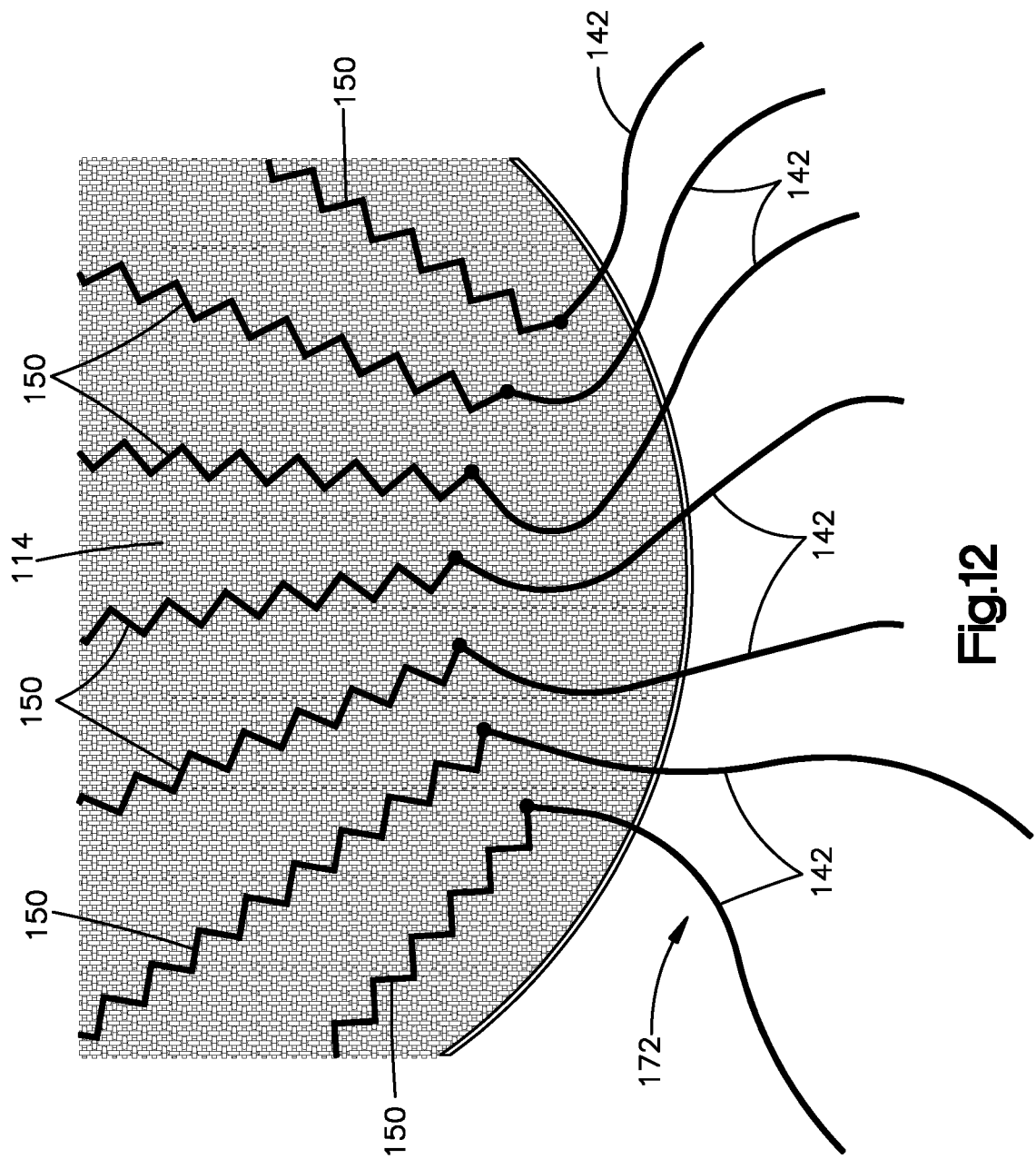
FIG. 12 depicts a closed end of a fabric layer.
Figure 13:
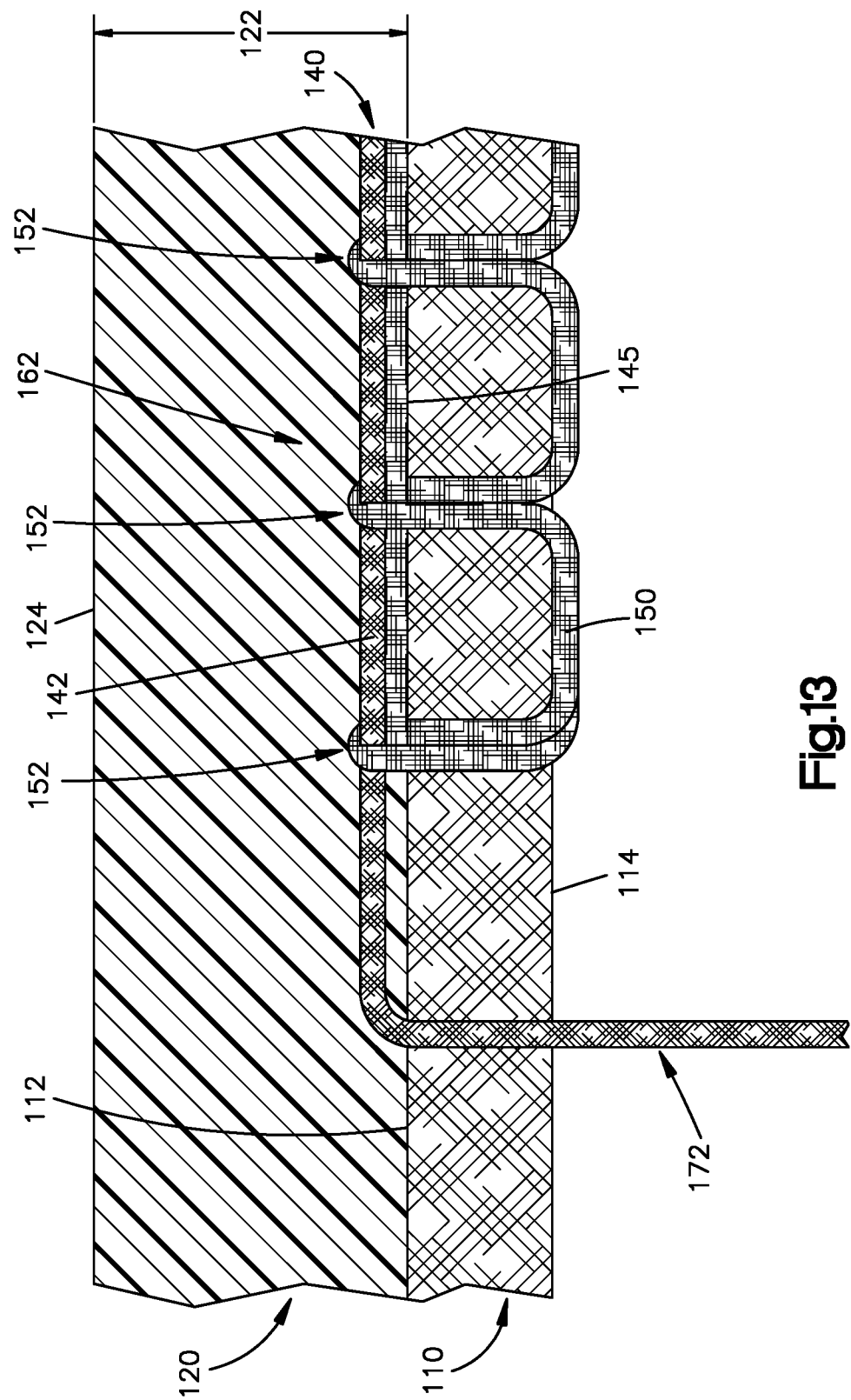
FIG. 13 depicts an alternative embodiment of the structures shown in FIGS. 3-5.
Figure 15:
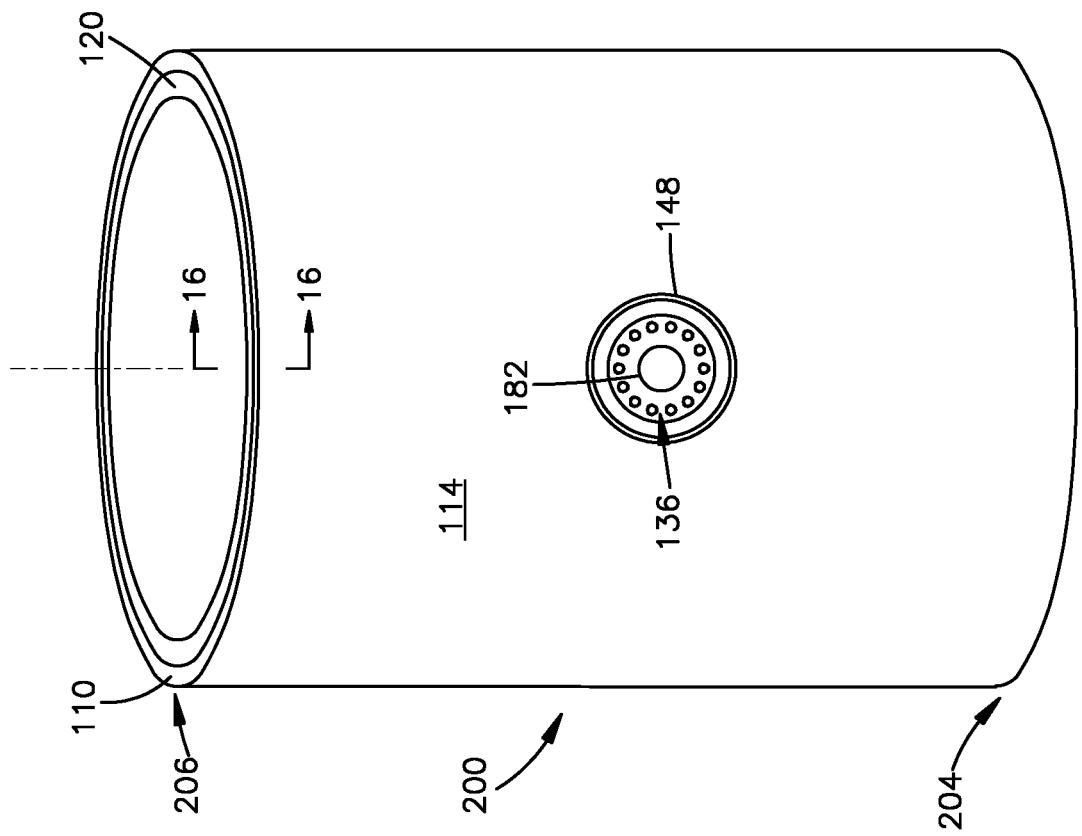
FIG. 15 depicts an alternative embodiment of a conductive human interface.

Referring to FIGS. 11 and 12, a method for forming the conductive human interface 100 can include arranging connector leads 172 with respect to the fabric layer 110. In some embodiments, the conductive path 140 can include connector leads 172 that extend beyond the exterior surface 114 of the fabric layer 110. The connector leads 172 can be formed from the conductive thread 142, the conductive fabric 144, conductive ink 145 applied to a non-conductive fabric, or combinations thereof. A connector lead 172 can extend from the connector patch 162 and through one or more orifices in the fabric layer 110 as shown, for example, in FIG. 13. For example, in embodiments where the conductive human interface 100 includes the prosthetic liner 102, the connector leads 172 can extend through the fabric layer 110 at the closed end 106.

In embodiments where the conductive path 140 includes conductive ink 145, the conductive ink 145 can be electrically connected to the connector lead 172 at the connector patch 162. For example, the conductive ink 145 can be applied to the interior surface 112 of the fabric layer 110. After the conductive ink 145 is applied, the connector patch 162 can be stitched upon the conductive ink 145 with the conductive thread 142. Accordingly, each of the needle punctures 152 can be formed through the conductive ink 145 and the connector lead 172 can be formed with conductive thread 142. In embodiments where the connector lead 172 is formed of the conductive fabric 144 or the conductive ink 145 applied to a non-conductive fabric, the connector lead 172 can be applied over the conductive ink 145 and the fabric of the connector lead 172 can be adhered to the interior surface 112 of the fabric layer 110. Accordingly, the conductive ink 145 can be positioned between the connector lead 172 and the interior surface 112 of the fabric layer 100.

In alternative embodiments, the conductive ink 145 can be applied over the connector lead 172, i.e., the connector lead 172 can be positioned between the conductive ink 145 and the interior surface 112 of the fabric layer 100. For example, the connector lead 172 can be formed from conductive thread 142 and the conductive ink 145 can be applied over the connector patch 162. In embodiments where the connector lead 172 is formed of the conductive fabric 144 or the conductive ink 145 applied to a non-conductive fabric, the conductive ink 145 can be applied over the connector lead 172.

In a method for forming the conductive human interface 100, the soft coating 120 can be applied in a gel state and cured within a mold to form the soft coating 120. In some embodiments, the soft coating 120 can be applied after the conductive path 140 is formed upon the fabric layer 110. Accordingly, the conductive path 140 can be covered by or embedded within the soft coating 120. In embodiments, where the connector leads 172 extend through the fabric layer 110, the orifices in the fabric layer 110 can be sized such that the connector leads 172 are compressed by the fabric layer 110. For example, each orifice can be smaller than the connector leads 172 that pass through the orifice. Thus, the orifices can be configured to mitigate permeation of the soft coating 120.

The electrode connector 166 can include one or more features that promote a mechanical connection with the electrode 130 such as, for example, a threaded connection, a friction fit, a clamping feature, a pin connector, a socket connector, or the like. Thus, while the electrode connector is depicted in FIG. 6 as a metal tee nut, the embodiments provided herein are not so limited. Accordingly, the electrode 130 can be connected to the electrode connector 166 after the soft coating 120 is applied to the fabric layer 110.

The electrode connector 166 can be configured to protrude away from the interior surface 112 of the fabric layer 110. For example, the feature for connecting with the electrode 130 can be offset from the interior surface 112 of the fabric layer 110. In embodiments with the fabric patch 170, the feature for connecting with the electrode 130 can protrude through the fabric patch 170. Accordingly, the electrode connector 166 can at least partially extend through the soft coating 120 and can mate with the electrode 130 after the soft coating 120 is applied to the fabric layer 110.

In embodiments where the electrodes 130 are formed from polymeric materials, the electrodes 130 can be applied directly to the conductive path 140 (e.g., the electrode patch 160, the electrode portion 164, or the electrode portion 165). Accordingly, the electrodes 130 can make surface contact with the conductive path 140 or both the conductive path 140 and the interior surface 112 of the fabric layer 110. In some embodiments, the polymeric material can be applied directly to the conductive path 140 in a gel state and cured to form the electrode 130. The direct contact allows for the electrode connector 166 to be omitted in certain embodiments. In some embodiments, the polymeric material of the electrodes 130 can be applied before the soft coating 120 is applied. Alternatively, the polymeric material of the electrodes 130 can be applied after the soft coating 120 is applied. For example, a removable body can cover the electrode sites on the conductive path 140, while the soft coating 120 is applied. The removable body can then be removed to allow the polymeric material of the electrodes 130 to be applied to the electrode sites.

Referring to FIGS. 2 and 7, a method for forming the conductive human interface 100 can include electrically connecting the conductive path 140 to the electrical connector 148. Specifically, each of the connector leads 172 can be electrically and mechanically connected to one of the conductive members 134 as shown, for example, in FIG. 7. Accordingly, the signals can be communicated by each of the conductive paths 140 to an assistive device in communication with the separable electrical connector 136.

Referring again to FIGS. 1, 2 and 2A, the prosthetic liner 102 can include an umbrella 174 formed at the closed end 106 and external to the exterior surface 114 of the fabric layer 110. In some embodiments, the umbrella 174 can be formed around the electrical connector 148. Alternatively, the umbrella 174 may be molded around a processing board 178 directly connected to a conductive path 140. For example, the umbrella 174 can be molded to the exterior surface 114 of the fabric layer 110 out of relatively hard materials such as, for example, a hard urethane. Accordingly, the connector leads 172 can extend through the fabric layer 110 at the closed end 106 of the prosthetic liner 102 above the umbrella 174.

Figure 2A:
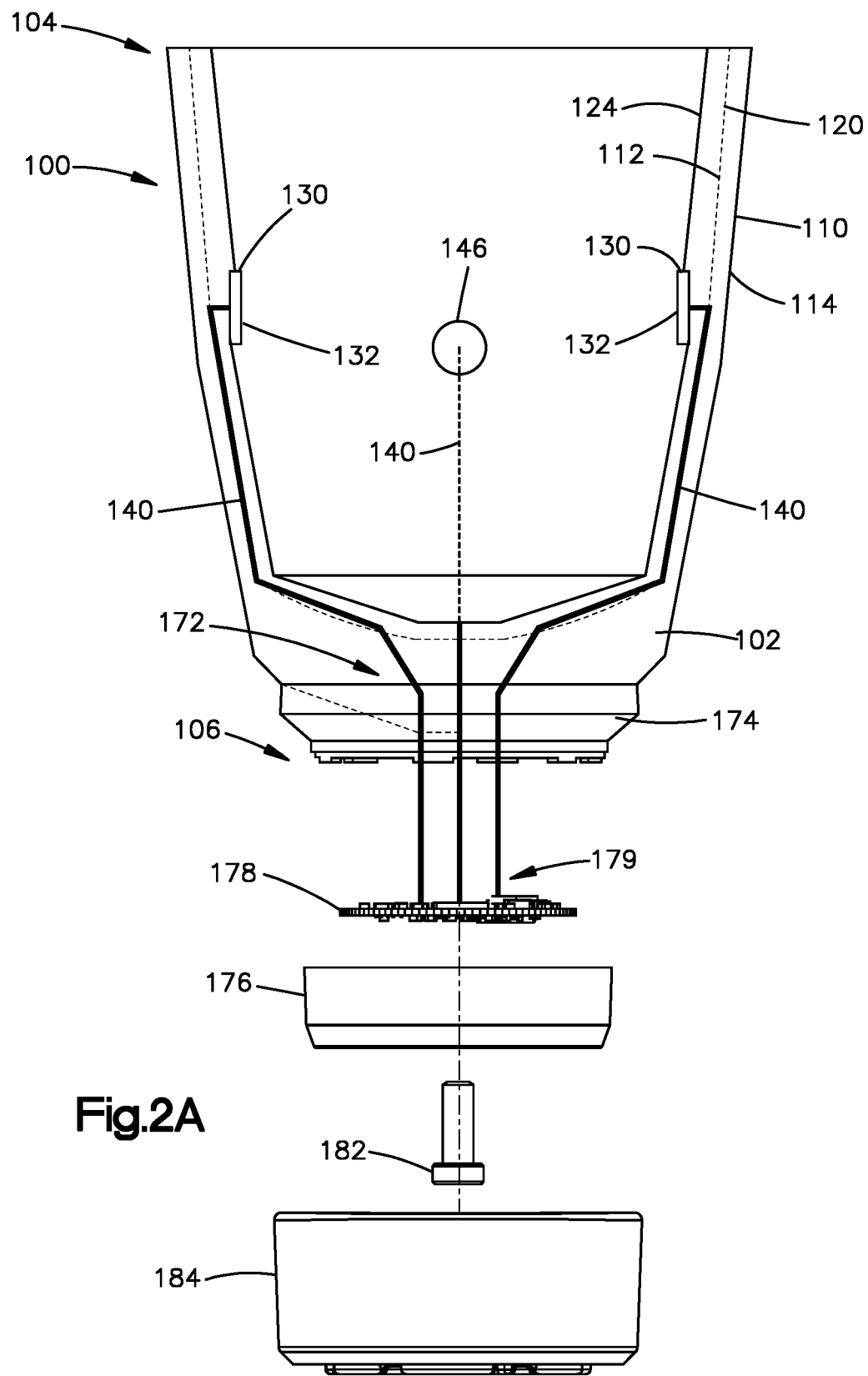
FIG. 2A is a view similar to FIG. 2, showing an alternative configuration of the apparatus.
Figure 14:
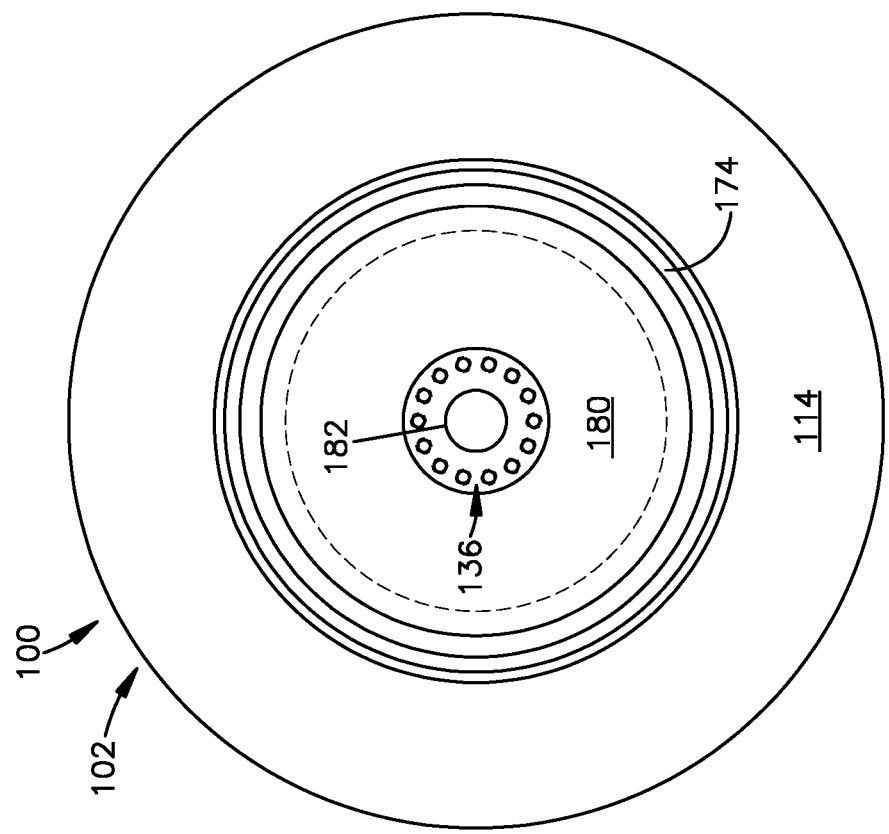
FIG. 14 depicts an umbrella of a liner.
Figure 15A:
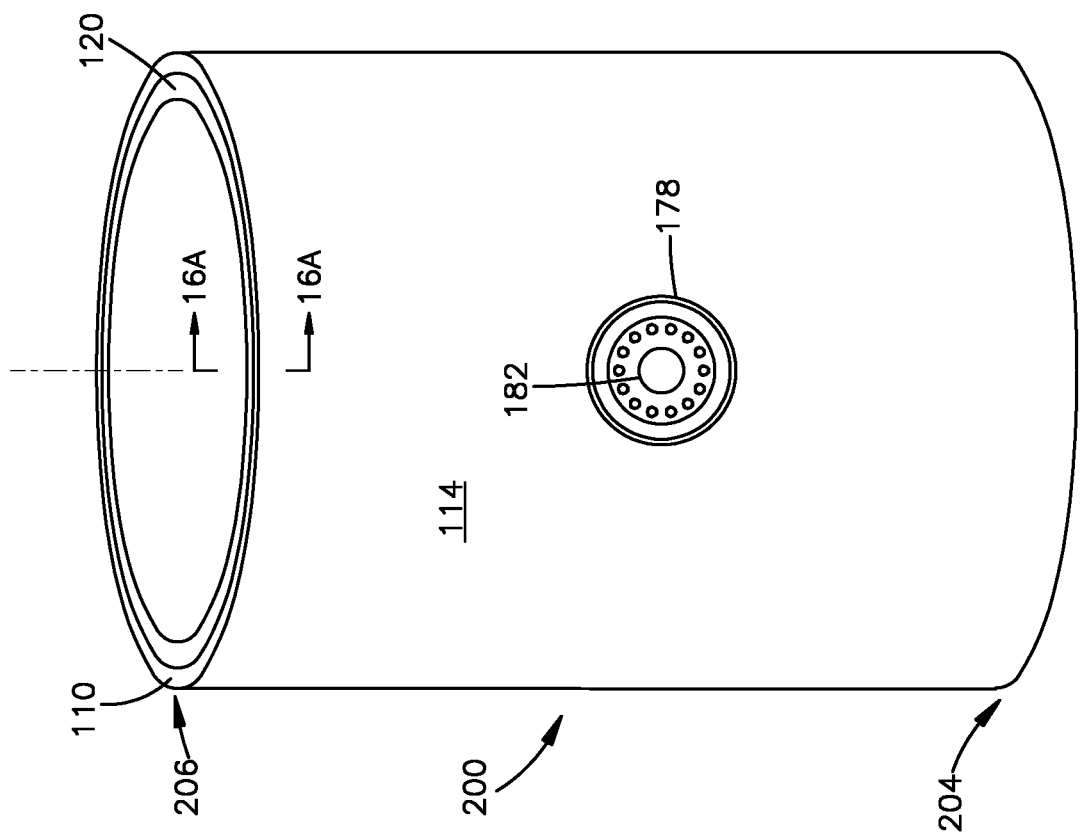
FIG. 15A is a view similar to FIG. 15, showing an alternative configuration of the apparatus.
Figure 14A:
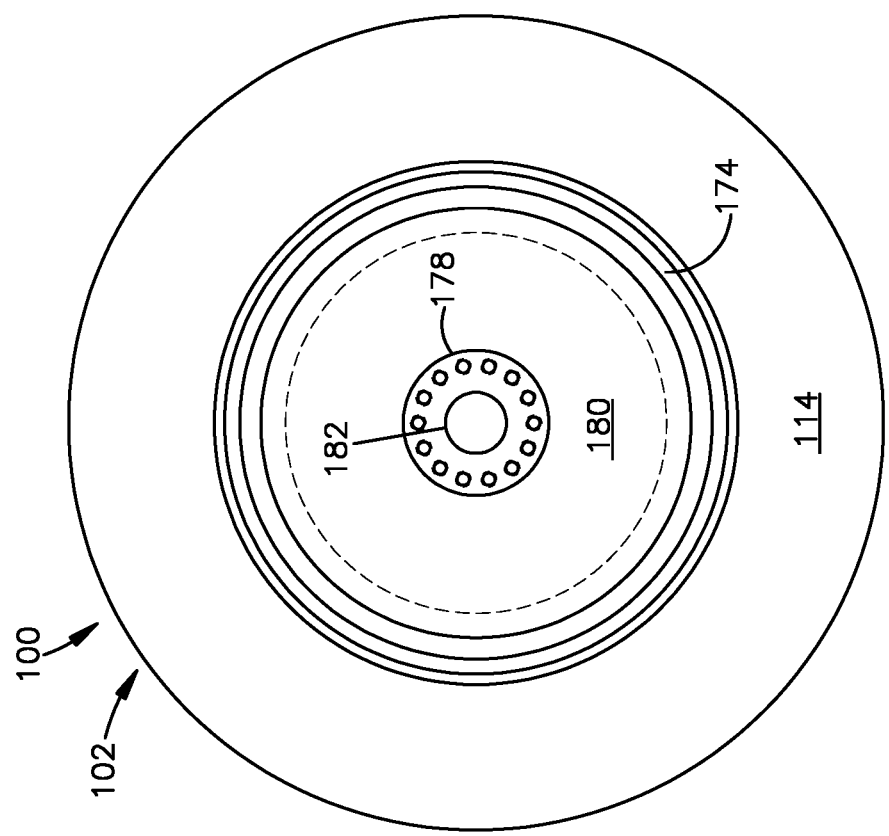
FIG. 14A is a view similar to FIG. 14, showing an alternative configuration of the apparatus.

The umbrella 174 can be configured to electrically connect with a proximal interface 176 (FIGS. 2 and 2A). Specifically, the umbrella 174 can be correspondingly shaped to the proximal interface 176. The proximal interface 176 can include a processing board 178 configured to electrically connect with the separable electrical connector 136 (FIG. 7) of the electrical connector 148, or to the conductive paths 140. For example, the processing board 178 can include a separable electrical connector 179 configured to connect with the separable electrical connector 136 of the electrical connector 148. Alternatively, the processing board 178 can be connected directly to the conductive paths 140. In some embodiments, the separable electrical connector 136 of the electrical connector 148 can be at least partially revealed at a face 180 (FIGS. 14, 14A) of the umbrella 174.

The umbrella 174 can be configured to mechanically connect with the proximal interface 176. For example, a fastener 182 (e.g., threaded coupling) can be provided on the face 180 of the umbrella 174. It is noted that, the prosthetic liner 102 may deteriorate more rapidly than the components (e.g., signal processors, microprocessors, memory, battery, etc.) of the processing board 178 of the proximal interface 176. Accordingly, the proximal interface 176 can be reused when the prosthetic liner 102 needs to be replaced.

The proximal interface 176 in the illustrated example is configured to be coupled and decoupled with a distal interface 184 (FIG. 2) on a daily basis. The distal interface 184 can be attached to a prosthetic socket. Each of the distal interface 184 and the proximal interface 176 can include magnetic members that are configured to form a magnetic coupling therebetween. Additionally, the distal interface 184 and the proximal interface 176 can be configured to be decoupled by relative rotation which displaces the magnetic members from one another. An additional clamping member can be provided to selectively retain the distal interface 184 and the proximal interface 176 in alignment to promote the magnetic coupling.

Referring to FIGS. 15, 15A, 16, and 16A, an embodiment of a conductive human interface 200 can be substantially tubular. For example, the conductive human interface 200 can extend between a first open end 204 and a second open end 206. Accordingly, the conductive human interface 200 can be provided as, for example, an arm sleeve, a leg sleeve, a wrist band, a head band, or the like. Generally, the conductive human interface 200 can include the fabric layer 110, the soft coating 120, the electrode 130, and the processing board 178, as described herein with respect to the conductive human interface 100. The connector 148 and the sensor 146 also can be included. Additionally, the conductive human interface 200 can be formed in substantially the same way as the conductive human interface 100. In some embodiments, the electrical connector 148 or processing board 178 can be provided on the exterior surface 114 of the fabric layer 110 between the first open end 204 and the second open end 206. Alternatively, the electrical connector 148 can be provided at the first open end 204, the second open end 206, or both.

Referring to FIGS. 17, 17A, 18, and 18A, an embodiment of a conductive human interface 300 can be formed as a substantially sheet shaped body. For example, the conductive human interface 300 can have a thickness that is defined by the fabric layer 110 and the soft coating 120 and demarcated by a perimeter 302. It is noted that, while the perimeter 302 is depicted in FIG. 17 as being substantially rectangular, the perimeter can be contoured to match with any desired body part. Optionally, the conductive human interface 300 can include a band 304 configured to wrap around a user and secure the conductive human interface 300 to the desired body part. Generally, the conductive human interface 300 can include the fabric layer 110, the soft coating 120, the electrode 130, and the processing board 178, as described herein with respect to the conductive human interface 100. The connector 148 and the sensor 146 also can be included. In some embodiments, the electrical connector 148 or the processing board 178 can be provided on the exterior surface 114 of the fabric layer 110. Additionally, the conductive human interface 300 can be formed in substantially the same way as the conductive human interface 100.

Figure 19:
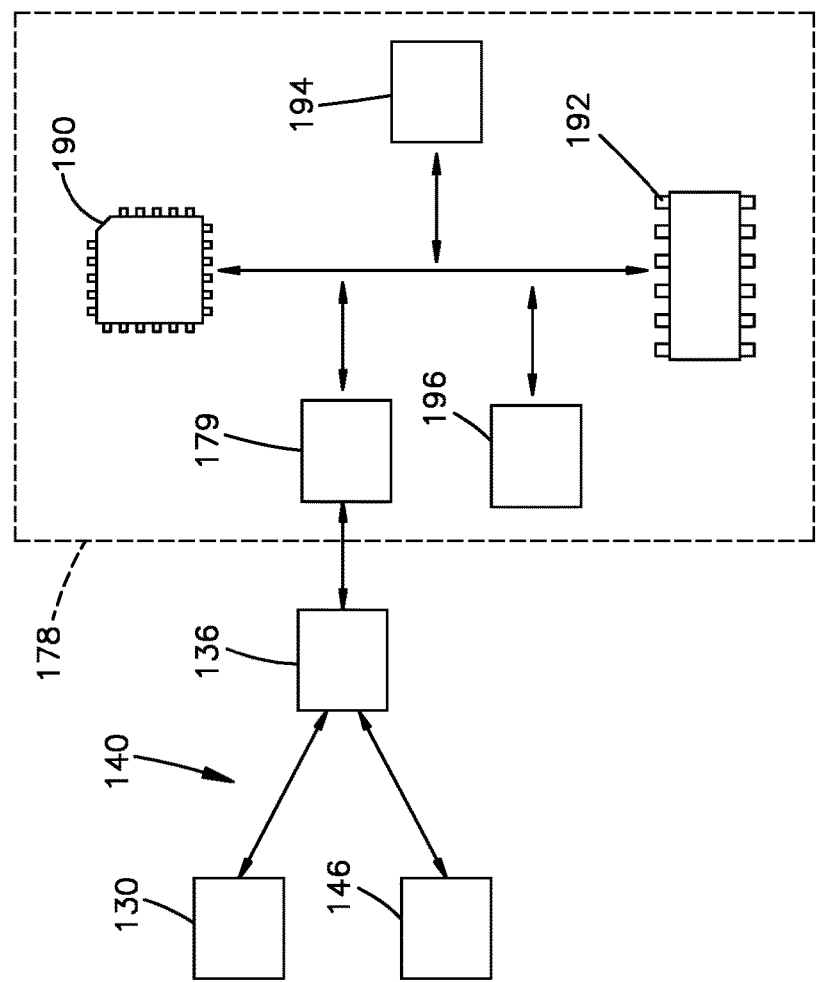
FIG. 19 schematically depicts a processing board.
Figure 18:
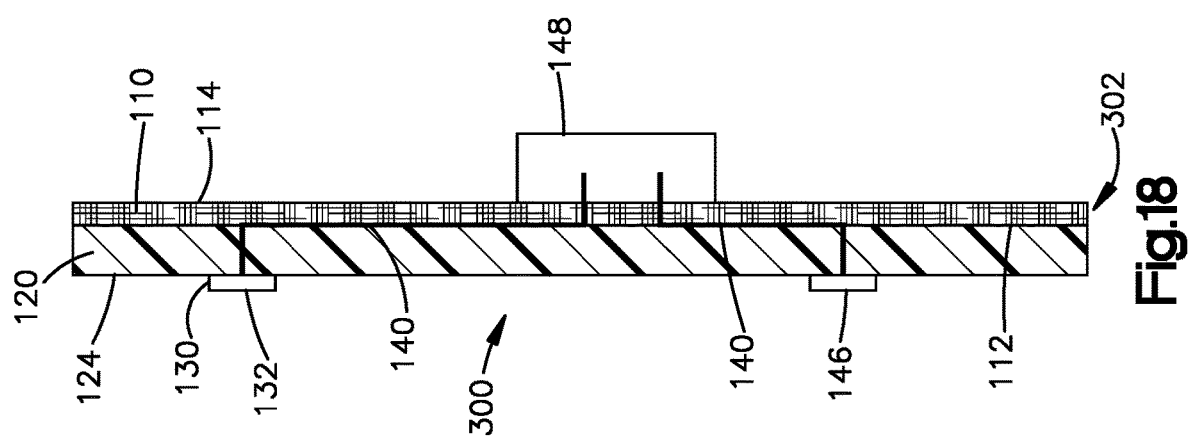
FIG. 18 is a sectional view taken on line 18-18 of FIG. 17.
Figure 19A:
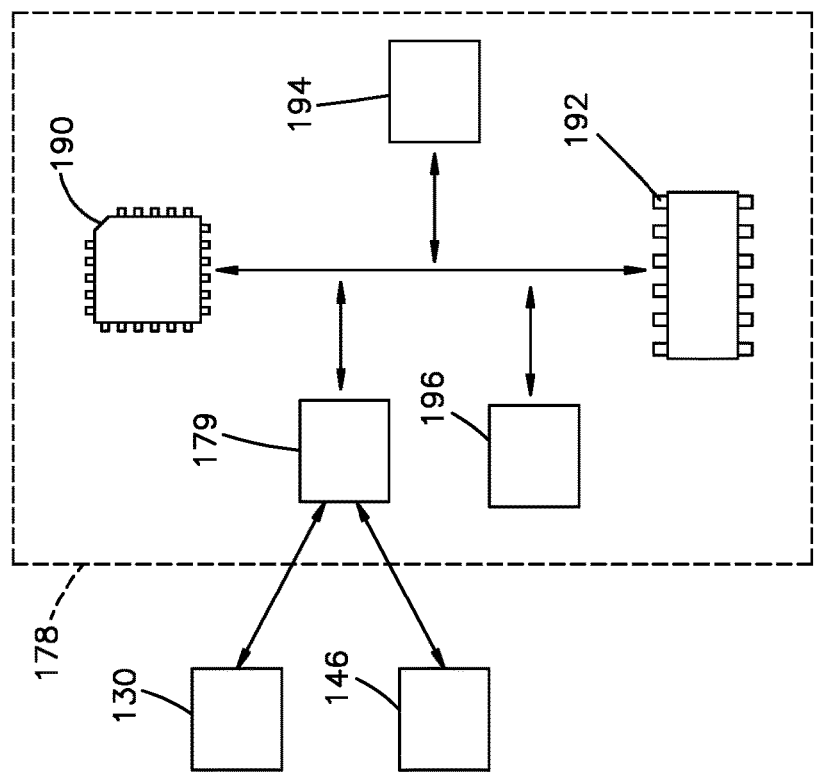
FIG. 19A is a view similar to FIG. 19, showing an alternative configuration of the apparatus.
Figure 18A:
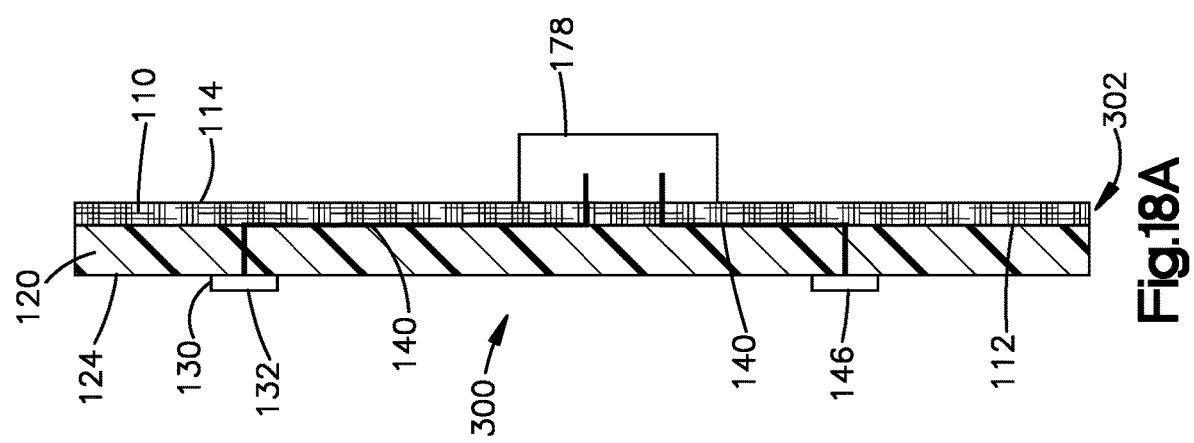
FIG. 18A is a view similar to FIG. 18, showing an alternative configuration of the apparatus.

Referring to FIGS. 2, 19 and 19A, the processing board 178 can be operable to communicate electrical signals with the electrode 130, the sensor 146, or both. The processing board 178 can include one or more processors 190 for executing machine readable instructions to perform signal communication functions, as described herein. The term "processor" can mean any device capable of executing machine readable instructions. Accordingly, each processor can be a controller, an integrated circuit, a microchip, a signal processor, or any other device capable of implementing logic. The processing board 178 can include memory 192 communicatively coupled to the one or more processors 190 (generally depicted as double arrowed lines). As used herein, the phrase "communicatively coupled" can mean that components are capable of exchanging data signals with one another such as, for example, electrical signals via conductive medium, electromagnetic signals via air, optical signals via optical waveguides, and the like. The memory 192 described herein may be RAM, ROM, a flash memory, a hard drive, or any device capable of storing machine readable instructions.

Additionally, it is noted that the functions described herein can be provided as machine readable instructions stored on the memory 192 and executed by the one or more processors 190. The machine readable instructions can be provided in any programming language of any generation (e.g., 1 GL, 2 GL, 3 GL, 4 GL, or 5 GL) such as, e.g., machine language that may be directly executed by the processor, or assembly language, object-oriented programming (OOP), scripting languages, microcode, etc., that may be compiled or assembled into machine readable instructions and stored on a machine readable medium. Alternatively, the functions, modules, and processes described herein may be written in a hardware description language (HDL), such as logic implemented via either a field-programmable gate array (FPGA) configuration or an application-specific integrated circuit (ASIC), and their equivalents. Accordingly, the functions described herein may be implemented in any conventional computer programming language, as pre-programmed hardware elements, or as a combination of hardware and software components.

The processing board 178 can be configured to transform EMG signals detected by the electrode 130 into control signals for an assistive device. Alternatively or additionally, the processing board 178 can be configured to transform sensor signals communicated by the sensor 146 into control signals for an assistive device. For example, the separable electrical connector 179 can be communicatively coupled with the one or more processors 190. Additionally, the processing board 178 can include device communication hardware 194 communicatively coupled to the one or more processors 190. The device communication hardware 194 can be configured to communicate, i.e., send and/or receive data signals via any wired or wireless communication protocol such as, for example, LIN bus, CAN bus, USB, FIREWIRE, IrDA, BLUETOOTH, Wireless USB, Z-WAVE, ZIGBEE, or the like. Accordingly, the one or more processors 190 can receive signals via the separable electrical connector 179 and transform the signals into control signals. The control signals can then be transmitted via the device communication hardware 194 to the assistive device.

Additionally, the processing board 178 can be configured to transmit electrical signals to the electrode 130. For example, the electrical signals can be configured to stimulate nerve endings, create information flowing into the body, or both. In some embodiments, the processing board 178 can include a signal generator 196 configured to generate electrical signals that can be communicated to the electrode 130. For example, the signal generator 196 can be communicatively coupled to the separable electrical connector 179 and the one or more processors 190. Accordingly, the one or more processors 190 can cause the signal generator 196 to generate the desired electrical signal. The electrical signal can be transmitted to the electrode 130 directly by the conductive path 140, or through the separable electrical connector 136 and the conductive path 140. Alternatively, the electrical signals can be provided directly to the separable electrical connector 179 or the conductive path 140 via the device communication hardware 194. Accordingly, in some embodiments, the signal generator 196 is omitted.

The electrical signals can be configured for Transcutaneous electrical nerve stimulation (TENS). Thus, the electrode 130 can be aligned with the desired nerve ending to manage pain. For example, amputees can experience phantom limb pain, i.e., pain that is sensed as coming from an amputated limb. For example, nerve endings at the site of amputation can stimulate the brain in a manner that is interpreted as pain from the removed limb. Alternatively or additionally, the electrical signals can be transmitted to muscle or nerve endings as feedback from an assistive device. For example, amputees using assistive devices such as, for example, a prosthetic foot may have difficulty detecting uneven surfaces. Often times, the amputee may need to look directly at the assistive device in order to traverse an uneven surface. In some embodiments, the assistive device can be provided with sensors configured to detect the uneven surface such as, for example, load sensors to detect the amount and type of loading, and contact sensors configured to detect contact with the surface. In some embodiments, the sensor information can be communicated to the electrode 130 as feedback that can stimulate the brain. For example, the one or more processors 190 can receive sensor data and cause the signal generator 196 to generate the desired electrical signal. The one or more processors 190 can encoded the electrical signal according to the sensor data. Alternatively, the electrical signals can be provided directly to the separable electrical connector 179 via the device communication hardware 194.

Figure 20:
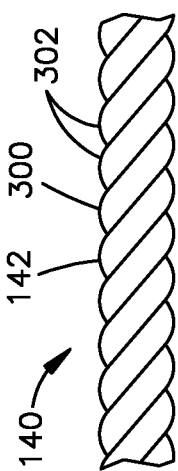
FIG. 20 is an enlarged partial view of a conductor shown FIG. 3.

As described above with reference to the embodiment of FIG. 3, the conductor 140 can be a cord of conductive thread 142 formed of conductive filaments that are spun or twisted together. An example of such a cord 300 is shown in greater detail in FIG. 20. The filaments 302 can include nonconductive substrate material that is coated or embedded with electrically conductive elements. The filaments 302 can alternatively be formed of conductive material such as, for example, stainless steel. In each case, the filaments 302 preferably have a Z twist for sewing, as shown in FIG. 20.

Figure 21:
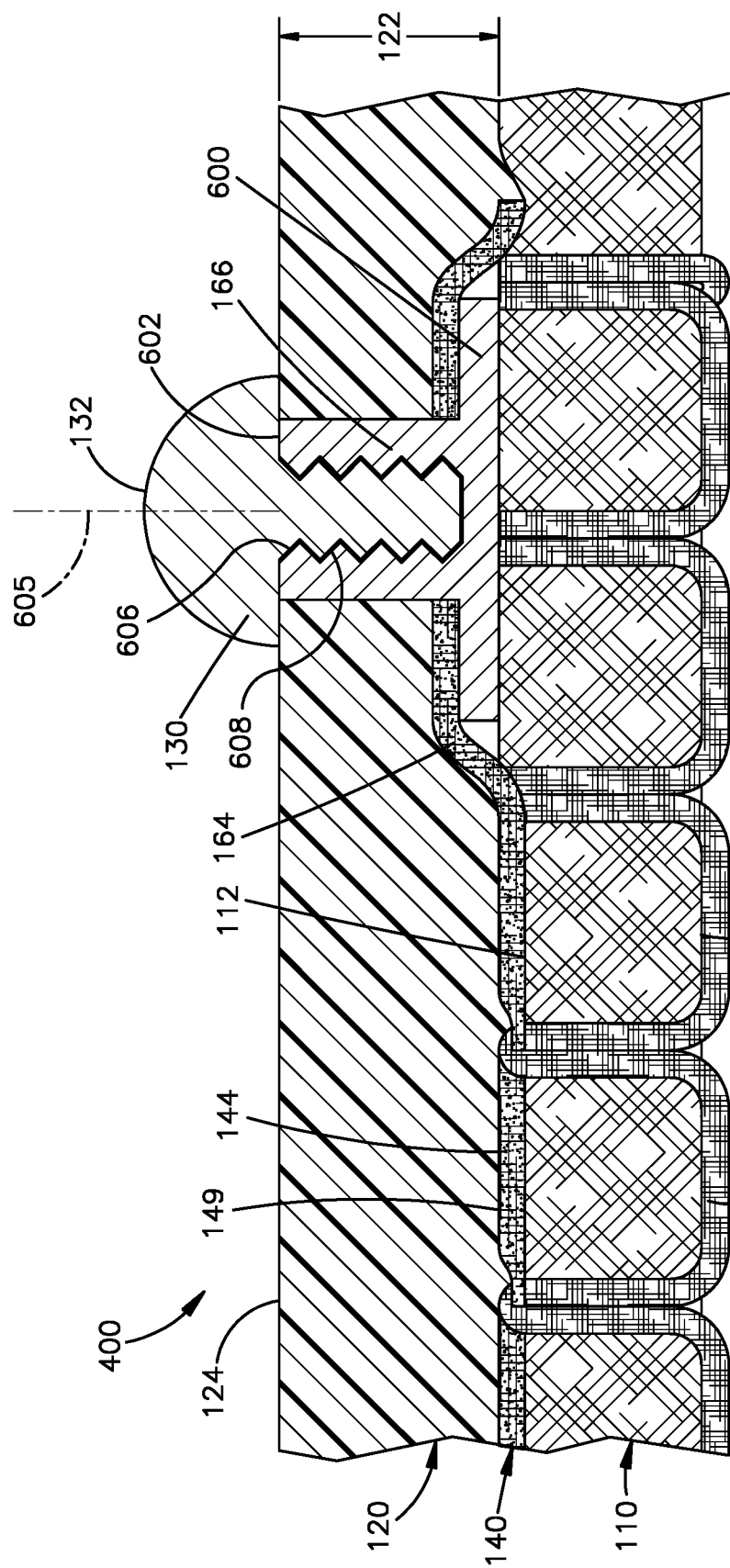
FIG. 21 depicts another alternative embodiment of the structures shown in FIGS. 3-5 and 13.

Another embodiment of a conductive human interface 400 is shown in FIGS. 21 and 22. Specifically, the conductive human interface 400 has a partially assembled condition as shown in FIG. 21, and has a more fully assembled condition as shown in FIG. 22.

In this embodiment, the conductive human interface 400 has many parts that correspond with parts of the conductive human interface 100 described above with reference to FIGS. 2, 2A, and 3. This is indicated by the use of the same reference numbers for such corresponding parts. The conductive human interface 400 thus includes a fabric layer 110 having an interior surface 112 and an exterior surface 114, with a soft coating 120 overlying the interior surface 112. An electrode 130 is configured to electrically connect with human skin. A conductive path 140 is configured to connect the electrode 130 with an electrical connector 148 (FIG. 2) or a processing board 178 (FIG. 2A) which, in turn, is configured to electrically connect with an assistive device. The conductive path 140 includes a conductor 142 having a section 149 overlying the interior surface 112 of the fabric layer 110 between the soft coating 120 and the fabric layer 110.

In the partially assembled condition of FIG. 21, the conductive human interface 400 includes nonconductive support thread 150 extending through the fabric layer 110 from the exterior surface 114 to the interior surface 112. The support thread 150 extends further around the conductor 142 to secure the overlying section 149 of the conductor 142 to the fabric layer 110.

The conductive human interface 400 is advanced from the partially assembled condition of FIG. 21 to the more fully assembled condition of FIG. 22 by removing the support thread 150. The support thread 150 is preferably dissoluble for removal by dissolving in a solvent such as water. The needle punctures 152 and the inherent porosity of the fabric layer 110 may enable the solvent to penetrate from the exterior surface 114 of the fabric layer 110 sufficiently to dissolve the support thread 150 completely. Removing the support thread 150 provides the exterior surface 114 with a smoother contour and texture. At the interior surface 112, the overlying section 149 of the conductor 142 remains secured in the conductive path 140, but is released from the support thread 150 to enable a slight amount of shifting on the surface 112 as needed in response to forces imparted from the residual limb or the connected prosthetic device.

In an alternative method of assembly the support thread 150 can be omitted. Such a method could comprise the steps of connecting a conductor between an electrical connector and an electrode or sensor; placing a section of the conductor in a position overlying an interior surface of a fabric layer; forming an adhesive bond securing the overlying section of the conductor to the interior surface of the fabric layer; applying a soft coating over the interior surface of the fabric layer, the overlying section of the conductor, and portions of the support thread reaching around the conductor; and removing the adhesive bond.

In the foregoing method, the adhesive bond can be formed of a dissoluble adhesive material, and preferably a water-dissoluble adhesive material. The step of removing the adhesive bond would then comprise dissolving the adhesive bond, and more specifically dissolving the adhesive bond in water. A cornstarch mixture could serve as the water-dissoluble adhesive material.

In each embodiment, the conductors 140 are preferably elongated lengthwise of the respective fabric layer. This is illustrated by the examples shown in FIGS. 8, 9, and 12, where the conductors 140 are shown to be elongated in directions either parallel or generally oriented in alignment with the length of the prosthetic liner 102 along the axis 103. In each case, the section 149 of the conductor 140 that overlies the fabric layer 110 has one or more extendable length portions 500, as shown for example in the schematic view of FIG. 23. The extendable length portion 500 is elongated in a longitudinal direction along an axis 503, and has a proximal end 510 and a distal end 520. The distal end 520 is spaced from proximal end 510 at a linear distance D in the longitudinal direction. However, the extendable length portion 500 itself is longer than the linear distance D between the opposite ends 510 and 520. The greater length enables the overlying section 149 of the conductor to 140 elongate in the longitudinal direction when the fabric layer stretches in the longitudinal direction.

In the example shown schematically in FIG. 24, the extendable length portion 500 of the conductor 140 has first segments 530 and second segments 532. The first segments 530 reach distally in orientations laterally toward one side of the longitudinal direction. The second segments 532 alternate with the first segments 530, and reach distally in orientations laterally toward an opposite side of the longitudinal direction. As shown in 24, the alternating segments 530, 532 are linear and reach distally in a zig-zag configuration with corners 540 between adjacent segments 530, 532. In the example of FIG. 25, the alternating segments 530, 532 are arcuate and reach distally in a serpentine configuration with turns 550 between adjacent segments 530, 532. Although the illustrated examples are oriented for stretching in the longitudinal directions, the conductors could likewise have extendable length portions oriented for stretching in lateral or other stretchable directions.

Referring again to FIGS. 21 and 22, the electrode connector 166 has a base portion 600 and a column portion 602, both of which have circular cross-sectional shapes centered on an axis 605. The base 600 can be adhesively bonded to the interior surface 112 of the fabric layer 110. The base 600 can alternatively be adhesively bonded to the exterior surface 114, with the column 602 extending inward through the fabric layer 110. In that condition an electrically nonconductive cap, such as a body of polyurethane gel, would be received over the base 600.

The column 600 in this example has an internal screw-thread 606 for engaging an external screw thread 608 on the electrode 130. This enables the user to install electrodes 130 at fewer than all of the connectors 166, leaving the remaining connectors 166 free of electrodes 130 at the contact surface 124. The conductive human interface 400 is thus adaptable for a user to employ electrodes 130 at only selected locations on the residual limb, although other locations are also available as needed, and thereby to avoid discomfort where unnecessary electrodes 130 might be located.

An alternative configuration of the electrode connector 166 is shown in FIG. 26. In this configuration, the base 600 of the connector 160 has an aperture 613 for a fastener to connect the conductor 140 to the base 600. The base 600 also has a generally oblong peripheral shape that is elongated on a longitudinal centerline 615. The elongated configuration of the base 600 provides space for the aperture 613 without the need to widen the base 600 laterally relative to the size of the circular base 600 in the embodiment of FIG. 22. The electrode connector 166 can thus fit more compactly beside and between adjacent connectors 166 that are aligned in the axial directions 503 shown in FIGS. 23, 24, and 25.

As shown in FIG. 27, the fastener can be a rivet 620, which is preferably formed of stainless steel. A compliant washer 622 is clamped between the rivet 620 and the conductive path 140 to prevent the conductive path 140 from being damaged by the rivet 620.

It should now be understood that the embodiments described herein can provide relatively durable and comfortable conductive human interfaces. The EMG signals can be communicated to signal processing devices that are located external to the conductive human interface by flexible and durable conductive paths. Moreover, the conductive interfaces can include sensors for providing additional control input. For example, temperature sensors, moisture sensors, or both can be used to control temperature control devices provided in the interface (e.g., prosthetic liner). Alternatively or additionally, the sensors can be configured to detect contact pressures, which can be used as control input to alter the shape or operation of an assistive device. Specifically, signals from the calf area can be used to control an ankle foot orthosis to adjust the stiffness of the device or the position of the components (e.g., ankle location). Moreover, feedback signals can be provided to the user via electrodes to help the user sense and control assistive devices.

There are other benefits that arise from inserting electrodes into a flexible liner, including increasing the number of muscle sites that can be accessed for collecting EMG signals. In a traditional EMG controlled prosthesis, the electrodes are inserted directly into a substantially rigid socket or inner socket. In this traditional configuration, EMG electrodes cannot be used to collect information from regions of the user's body that extend substantially outside of the socket. This limits the receptive field for EMG signals to tissues that are substantially inside of the socket. Use of a flexible liner with integrated electrodes allows electrodes to be applied to regions of tissue that extend beyond the socket. This allows for EMG signals to be collected from regions of tissue that extend across a joint. For example, in a traditional below elbow EMG controlled prosthesis, electrodes could only be placed in the socket and EMG signal collection would be limited to tissues at or below the elbow. However, muscles that control the wrist and hand are known to originate above the elbow and cross the elbow joint. By utilizing a flexible liner with embedded electrodes, the liner can extend beyond the socket, across the elbow, and allow EMG signals to be collected from above the elbow. For this reason, a flexible liner with embedded electrodes that extends beyond the socket allows for the collection of additional information that can be used to control a prosthetic wrist and hand from, for example, the supinator muscle, the pronator teres muscle, and other muscles, which would not be available with traditional EMG control. This additional information can improve the user's control over pronation and supination and other functions. This benefit is not limited to pronation and supination, below elbow applications, or upper extremity prosthetics. As examples, expansion of the EMG receptive field across the elbow can also benefit other functions such as wrist flexion/extension and finger flexion/extension in the upper extremity prosthesis, while placement of electrodes above the knee could collect information from the plantaris muscle to facilitate control of ankle flexion of prostheses for below knee amputees.

Figure 28:
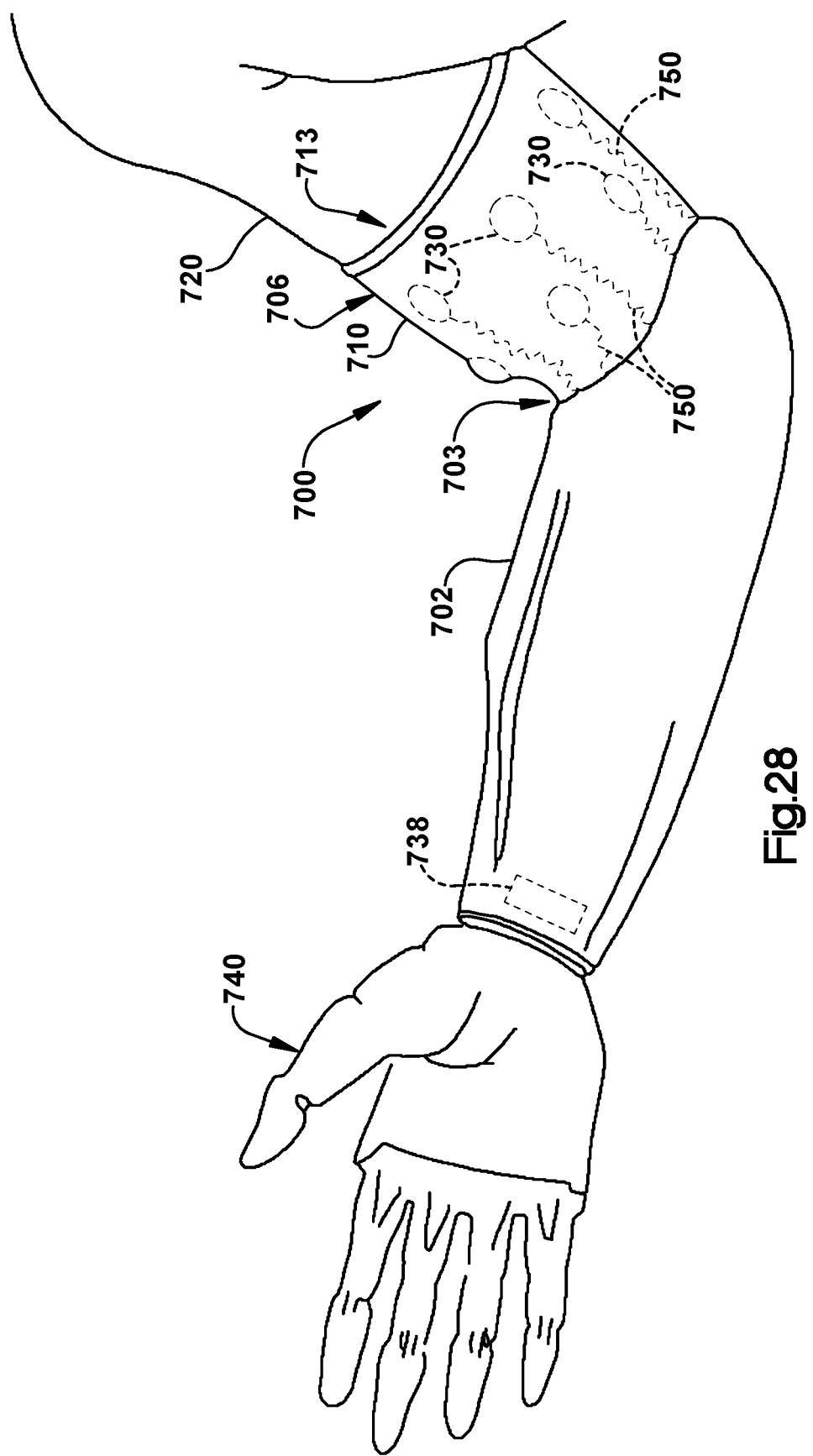
FIG. 28 depicts an alternative embodiment of a conductive human interface.

As an example of the foregoing considerations, the conductive human interface 700 of FIG. 28 is associated with a socket 702. The socket 702 has a socket opening 703 for insertion of a liner 706. The liner 706 has a proximal end portion 710 with a liner opening 713 for insertion of a residual limb 720. The liner 706 takes an operative position in which a distal end portion of the liner 706 is received in the socket 702, and the proximal end portion 710 projects outward from the socket opening 703. An array of electrodes or sensors 730 are mounted on the proximal end portion 710 of the liner 706 in the same or substantially the same manner as described above regarding the electrodes 130, and are configured to electrically connect with the residual limb 720.

As shown schematically in FIG. 28, an electrical connector 738 is included to electrically connect the electrodes or sensors 730 with a prosthetic device 740. A corresponding array of conductive paths 750 interconnect the electrodes or sensors with the electrical connector 738. The conductive paths 750 can be configured in the same or substantially the same manner as the conductive paths 140 described above. One or more of the conductive paths 750 may reach through the socket opening 703 from the proximal end portion 710 of the liner 706 to the distal end portion when the when the liner 706 is in the operative position.

Figure 29:
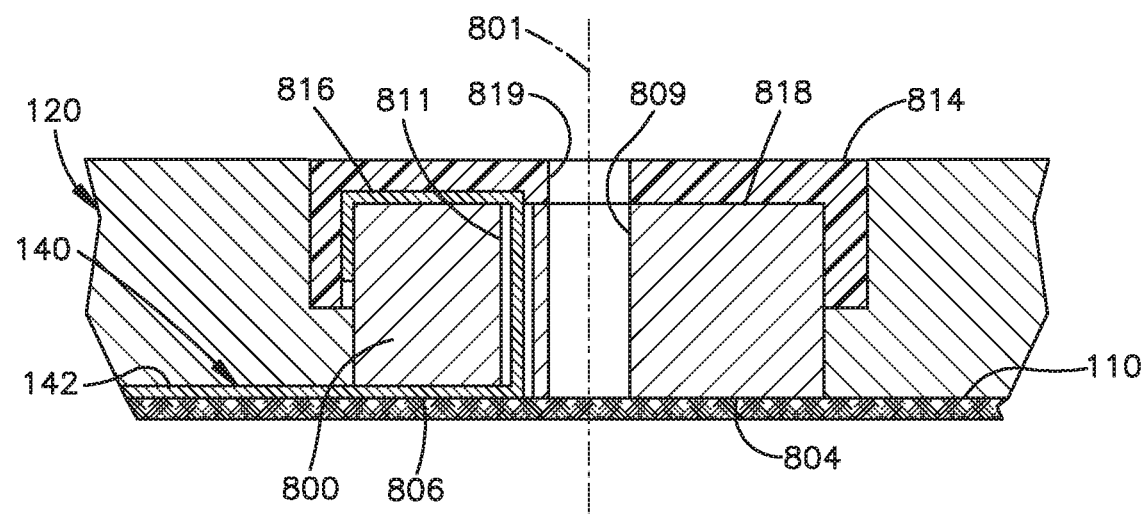
FIG. 29 is a sectional view of another alternative embodiment of an electrode connector.

An alternative embodiment of an electrode connector 800 is shown in FIG. 29. The connector 800 in this example is a cylindrical body of conductive material centered on an axis 801. A bottom surface 804 of the connector 800 overlies the fabric layer 110. The bottom surface 804 also overlies a section 806 of the conductor 142 in the associated conductive path 140. A central bore 809 in the connector 800 is configured to receive the stem of an electrode 130 as described above, and may have an internal screw thread. An off-center bore 811 provides a passage for the conductor 142 to reach upward from the fabric layer 110 through the connector 800. A non-conductive cap 814 is received over the connector 800 to hold a trimmed end section 816 of the conductor 142 in contact with a top surface 818 of the connector 800. The cap 814 also has a central bore 819 for the electrode stem.

Figure 30:
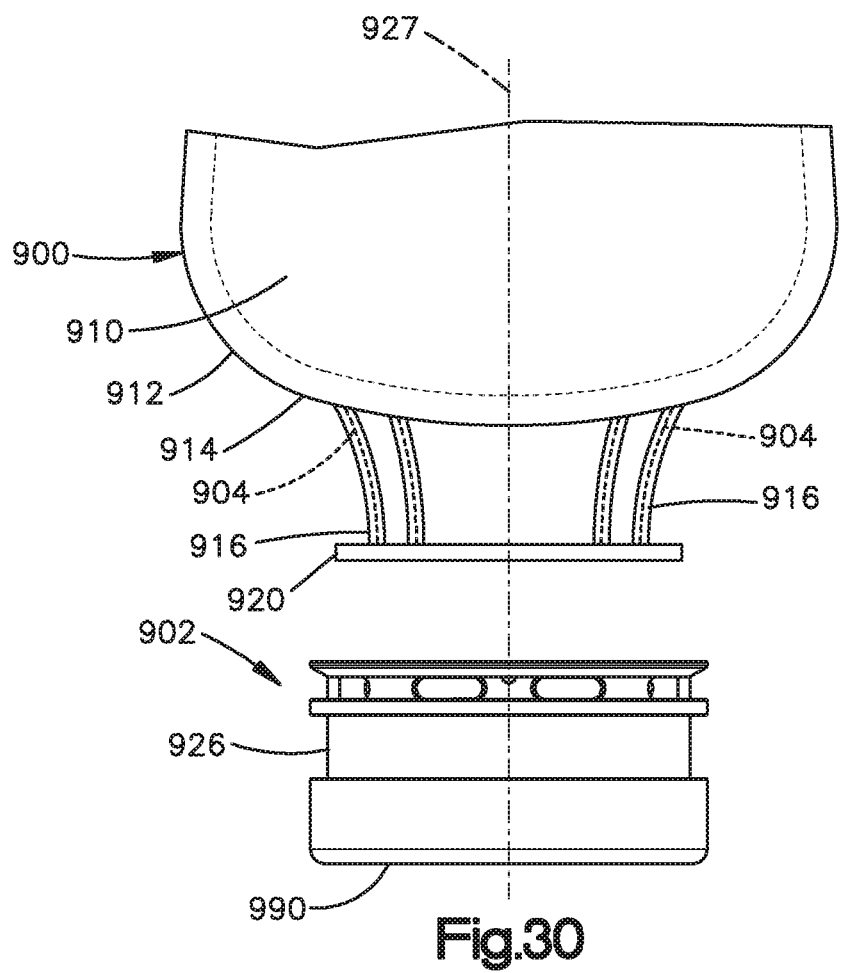
FIG. 30 is an exploded view of parts of a proximal interface.
Figure 31:
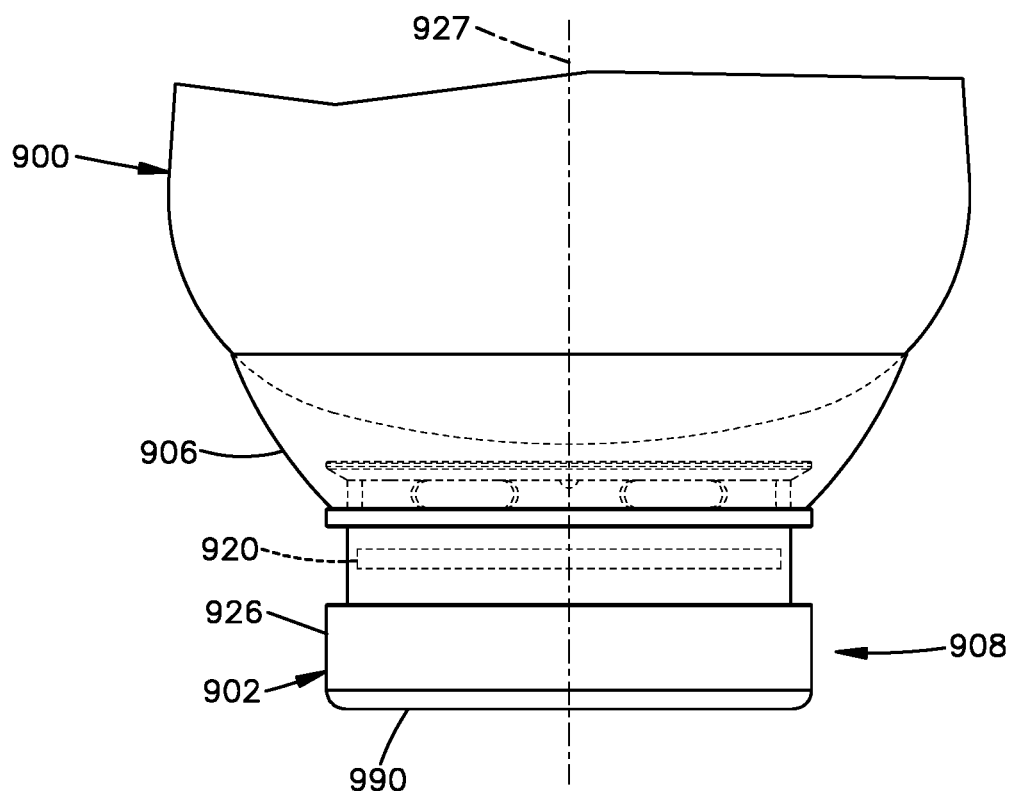
FIG. 31 is a view showing the parts of FIG. 30 in an interconnected condition.

FIGS. 30 and 31 show an example of a liner 900 and an associated electronics housing 902. The liner 900 is equipped with electrodes that are configured and interconnected with conductive paths 904 in any of the configurations described above. The housing 902, which is shown separately from the liner 900 in FIG. 30, is attached to the liner 900 as shown in FIG. 31. The attachment is preferably made by a body 906 of molded polymeric material, such as urethane, defining an umbrella as shown in FIG. 31. The interconnected liner 900 and housing 902 together provide a proximal interface 908 for engagement with a distal interface in a socket.

As in the example of FIG. 12, these conductive paths 904 extend beyond the exterior surface 910 of the fabric layer 912 at the distal end 914 of the liner 900. The extended sections of the conductive paths 904 reach through plastic tubes 916 for stress and strain protection at the exterior of the liner 900.

As further shown in FIG. 30, the conductive paths 904 are electrically connected to a circuit board 920. These connections can be made by connection hardware such as, for example, the conductive members 134 of FIG. 7. The extended sections of the conductive paths 904 are long enough for handling upon connection to the circuit board 920, and are also long enough to be bundled between the liner 900 and the circuit board 920 in the assembled condition of FIG. 31. Such bundling is preferably accomplished by rotating the board 920 about the longitudinal axis 923 of the liner 900 to gently wind up the plastic tubes 916 and draw the board 920 axially toward the liner 900.

The housing 902 in the given example includes a metal housing wall 926. The housing wall 926 has a cylindrical shape centered on an axis 927. As shown in the sectional view of FIG. 32, the housing wall 926 has an open proximal end 928 and an open distal end 930. An inner surface 932 of the housing wall 926 defines a ledge 934 extending circumferentially about the inner perimeter. The inner surface 932 also defines a recess 935 extending circumferentially about the inner perimeter. An outer surface 936 defines a proximal recess 937 and an intermediate recess 939, both of which extend circumferentially about the outer perimeter. Apertures in the shape of slots 941 extend through the housing wall 926 in the proximal recess 937. The slots 941 and the proximal recess 937 provide flow paths for the fluid urethane of the umbrella 906 to reach through and envelop the housing wall 926 adjacent to the open proximal end 928.

Figure 33:
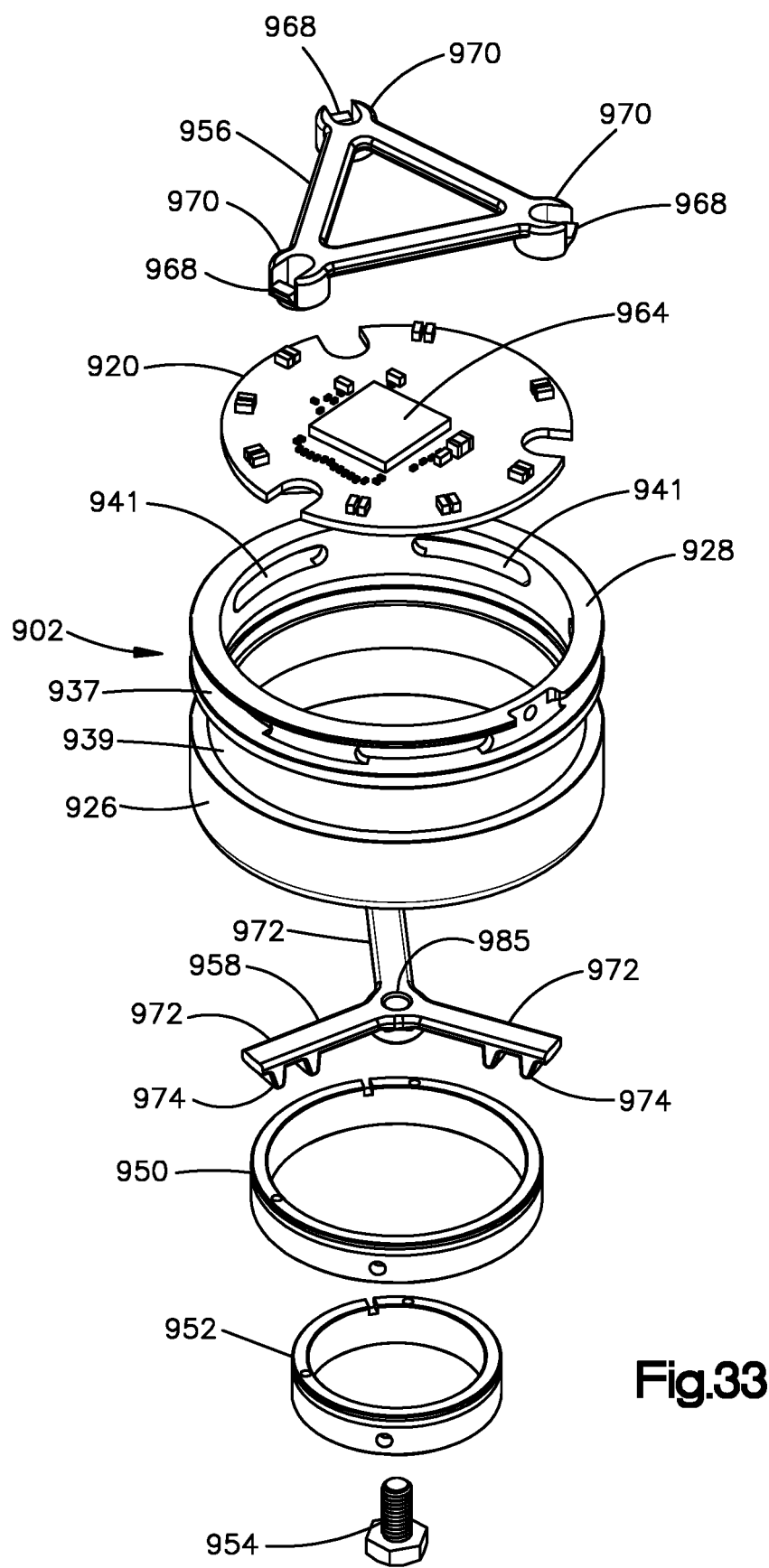
FIG. 33 is an exploded view of parts of the interface of FIG. 30.

As shown schematically in FIGS. 30 and 31, the housing 902 contains the circuit board 920. The circuit board 920, as well as other components contained in the housing 902, is shown in greater detail in the exploded view of FIG. 33. The other components include first, second and third electrical contacts 950, 952 and 954. Also included are a board clip 956 and a contact clip 958.

Figure 34:
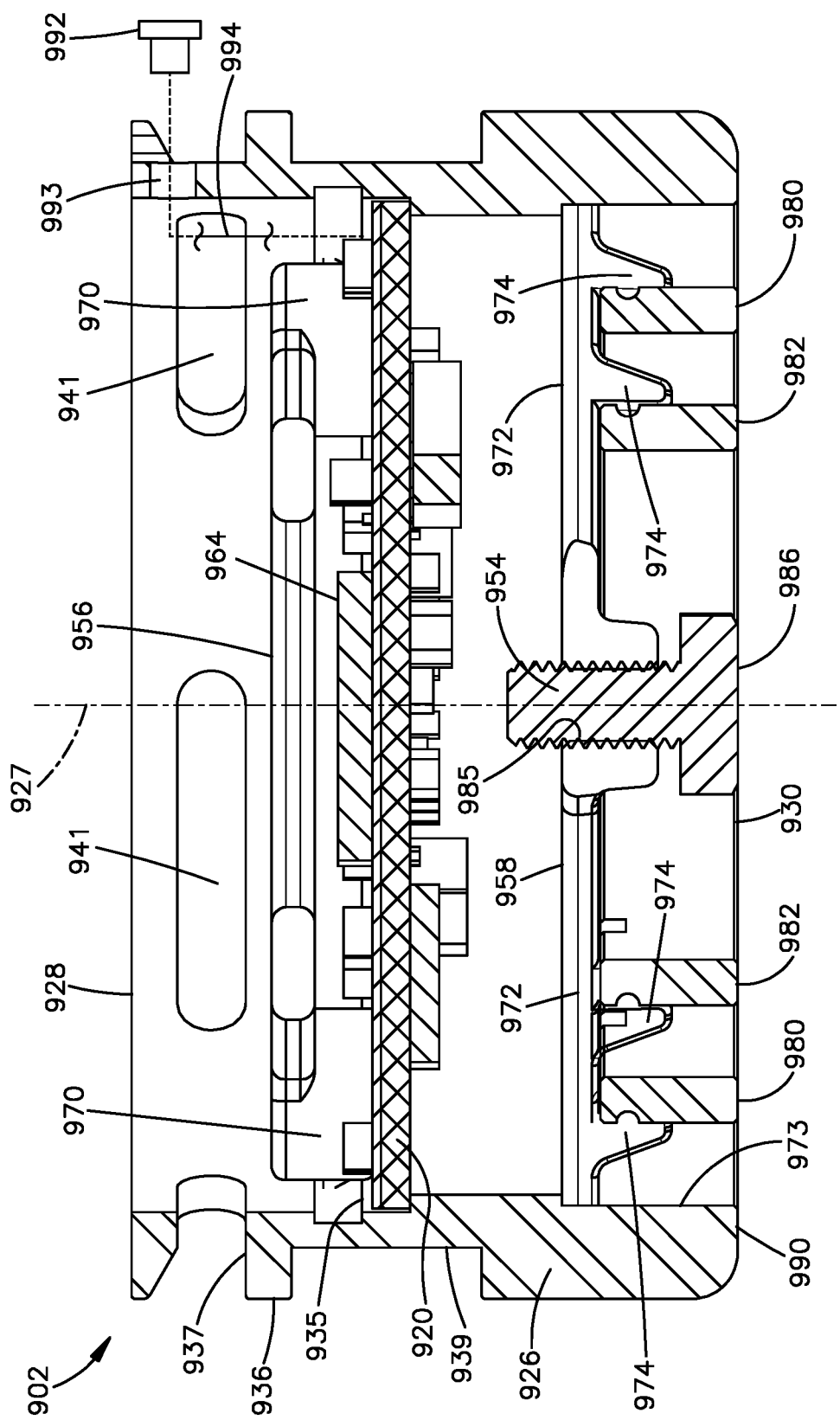
FIG. 34 is a side sectional view of parts shown in FIG. 33.
Figure 35:
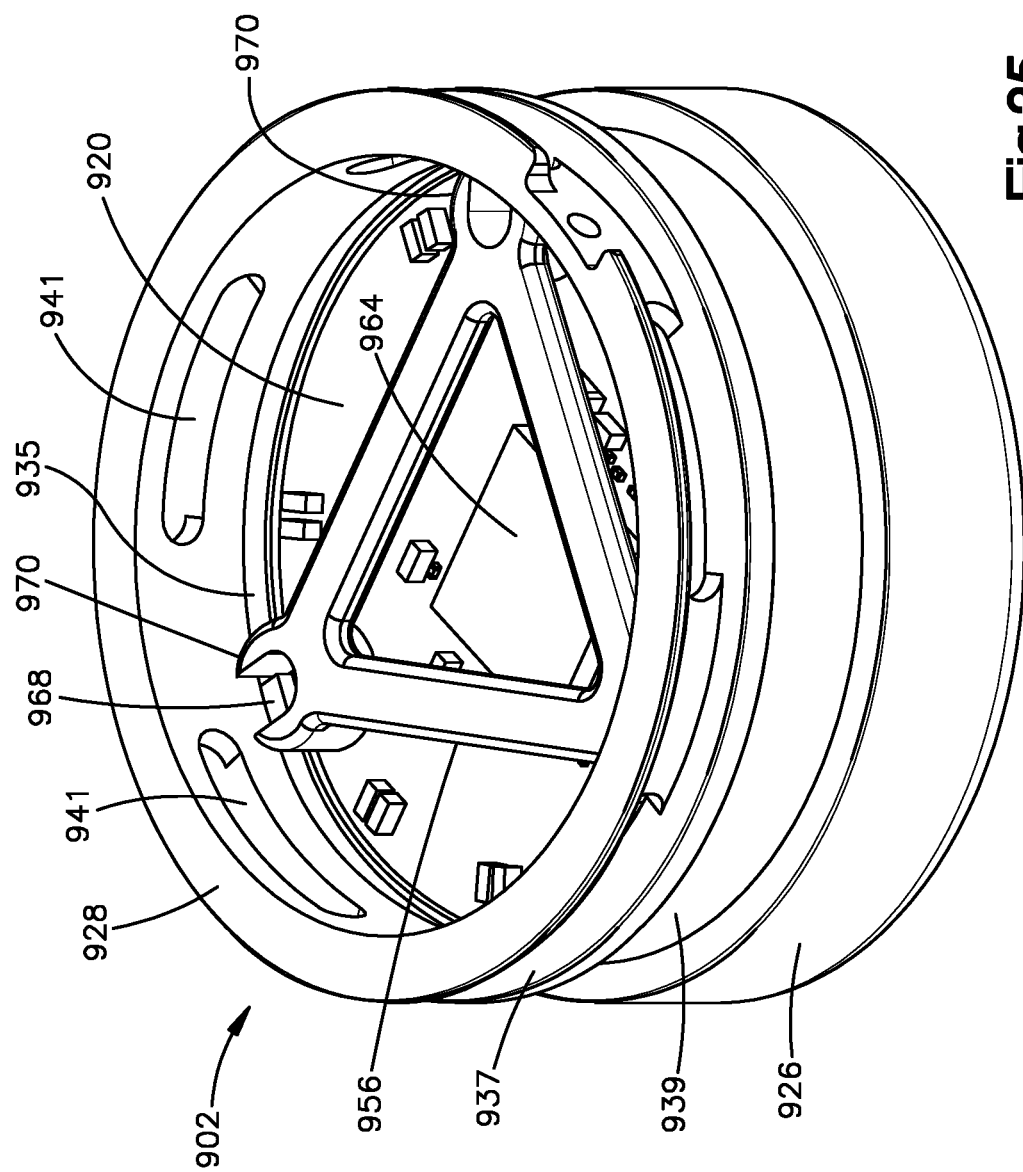
FIG. 35 is a perspective view, taken from above, of the parts shown in FIG. 34.

A processor 964 is mounted on the circuit board 920. The processor 964 is configured for the circuit board 920 to function as described above. The board clip 956 is a triangular frame with snap tabs 968 at the three corners 970. As shown in FIG. 34, the circuit board 920 is seated on the ledge 934 in the housing 902. As best shown in FIG. 35, the board clip 956 is received over the circuit board 920. The tabs 968 are snapped into the inner recess 935 to retain the circuit board 920 in place.

The first and second contacts 950 and 952 are circular rings. The contact clip 958 has radially projecting arms 972. As shown in FIG. 34, the arms 972 engage the housing 902 in a recess 973 at the open distal end 930 of the housing wall 926. Pairs of tabs 974 on the arms 972 engage the contacts 950 and 952. The tabs 974 support the contacts 950 and 952 coaxially within the recess 973. Distal edges 980 and 982 of the contacts 950 and 952 are coplanar with the open distal end 930, which is perpendicular to the axis 927. The distal edges 980 and 982 serve as ring-shaped electrical contact surfaces at that location. This is best shown in the end view of FIG. 36.

Figure 36:
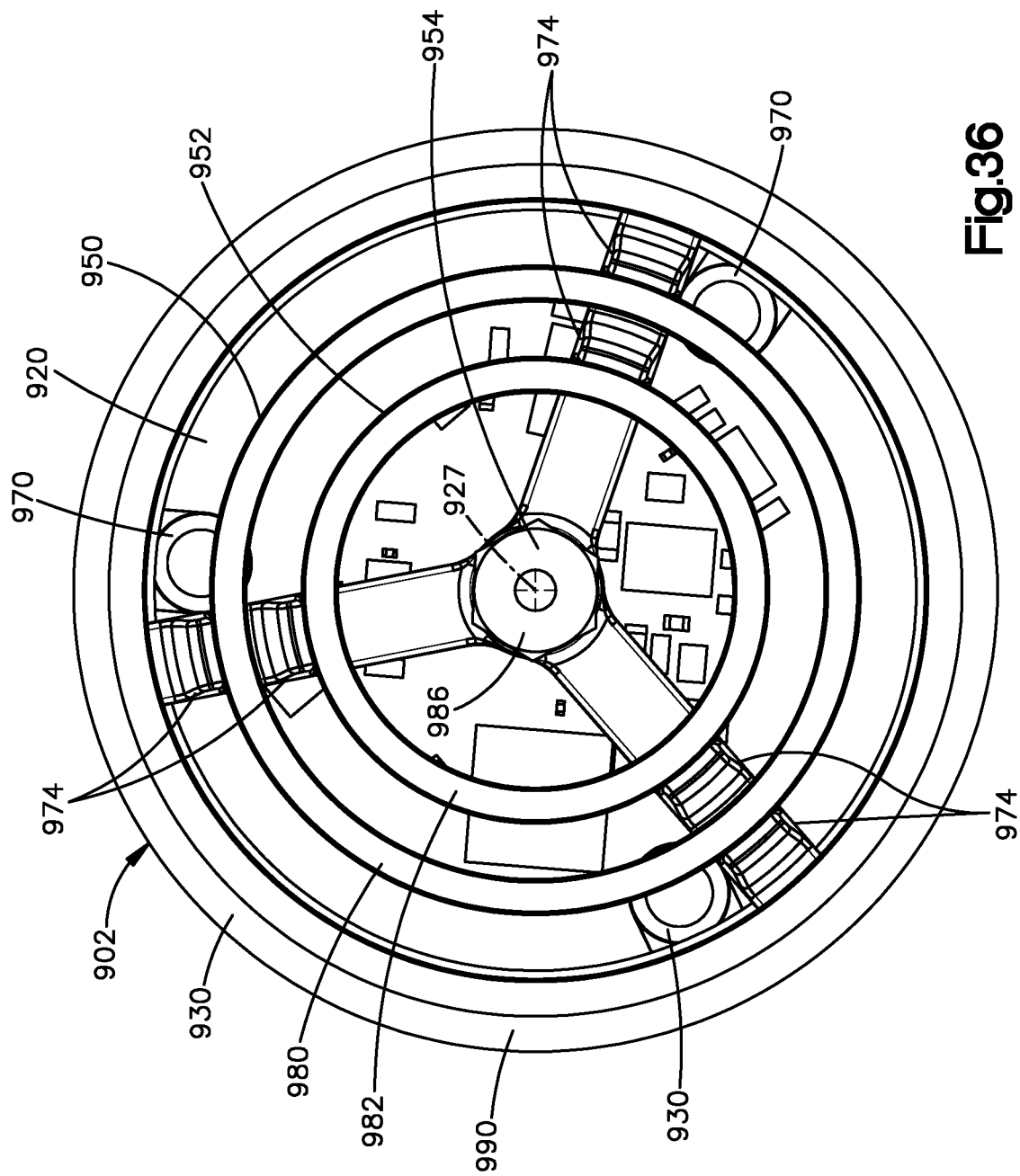
FIG. 36 is a bottom view of the parts shown in FIG. 34.

The third contact 954 also is received within the housing 920, as shown in FIGS. 34 and 36. In the illustrated example, the third contact 954 is a machine screw received in a threaded bore 985 at the center of the contact clip 958. An end surface 986 on the head of the third contact 954 is coplanar with the edge surfaces 980 and 982 on the other two contacts 950 and 952, and is thereby arranged as an additional electrical contact surface at the open distal end 930.

In the arrangement of FIG. 34, electrical connections (not shown) are provided to interconnect the three electrical contacts 950, 952, and 954 with the processor 964 and associated additional electrical components mounted on the circuit board 920. Such connections may be configured in any suitable manner. The first and second contacts 950 and 952 are interconnected with the processing board 920 to function as signal contacts. The third contact 954 is interconnected with the processing board 920 as a power contact. An additional body of molded urethane, or an extension of the body 906 of FIG. 31, is injected throughout the interior of the housing 902 as needed to encapsulate and retain the circuit board 920, the contacts 950, 952, and 954, and the clips 956 and 958 within the housing 902, with the contact surfaces 980, 982, and 986 exposed at the open distal end 930. A distal edge surface 990 of the housing wall 926 serves as a ground contact that also is exposed at the open distal end 930. A rivet 992 or other fastener is received through an aperture 993 near the open proximal end 228, and is interconnected with the circuit board 920 by wiring 994 (shown schematically). The assembled apparatus of FIG. 31 is thus configured as the proximal interface for engagement with a distal interface as noted above.

Figure 37:
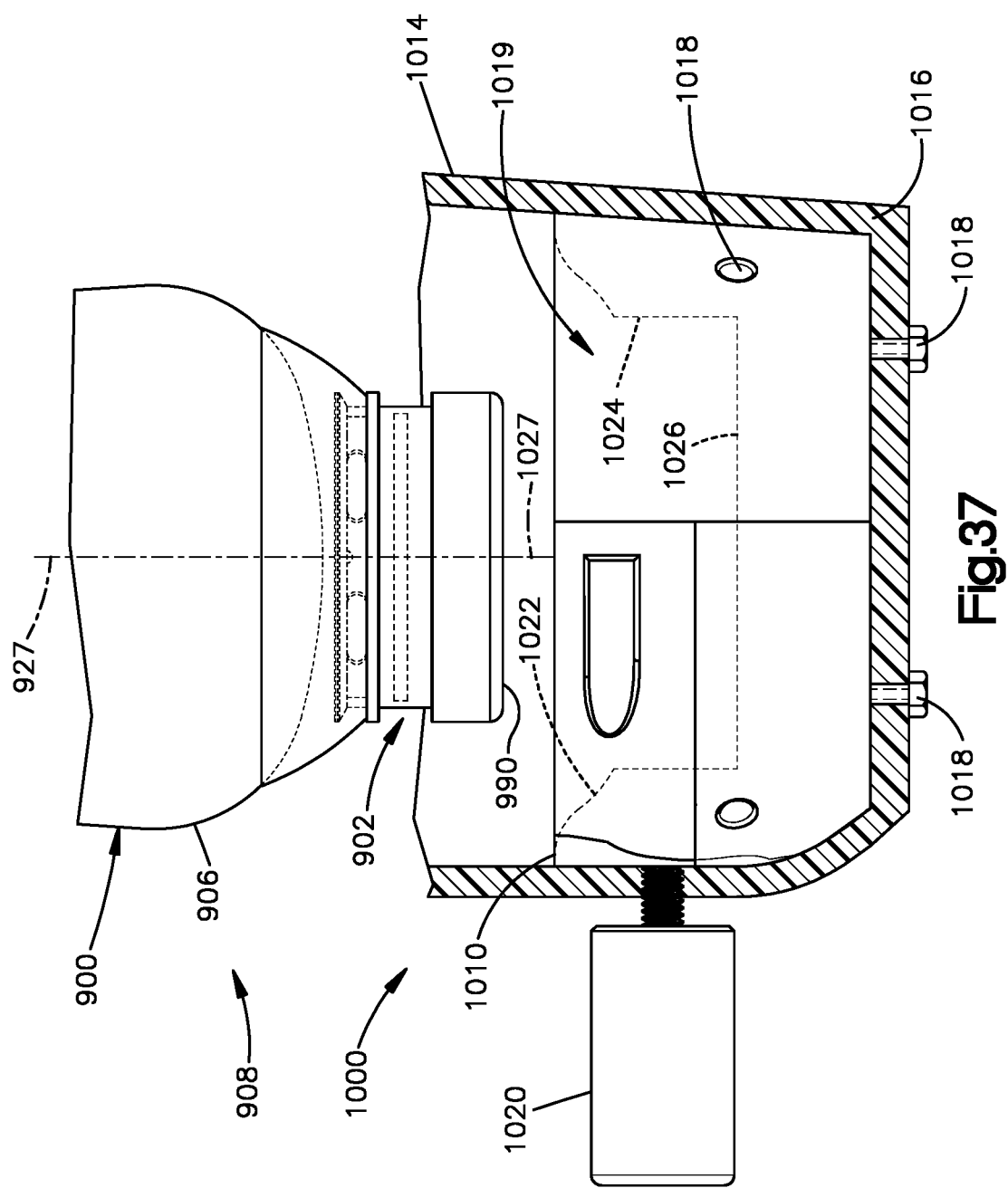
FIG. 37 is a side view showing parts of a distal interface for use with the proximal interface of FIG. 31.

An example of a distal interface 1000 for use with the proximal interface 908 is shown partially in FIG. 37. This includes a housing 1010 which, in this context, may be referred to a distal housing for use with the proximal housing 902 on the liner 900.

Figure 38:
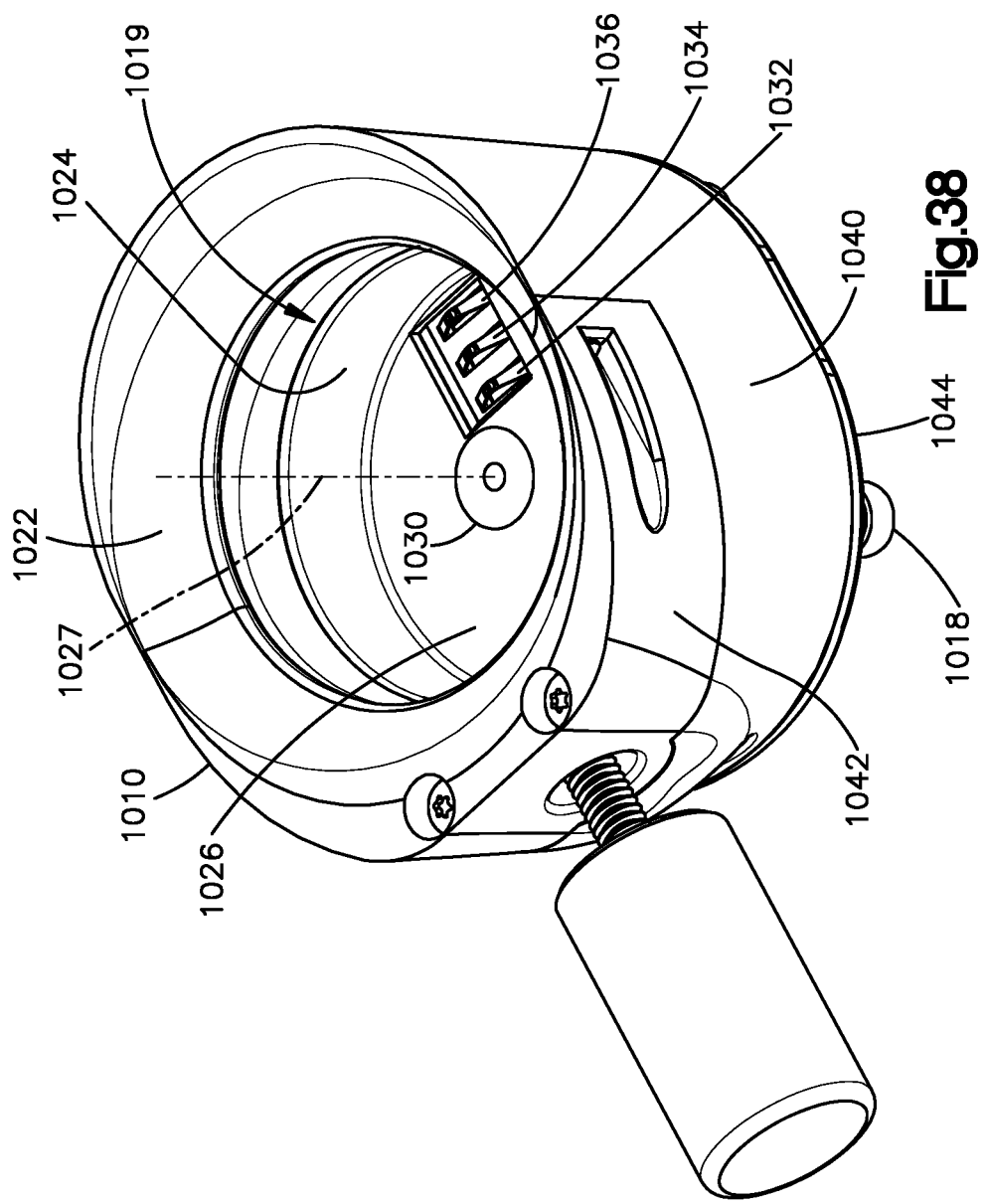
FIG. 38 is a perspective view, taken from above, of parts shown in FIG. 37.

The distal housing 1010 is closely fitted within a socket 1014 at a closed distal end 1016 of the socket 1014, and is retained in place by fasteners 1018 (FIG. 38). The proximal housing 902 is receivable in a compartment 1019 in the distal housing 1010 upon insertion of the liner 900 and residual limb fully into the socket 1014. A spring-loaded locking mechanism 1020 has a normally locked condition retaining the proximal housing 902 in the distal housing 1010, and is operable manually to release the proximal housing 902 for removal from the distal housing 1010 and the socket 1014.

As further shown in FIGS. 37 and 38, the distal housing 1010 has a chamfered open edge 1022 for guiding the proximal housing 902 coaxially into the compartment 1019. The compartment 1019 has a cylindrical peripheral wall 1024 centered on an axis 1027. A circular bottom wall 1026 also is centered on the axis 1027. Four electrical contacts 1030, 1032, 1034 and 1036 are provided on the bottom wall 1026. The first contact 1030 is a power contact. The second and third contacts 1032 and 1034 are signal contacts. The fourth contact 1036 is a ground contact.

The power contact 1030 in the distal housing 1010 is located on the axis 1027. The power contact 1030 is thus positioned for alignment and contact with the power contact 954 at the center of the proximal housing 902 (FIG. 36) when the proximal housing 902 is installed in the compartment 1019. Additionally, the power contact 1030 in the given example is a magnet for helping to retain the proximal housing 902 in the compartment 1019.

The signal contacts 1032 and 1034 in the distal housing 1010 are spaced radially from the axis 1027 at distances equally to the radii of the ring-shaped signal contacts 952 and 950 in the proximal housing 902. The ground contact 1036 in the distal housing 1010 is likewise spaced radially from the axis 1027 equally with the ring-shaped ground contact 990 at the open distal end of the proximal housing 902. These radial placements and configurations ensure that the contacts in the proximal housing 902 will make contact with their counterparts in the distal housing 1010 in any relative rotational orientation of the housings 902 and 1010 about the aligned axes 927 and 1027.

Figure 39:
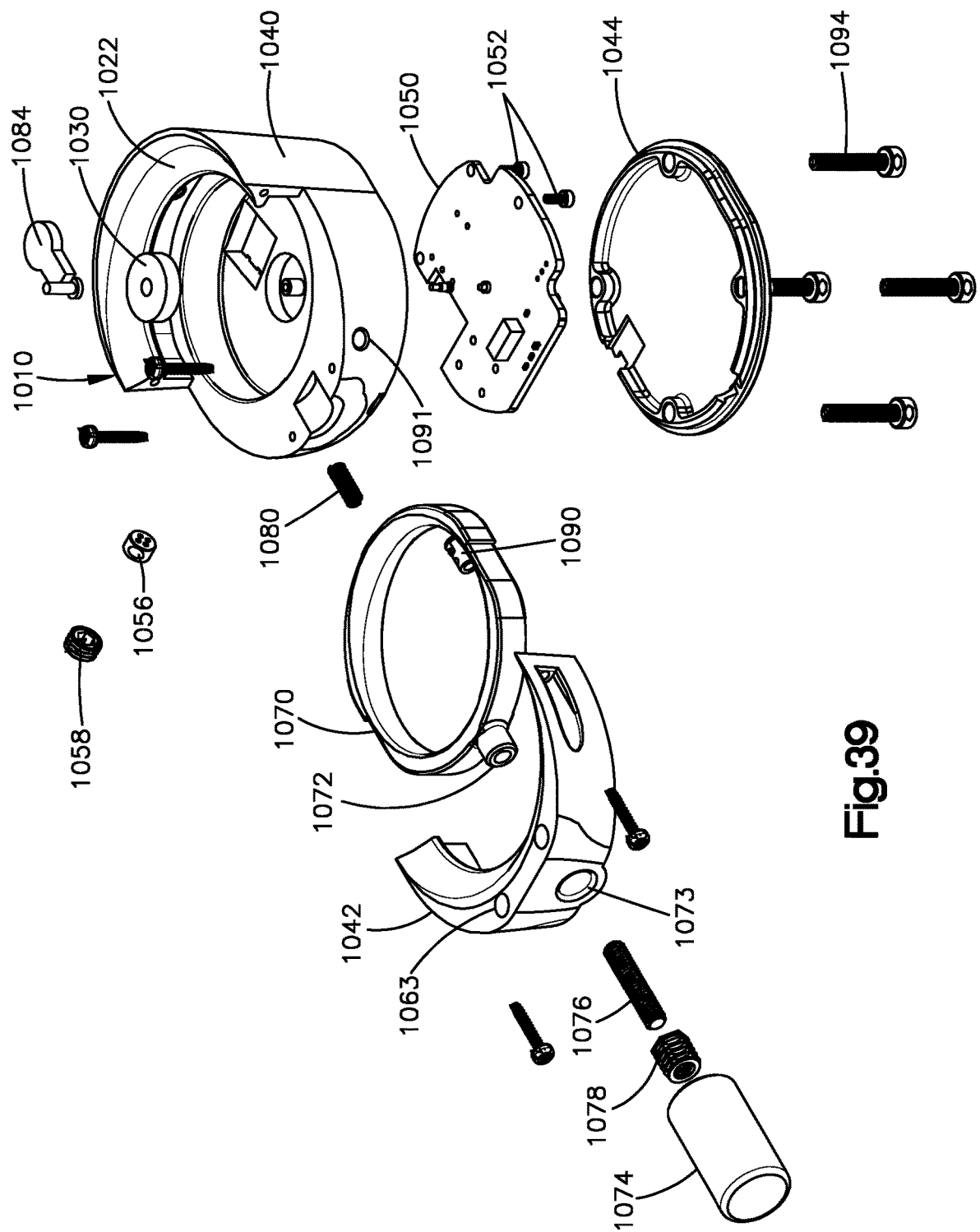
FIG. 39 is an exploded view of the parts shown in FIG. 38.

As further shown in the exploded view of FIG. 39, the distal housing 1010 in the illustrated example has parts including a generally cylindrical body 1040, an arcuate segment 1042, and a closure panel 1044. A circuit board 1050 is received in the body 1040 beneath the bottom wall 1026 of the compartment 1019. Fasteners 1052 fasten the circuit board 1050 to the body 1040. The circuit board 1050 supports electrical components configured to interconnect the contacts 1030-1036 with cables reaching to the assistive prosthetic device. The segment 1042 has an aperture containing a cable gland 1056 and a cable set screw 1058 through which the cables emerge from the housing 1010.

A lock ring 1070 is received radially between the segment 1042 and the body 1040. A boss 1072 on the lock ring 1070 projects radially through an aperture 1073 in the segment 1042. A pushbutton 1074 is connected to the boss 1072 by a lock release post 1076 and a threaded insert 1078. A spring 1080 is compressed between lock ring 1070 and the body 1040 to bias the lock ring 1070 laterally toward the segment 1042. This also biases the pushbutton 1074 radially outward.

When the proximal housing 902 is being inserted into the compartment 1019 in the distal housing 1010, the distal end 930 of the proximal housing 902 pushes the lock ring 1070 laterally away from the segment 1042 against the bias of the spring 1080. This shifts the segment 1042 laterally into an adjacent recess 1085 in the body 1040. When the recess 939 (FIG. 32) on the proximal housing 902 moves axially beside the lock ring 1070, the spring 1080 pushes the lock ring 1070 back toward the segment 1042. This snaps the lock ring 1070 into the recess 939 to lock the proximal housing 902 in the distal housing 1010. The user can release the proximal housing 902 for removal from the distal housing 1010 by pushing the pushbutton 1076 back inward against the bias of the spring 1080.

Additional parts of the distal interface can be included in the distal housing 1010. For example, the distal housing 1010 may contain a proximity sensor, such as an inductive proximity sensor 1084, for sensing whether or not the proximal housing 902 is fully and properly seated in the distal housing 1010. A processor can be configured to actuate red and green LED's accordingly. The LED's can be installed in the housing 1010 for viewing through a fiber optic lens 1090 mounted in an aperture 1091 in the body 1040 of the housing 1010.

A fuse also can be included in the distal housing 1010 to irreversibly prevent the flow of excessive current from the power source. Alternatively, a circuit breaker can be used in place of or in conjunction with a fuse to temporarily prevent the flow of excessive current form the power source. In addition to a circuit breaker, the proximity sensor can respond to removal of the proximal housing 902 by opening an electronic circuit breaker to prevent the flow of any level of current from the source to the distal housing 1010.

Figure 40:
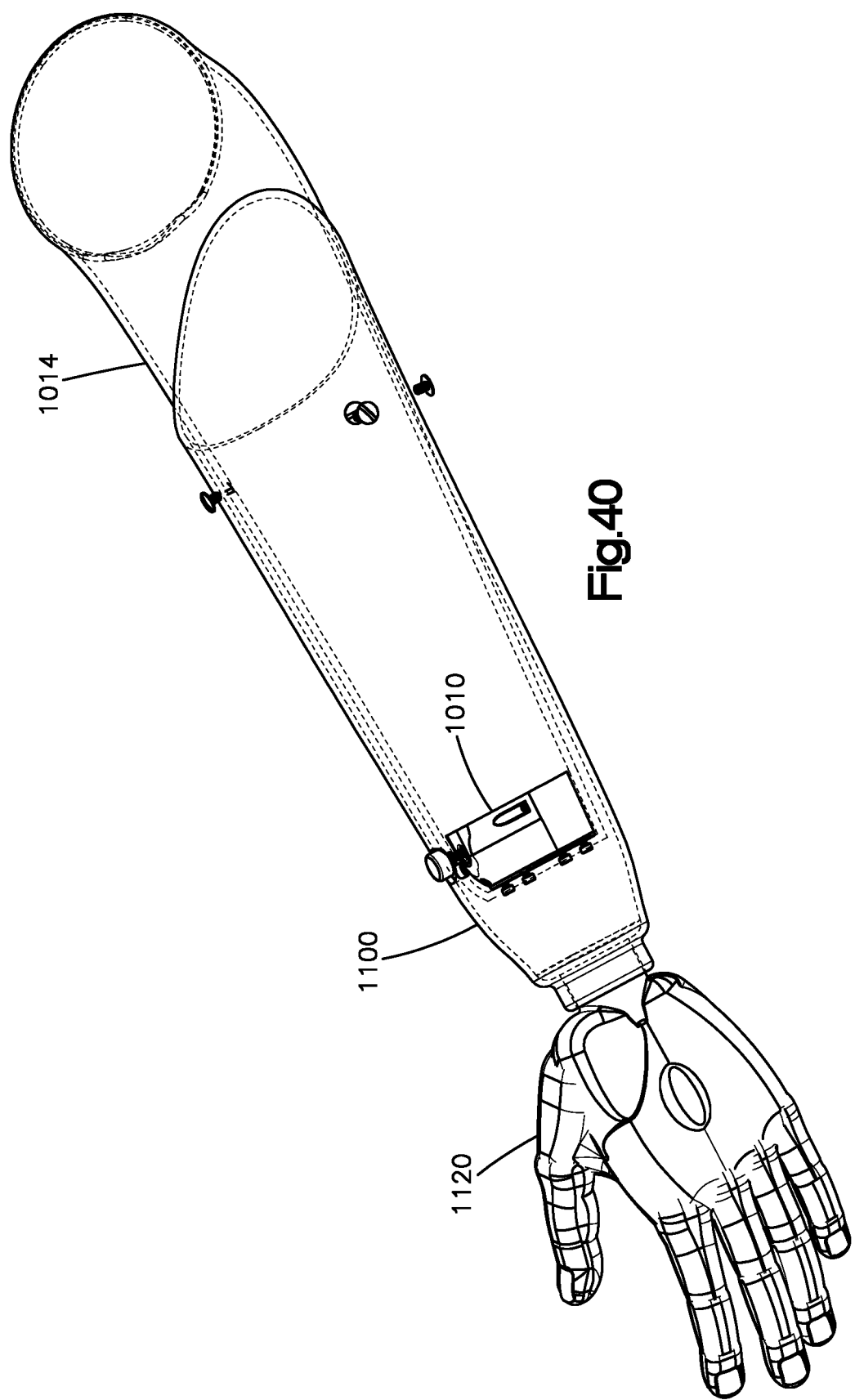
FIG. 40 is a side view of a prosthetic assembly including an assistive prosthetic device.

As shown in FIG. 40, the socket 1014 containing the distal housing 1010 can be inserted in a supplemental socket 1100 that is connected directly to an assistive device 1120. The cables can be routed through the space reaching longitudinally between the sockets 1014 and 1100. In this arrangement, the socket 1014 containing the distal housing 1010 is sized to fit the length of the residual limb, and the supplemental socket 1100 is sized for the overall length of the prosthetic assembly to provide the desired overall length of the limb.

Figure 41:
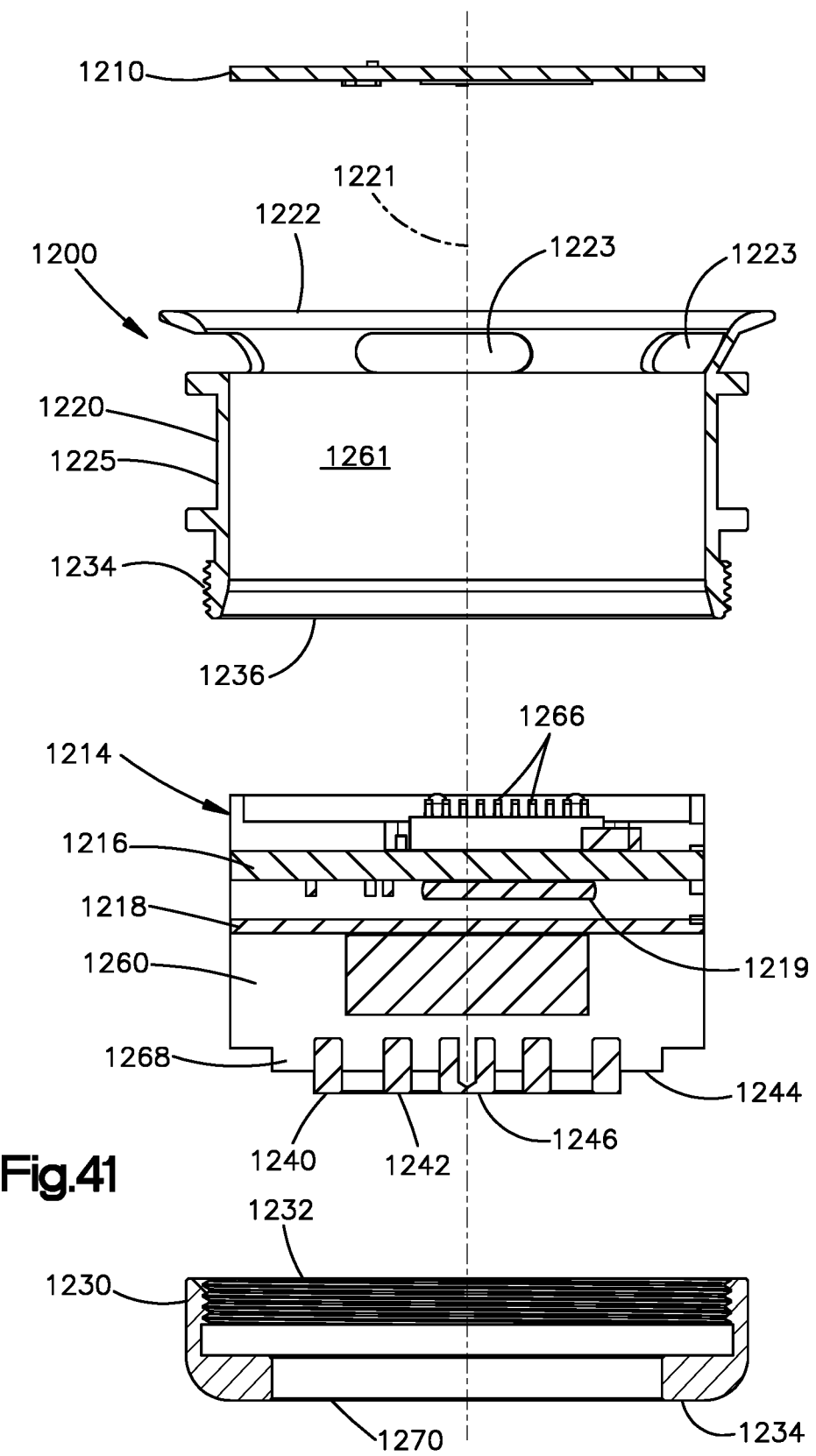
FIG. 41 is an exploded side view of parts of an alternative embodiment of a proximal interface.

Another example of a proximal housing 1200 is shown in the exploded view of FIG. 41. This example of a proximal housing 1200 is part of a proximal interface that further includes a first circuit board 1210 and a module 1214. The module 1214 contains multiple additional circuit boards which, in this example, include second and third circuit boards 1216 and 1218.

Figure 32:
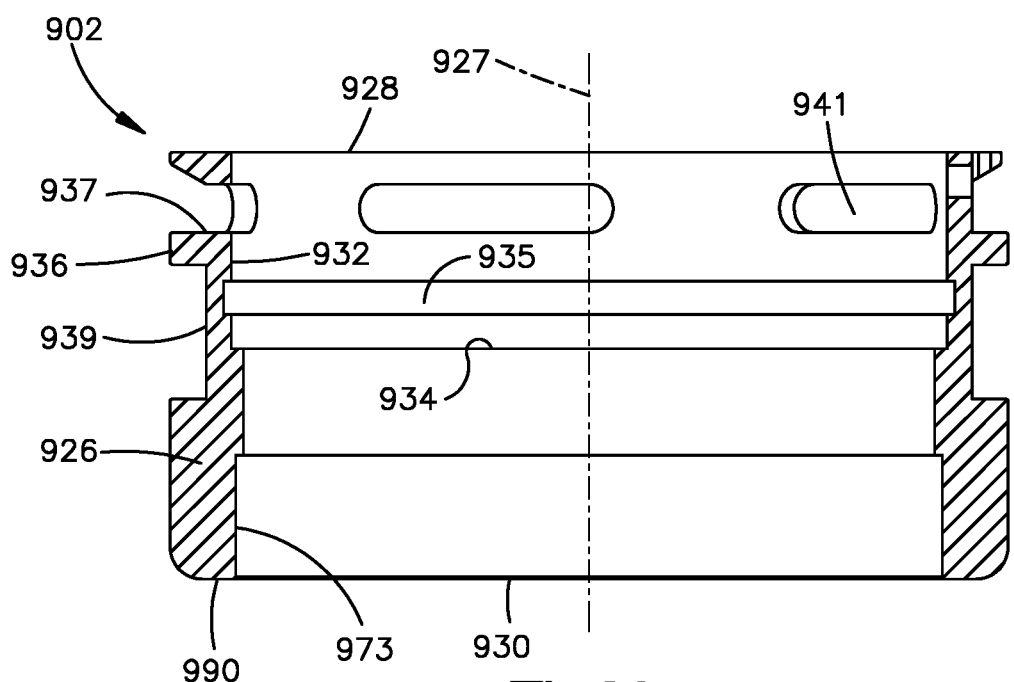
FIG. 32 is a side sectional view of a part shown in FIG. 30.

Like the housing 902 of FIG. 32, the housing 1200 of FIG. 41 has a metal wall 1220 with a cylindrical shape centered on an axis 1221. An open proximal end 1222 of the wall 1220 has slot-shaped apertures 1223 for a urethane umbrella to securely grip and hold the housing 1200 at the distal end of a liner. A recess 1225 in the cylindrical wall 1220 is configured to receive the lock ring 1070 in the distal housing 1010 in same manner as the recess 939 in the wall 926 of the housing 902.

The housing 1200 of FIG. 41 further includes a metal closure member 1230. The closure member 1230 in the illustrated example is a ring with an internal screw thread 1232 for engaging an external screw thread 1234 at the open distal end 1236 of the housing wall 1220.

The first circuit board 1210 can be connected with conductive paths extending from the liner in the same manner described above with reference to the circuit board 120 of FIG. 30. In assembly, the first circuit board is 1210 can be fixed within the housing 1200 by the same body of urethane material that forms the umbrella attaching the housing 1200 to the liner.

Figure 42:
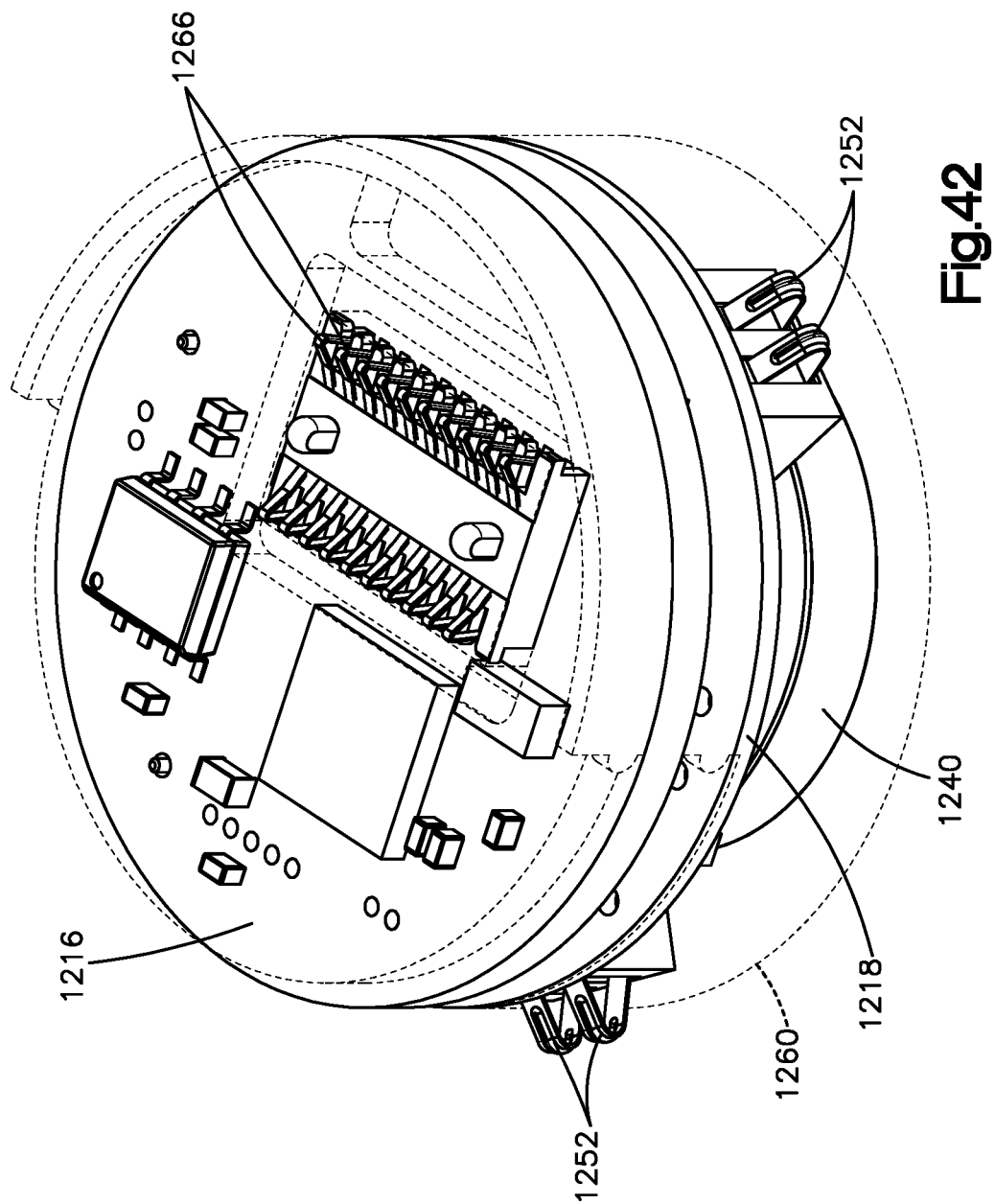
FIG. 42 is a top view of parts shown in FIG. 41.
Figure 43:
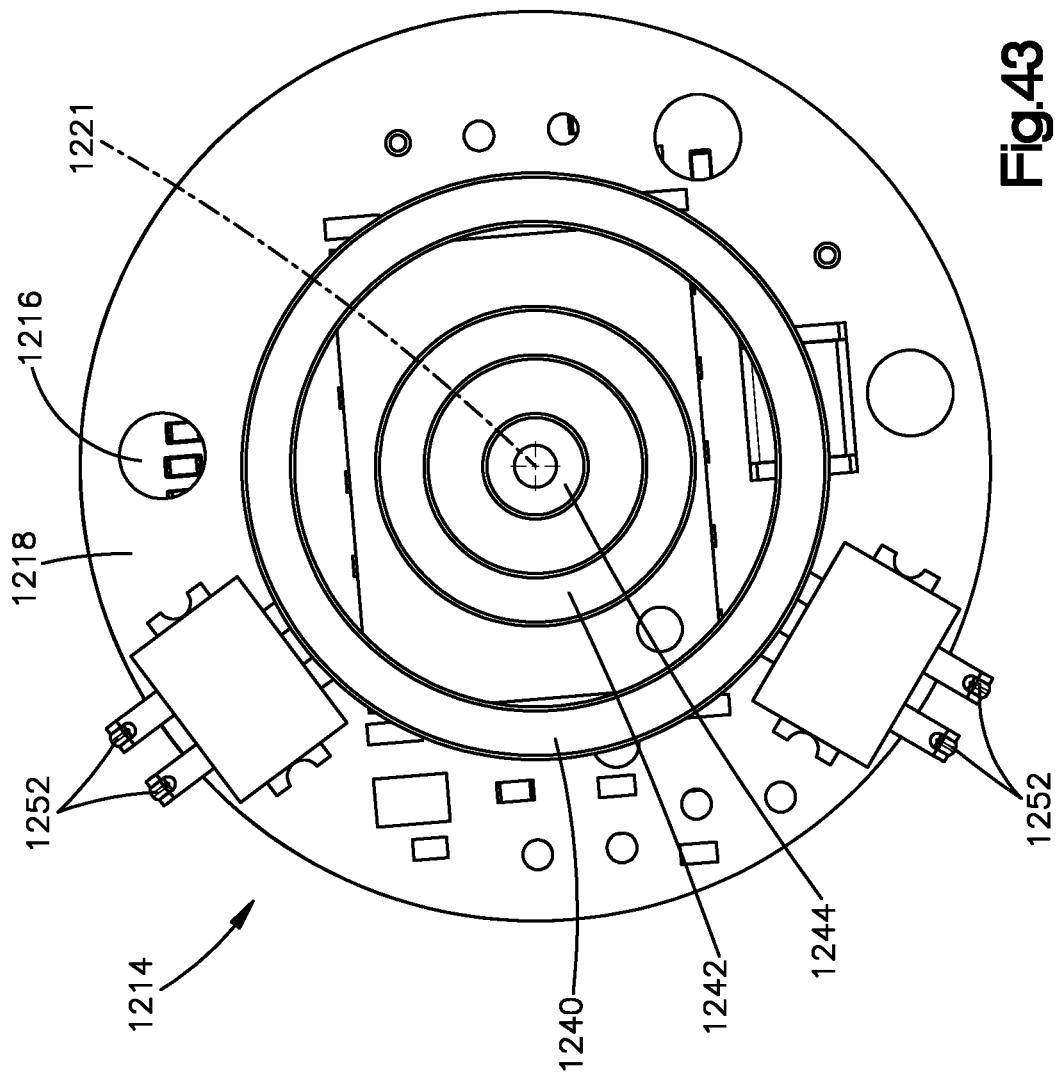
FIG. 43 is a bottom view of parts shown in FIG. 41.

In addition to the second and third circuit boards 1216 and 1218, the module 1214 includes a pair of coaxial ring-shaped electrical contacts 1240 and 1242 that are exposed at the distal end 1244 (FIG. 42) of the module 1214. These contacts 1240 and 1242 are interconnected with the circuit boards 1216 and 1218 as signal contacts. A central contact 1246 also is exposed at the distal end 1244. The central contact 1246 is interconnected with the circuit boards 1216 and 1218 as a power contact. Ground contacts 1252 project radially from the third circuit board 1218.

A body 1260 of urethane (FIGS. 41 and 42) encapsulates the circuit boards 1216 and 1218 within the module 1214. The urethane body 1260 has a cylindrical shape that is sized to fit closely within the cylindrical interior 1261 of the housing wall 1220. However, the urethane body 1260 is not injected into the housing 1200 in a molten state, but is formed in the cylindrical configuration outside of the housing 1200. The module 1214 can then be inserted into the housing 1200 through the open distal end 1236 of the housing wall 1220. Accordingly, when the module 1214 is in the inserted position, the urethane body 1261 is not adhered to the surrounding housing wall 1220, and the module 1214 can be nondestructively removed from the housing 1200 by sliding it out through the open distal end. The closure member 1230 can be screwed onto the open distal end 1236 of the housing wall 1220 to retain the module 1214 in the inserted position, and can be unscrewed from the open distal end 1236 to permit removal of the module 1214.

When the module 1214 is installed in the housing interior 1261, contacts 1266 on the second circuit board 1216 operatively engage and interconnect the second board 1216 with the first board 1210. A stepped portion 1268 of the urethane body 1260 supports the signal and power contacts 1240, 1242 and 1246 in positions coplanar with the open distal end 1270 of the closure member 1230. The signal and power contacts 1240, 1242 and 1246 are thereby exposed at the open distal end 1270 for contact with the corresponding contacts in the distal housing 1010. A ring-shaped edge 1234 of the closure member 1230 serves as a ground contact for engaging the ground contact 1036 in the distal housing 1010. The ground contacts 252 projecting radially from the module 1214 make contact with the housing wall 1220 so that the housing 1200 is included in a ground current path between the proximal interface and the distal interface.

The second circuit board 1216 and/or the third circuit board 1218 supports one or more processors that are configured to process signals for an assistive device as descried above. The first circuit board 1220 can support one or more less costly processors, or can merely support hardware for interconnecting with the conductive paths 140 and associated electrodes in the liner. When the liner needs to be replaced, the housing 1200 can be opened by unscrewing the closure member 1230 so that the module 1214 can be nondestructively removed from the housing 1200. The liner, the first circuit board 1210, and the housing wall 1220 can then be disposed of together while the second and third circuit boards 1216 and 1218 in the module 1214 are preserved for reuse.

Referring again to FIG. 40, the supplemental socket 1100 is fitted to the patient so that the overall length of the prosthetic assembly will match the desired length of the patient's limb. In the alternative arrangement of FIG. 44, a length-defining component 1300, such as a pylon, is provided in place of the supplemental socket 1100. The pylon 1300 also is fitted to the patient to provide the desired overall length of the prosthetic assembly. The pylon 1300 in this example is a cylindrical tube reaching longitudinally between a socket 1308 and an assistive prosthetic device 1310.

Figure 44:
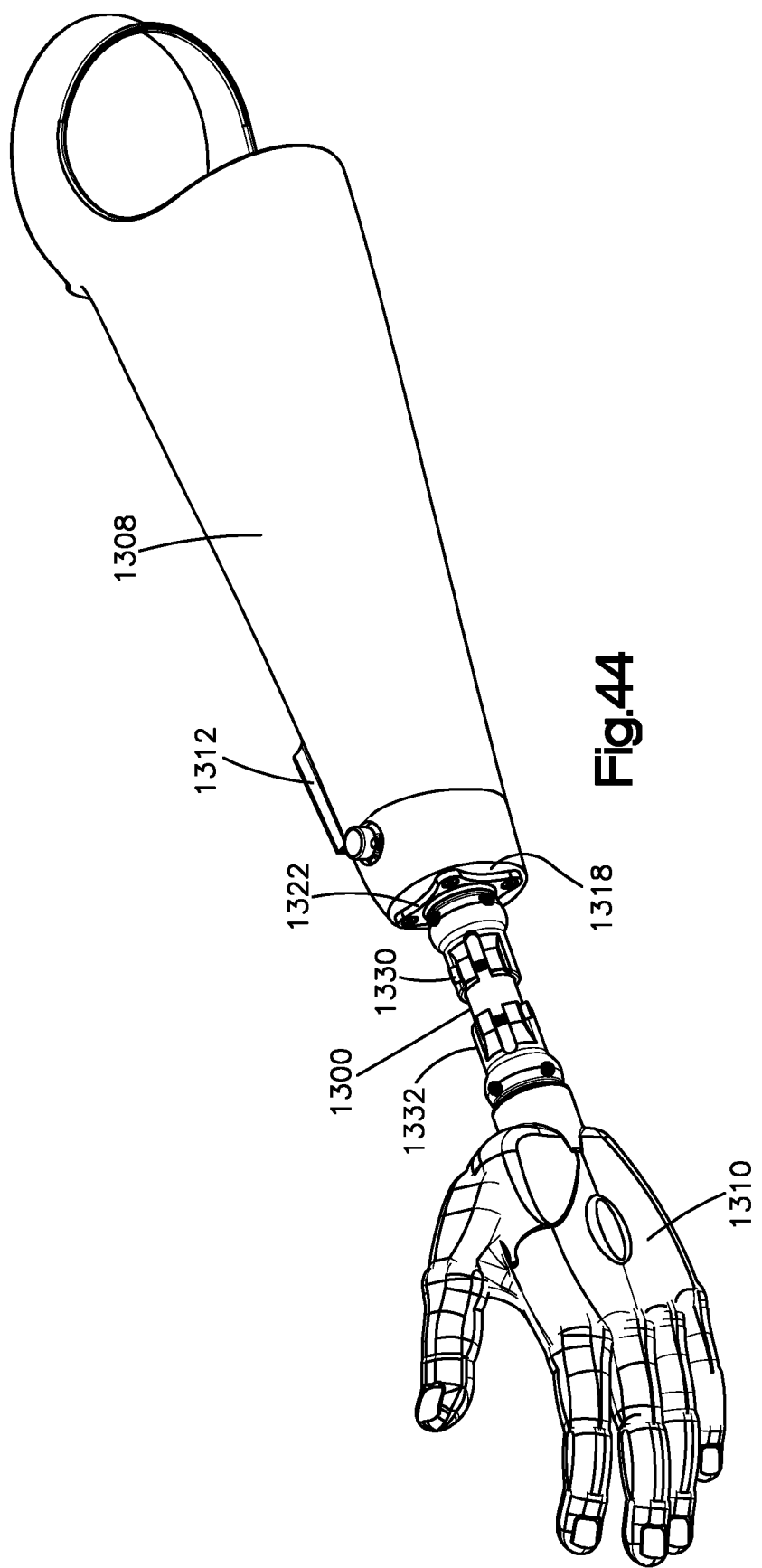
FIG. 44 is a view similar to FIG. 40, showing an alternative prosthetic assembly including an assistive prosthetic device.
Figure 45:
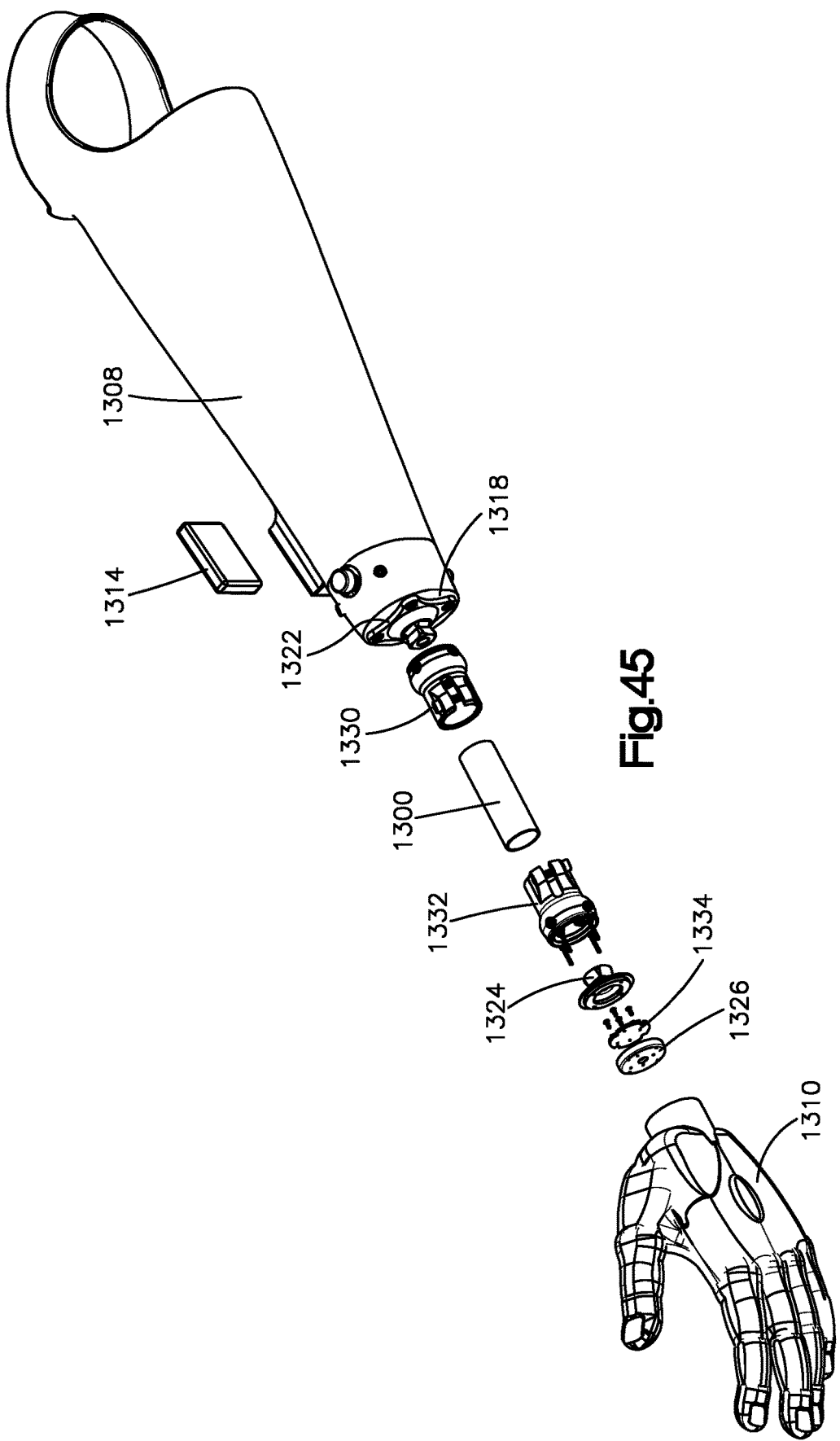
FIG. 45 is an exploded view of the prosthetic assembly of FIG. 44.

The assistive device 1310 of FIG. 44 is a prosthetic hand. The socket 1308 is configured to receive a residual arm, and is fitted to the length of the residual arm. A compartment 1312 is provided on the socket 1308 to contain a battery 1314 (FIG. 45) that serves as a power source for the prosthetic hand 1310. The socket 1308 contains a distal housing 1318 that is the same or substantially the same as the distal housing 1010 described above. A male pyramid connector 1322 is connected to the distal housing 1318. As shown in the exploded view of FIG. 45, another male pyramid connector 1324 is connected to a wrist unit 1326 which, in turn, is connected to the prosthetic hand 1310. The pylon 1300 is captured between a pair of female pyramid connectors 1330 and 1332 that are joined to the male pyramid connectors 1322 and 1324. Cabling can be routed through the pylon 1300 and the connectors to electrically interconnect circuit boards in the socket 1308 with a circuit board 1334 at the prosthetic hand 1310. The distance that the entire prosthetic assembly reaches from the residual limb to the prosthetic hand 1310 can be fitted to the patient merely by cutting the pylon 1300 to the appropriate length.

Figure 46:
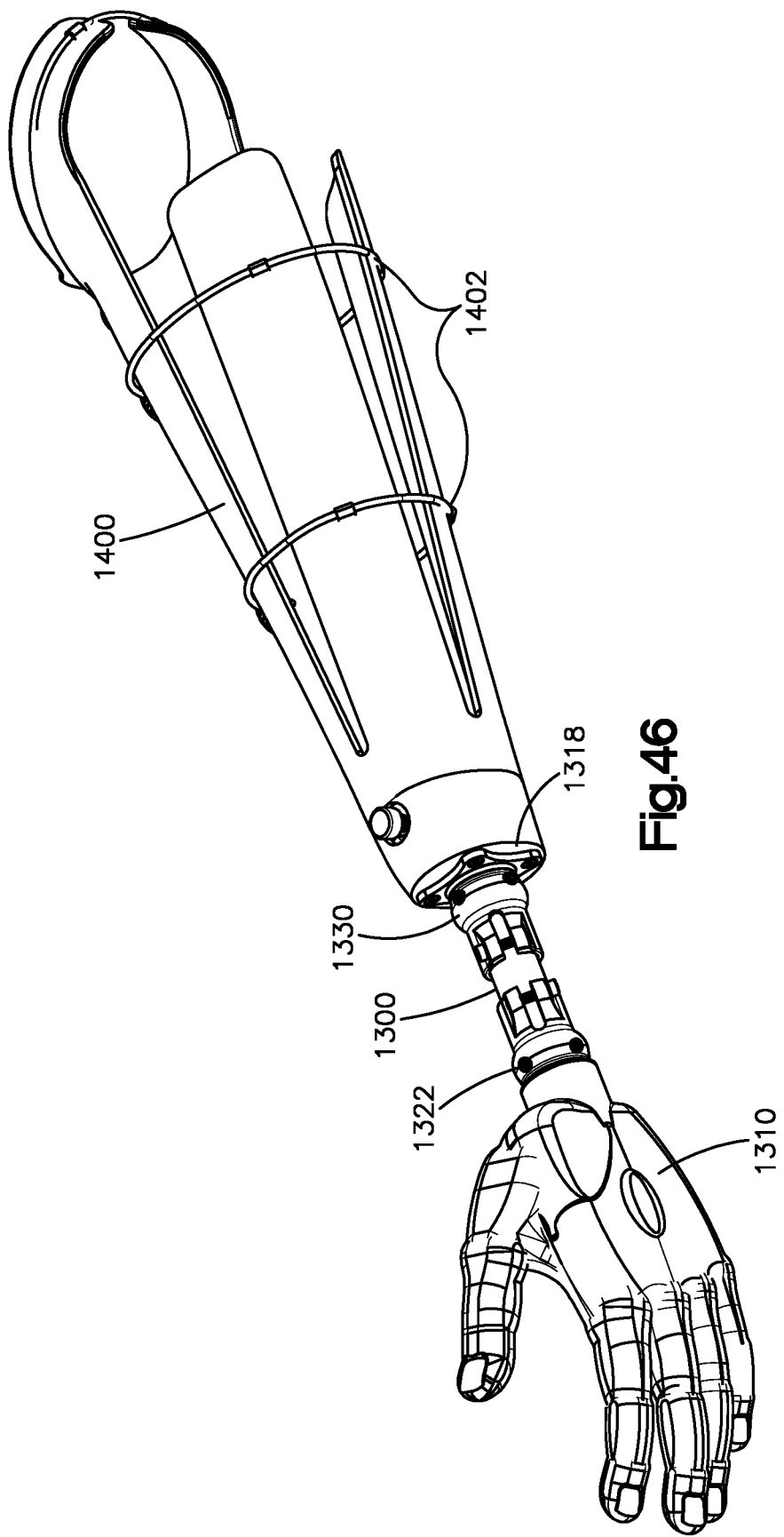
FIG. 46 is a view similar to FIG. 44 showing another alternative prosthetic assembly including an assistive prosthetic device.
Figure 47:
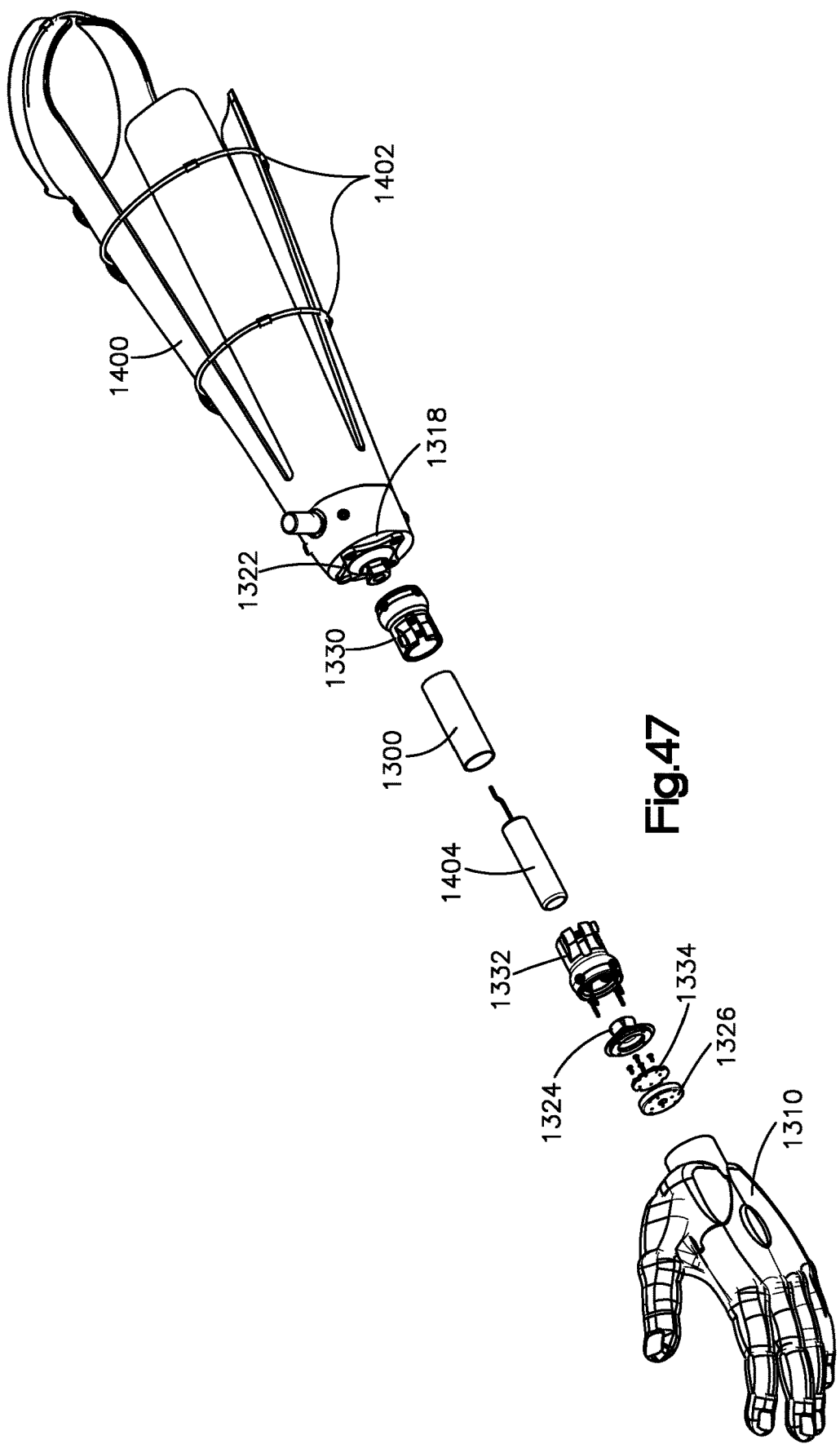
FIG. 47 is an exploded view of the prosthetic assembly of FIG. 46.

In the alternative arrangement of FIGS. 46 and 47, the distal housing 1318 is contained in an open frame socket 1400 with a tensioning system 1402. A battery 1404 is contained within the pylon 1300 instead a compartment on the socket 1400.

This written description sets for the best mode of carrying out the invention, and describes the invention so as to enable a person of ordinary skill in the art to make and use the invention, by presenting examples of the elements recited in the claims. The detailed descriptions of those elements do not impose limitations that are not recited in the claims, either literally or under the doctrine of equivalents.

What is claimed is:

1. An apparatus comprising:
   a fabric layer having an interior side and an exterior side;
   a conductive path including conductive thread overlying the fabric layer at the interior side of the fabric layer;
   a soft coating having an inner contact surface and an outer surface contacting the interior side of the fabric layer and covering the conductive path;
   an electrode located at the interior side of the fabric layer;
   a connector located within the soft coating, the connector overlying the fabric layer and electrically interconnecting the conductive thread with the electrode at the interior side of the fabric layer;
   a nonconductive cap received over the connector and having an inner surface that is substantially flush with the inner contact surface of the soft coating, the nonconductive cap holding a section of the conductive thread against the connector, whereby the nonconductive cap retains the section of the conductive thread in contact with the connector; and
   the connector and the nonconductive cap having bores that align to receive the electrode therein.

2. An apparatus for use with an assistive device, the apparatus comprising:
   a fabric layer;
   an electrode supported on the fabric layer;
   a housing attached to the fabric layer, the housing having a wall defining an interior of the housing, the wall having an open proximal end and an open distal end, and a closure member removably attached to the wall to cover the open distal end;
   a conductive path reaching from the electrode into the housing through the open proximal end;
   a processor mounted in the housing and communicating with the conductive path for processing signals between the electrode and an assistive device;
   a module removably located within the interior of the housing, the module having multiple interconnected circuit boards, a body that encapsulates the multiple interconnected circuit boards, signal contacts connected to at least one circuit board of the multiple interconnected circuit boards and that extend from a distal end of the module, and contacts that extend from a proximal end of the module that operatively engage and interconnect one of the multiple interconnected circuit boards with the processor; and wherein the closure member retains the module within the housing when the closure member is contacting the wall and covers the open distal end, and wherein removal of the closure member from the wall of the housing allows the module to be removed from and inserted into the interior of the housing through the open distal end.

3. An apparatus as defined in claim 2 wherein the wall and the closure member each have screw threads that engage each other to form a removable attachment between the wall and the closure member.

4. An apparatus as defined in claim 3 wherein the open distal end of the wall is circular and the closure member is a ring.

5. An apparatus as defined in claim 2 wherein the module has a distal end face that includes the signal contacts that are exposed at the open distal end of the housing when the module is installed in the housing and the closure member is attached to the wall.

6. An apparatus as defined in claim 5 wherein the signal contacts at the distal end face of the module include contacts that are ring-shaped.

7. An apparatus as defined in claim 2 further comprising a molded body of polymeric material attaching the housing to the fabric layer.

8. An apparatus comprising:
a fabric layer having an interior side and an exterior side;
a conductive path comprising conductive thread overlying the fabric layer at the interior side of the fabric layer;
an electrode located at the interior side of the fabric layer;
a connector electrically interconnecting the conductive thread with the electrode at the interior side of the fabric layer;
a nonconductive cap received over the connector and a section of the conductive thread to capture the section of conductive thread between the nonconductive cap and the connector, whereby the nonconductive cap retains the section of conductive thread in contact with the connector; and wherein the connector has a bottom surface facing the fabric layer, a top surface opposite the bottom surface, and a passage reaching through the connector from the bottom surface to the top surface, the conductive thread has a section overlying the fabric layer beneath the bottom surface of the connector, a section that reaches through the passage, and an end section that reaches outward from the passage and overlies the top surface of the connector, and the nonconductive cap is received over the end section of the conductive thread to retain the end section in contact with the top surface of the connector.

9. An apparatus as defined in claim 2, wherein the body of the module is made of polymeric material.

10. An apparatus as defined in claim 9, wherein the wall of the housing is cylindrical, the interior is cylindrical, and the body of polymeric material has a cylindrical configuration sized to fit closely with the cylindrical interior.

11. The apparatus as defined in claim 2, wherein the closure member includes an open distal end that allows the signal contacts of the module to extend therethrough to be exposed for contact with corresponding contacts.

12. The apparatus as defined in claim 2, where the module includes ground contacts projecting from the body that engage the housing.

13. The apparatus of claim 12, wherein the closure member is included in a ground current path from the module.

* * * * *